US012435143B2

(12) United States Patent
Morsey et al.

(10) Patent No.: US 12,435,143 B2
(45) Date of Patent: Oct. 7, 2025

(54) CANINIZED ANTIBODIES AGAINST CANINE CTLA-4

(71) Applicant: Intervet Inc., Madison, NJ (US)

(72) Inventors: Mohamad Morsey, Omaha, NE (US); Yuanzheng Zhang, Somerset, NJ (US); Ian Tarpey, St. Ives (GB)

(73) Assignee: INTERVET INC., Rahway, NJ (US)

( * ) Notice: Subject to any disclaimer, the term of this patent is extended or adjusted under 35 U.S.C. 154(b) by 942 days.

(21) Appl. No.: 17/626,239

(22) PCT Filed: Jul. 15, 2020

(86) PCT No.: PCT/EP2020/069923
§ 371 (c)(1),
(2) Date: Jan. 11, 2022

(87) PCT Pub. No.: WO2021/009187
PCT Pub. Date: Jan. 21, 2021

(65) Prior Publication Data

US 2022/0251208 A1 Aug. 11, 2022

Related U.S. Application Data

(60) Provisional application No. 63/048,873, filed on Jul. 7, 2020, provisional application No. 62/926,047, filed on Oct. 25, 2019, provisional application No. 62/874,287, filed on Jul. 15, 2019.

(51) Int. Cl.
*C07K 16/28* (2006.01)
*A61K 39/00* (2006.01)
*A61P 31/00* (2006.01)
*A61P 35/00* (2006.01)

(52) U.S. Cl.
CPC .... *C07K 16/2818* (2013.01); *A61K 2039/505* (2013.01); *A61P 31/00* (2018.01); *A61P 35/00* (2018.01); *C07K 2317/24* (2013.01); *C07K 2317/565* (2013.01); *C07K 2317/71* (2013.01); *C07K 2317/76* (2013.01); *C07K 2317/92* (2013.01)

(58) Field of Classification Search
CPC ............ C07K 16/2818; C07K 2317/24; C07K 2317/71; C07K 2317/76; C07K 2317/92; C07K 2317/20; C07K 2317/34; C07K 2317/70; C07K 2317/33; C07K 2317/565; C07K 2319/30; A61P 31/00; A61P 35/00; A61K 2039/505
See application file for complete search history.

(56) References Cited

U.S. PATENT DOCUMENTS

| | | | |
|---|---|---|---|
| 8,017,114 | B2 | 9/2011 | Korman et al. |
| 9,944,704 | B2 | 4/2018 | Morsey et al. |
| 10,106,607 | B2 | 10/2018 | Morsey et al. |
| 2018/0237535 | A1 | 8/2018 | Morsey et al. |

FOREIGN PATENT DOCUMENTS

| | | | |
|---|---|---|---|
| CN | 107074952 | A | 8/2017 |
| JP | 2014512809 | A | 5/2014 |
| JP | 2017500867 | A | 1/2017 |
| JP | 2017534267 | A | 11/2017 |
| JP | 2019506146 | A | 3/2019 |
| RU | 2627191 | C2 | 8/2017 |
| WO | 2000037504 | A2 | 6/2000 |
| WO | 2003060080 | A2 | 7/2003 |
| WO | 2010097597 | A1 | 9/2010 |
| WO | 2012120125 | A1 | 9/2012 |
| WO | WO 2012153126 | A1 | 11/2012 |
| WO | 2015091910 | A2 | 6/2015 |
| WO | WO 2015091914 | A2 | 6/2015 |
| WO | 2016050721 | A1 | 4/2016 |
| WO | 2016183469 | A1 | 11/2016 |
| WO | WO 2017062615 | A2 | 4/2017 |
| WO | WO 2017102920 | A1 | 6/2017 |

OTHER PUBLICATIONS

Badri et al., 2016, "Optimization of radiation dosing schedules for proneural glioblastoma," J. Math. Biol., 72(5):1301-1036 (Epub 2015).
Baylot et al., 2017, "TCTP Has a Crucial Role in the Different Stages of Prostate Cancer Malignant Progression," Results Probl. Cell Differ., 64:255-261.
Judge et al., 1999, "The role of CD80, CD86, and CTLA4 in alloimmune responses and the induction of long-term allograft survival," J. Immunol., 162(4):1947-1951.
Keskin et al., 2004, "A new, structurally nonredundant, diverse data set of protein-protein interfaces and its implications," Protein Sci., 13(4):1043-1055.
Muller et al., 2008, "Spliceosomal peptide P140 for immunotherapy of systemic lupus erythematosus: results of an early phase II clinical trial," Arthritis Rheum., 58(12):3873-3883.
Najafian et al., 2000, "CTLA4-Ig: a novel immunosuppressive agent," Expert Opin. Investig. Drugs, 9(9):2147-2157.
Pakula et al., 1989, "Genetic analysis of protein stability and function," Annu. Rev. Genet., 23:289-310.
Soskic et al., 2014, "Chapter Four—A Transendocytosis Perspective on the CD28/CTLA-4 Pathway," Adv. Immunol., 124:95-136.
Alegre, Maria-Luisa et al., Regulation of surface and intracellular expression of CTLA4 on mouse T cells, J. Immunol., 1996, 4762-4770, 157.
Aruffo, Alejandro et al., Molecular cloning of a CD28 cDNA by a high-efficiency COS cell expression system, Proc. Natl. Acad. Sci. USA, 1987, 8573-8577, 84.

(Continued)

*Primary Examiner* — Misook Yu
*Assistant Examiner* — Alec Jon Peters
(74) *Attorney, Agent, or Firm* — JONES DAY

(57) ABSTRACT

The present invention provides caninized murine antibodies against canine CTLA-4 that have specific sequences and a high binding affinity for canine CTLA-4. The present invention further provides epitopes of canine CTLA-4 for caninized murine antibodies against canine CTLA-4.5 The invention also relates to use of these antibodies in the treatment of cancer in canines and other companion animals.

20 Claims, 12 Drawing Sheets

Specification includes a Sequence Listing.

(56) References Cited

OTHER PUBLICATIONS

Attia, Peter et al., Autoimmunity Correlates With Tumor Regression in Patients With Metastatic Melanoma Treated With Anti-Cytotoxic T-Lymphocyte Antigen-4, Journal of Clinical Oncology, 2005, 6043-6053, 23(25).
Azuma, Miyuki et al., B70 antigen is a second ligand for CTLA-4 and CD28, Nature, 1993, 76-79, 366.
Bergeron et al., Comparative functional characterization of canine IgG subclasses, Veterinary Immunology and Immunopathology, 2014, pp. 31-41, 157.
Boutros, C. et al., Safety profiles of anti-CTLA-4 and anti-PD-1 antibodies alone and in combination, Nature Reviews Clinical Oncology, 2016, 473-486, 13.
Butte, Manish J. et al., Interaction of human PD-L1 and B7-1, Molecular Immunology, 2008, 3567-3572, 45.
Chemnitz, Jens M. et al., SHP-1 and SHP-2 Associate with Immunoreceptor Tyrosine-Based Switch Motif of Programmed Death 1 upon Primary Human T Cell Stimulation, but Only Receptor Ligation Prevents T Cell Activation, J. Immunol., 2004, 945-954, 173.
Comin-Anduix, Begona et al., Detailed analysis of immunologic effects of the cytotoxic T lymphocyte-associated antigen 4-blocking monoclonal antibody tremelimumab in peripheral blood of patients with melanoma, Journal of Translational Medicine, 2008, 1-14, 6:22.
Freeman et al., Engagement of the PD-1 Immunoinhibitory Receptor by a Novel B7 Family Member Leads to Negative Regulation of Lymphocyte Activation, J. Exp. Med., 2000, pp. 1027-1034, vol. 192.
Freeman, Gordon J. et al., Cloning of B7-2: a CTLA-4 Counter-Receptor That Costimulates Human T Cell Proliferation, Science, 1993, 909-912, 262.
Freeman, Gordon J. et al., CTLA-4 and CD28 mRNA are coexpressed in most T cells after activation. Expression of CTLA-4 and CD28 mRNA does not correlate with the pattern of lymphokine production, J. Immunol., 1992, 3795-3801, 149.
Gearing, DP et al., A fully caninised anti-NGF monoclonal antibody for pain relief in dogs, BMC Veterinary Research, 2013, pp. 1-11, vol. 9 (226), WO.
Gross, Jane A. et al., Identification and distribution of the costimulatory receptor CD28 in the mouse, J. Immunol., 1992, 380-388, 149.
Hodi, F. Stephen et al., Biologic activity of cytotoxic T lymphocyte-associated antigen 4 antibody blockade in previously vaccinated metastatic melanoma and ovarian carcinoma patients, PNAS, 2003, 4712-4717, 100(8).
Inaba, K. et al., The Tissue Distribution of the B7-2 Costimulator in Mice: Abundant Expression on Dendritic Cells In Situ and During Maturation In Vitro, The Journal of Experimental Medicine, 1994, 1849-1860, 180.
Jenkins, Marc K. et al., Antigen Presentation by Chemically Modified Splenocytes Induces Antigen-Specific T Cell Unresponsiveness in Vitro and in Vivo, J. Exp. Med., 1987, 302-319, 165.
Jenkins, Marc K. et al., CD28 delivers a costimulatory signal involved in antigen-specific IL-2 production by human T cells, J. Immunol., 1991, 2461-2466, 147.
Jenkins, Marc K. et al., Molecular events in the induction of a nonresponsive state in interleukin 2-producing helper T-lymphocyte clones, Proc. Natl. Acad. Sci. USA, 1987, 5409-5413, 84.
Jin, Hyun-Tak et al., Role of PD-1 in Regulating T-Cell Immunity, Current Topics in Microbiology and Immunology, 2010, 17-37, 350.
Krummel, Matthew F. et al., CTLA-4 Engagement Inhibits IL-2 Accumulation and Cell Cycle Progression upon Activation of Resting T Cells, J. Exp. Med., 1996, 2533-2540, 183.
Larsen, Christian P. et al., Regulation of Immunostimulatory Function and Costimulatory Molecule (B7-1 and 37-2) Expression on Murine Dendritic Cells, The Journal of Immunology, 1994, 5208-5219, 152.
Leach, DR et al., Enhancement of antitumor immunity by CTLA-4 blockade, Science, 1996, pp. 1734-1736, 271.
Linsley, Peter S. et al., Binding of the B Cell Activation Antigen B7 to CD28 Costimulates T Cell Proliferation and Interleukin 2 mRNA Accumulation, J. Exp. Med., 1991, 721-730, 173.
Linsley, Peter S. et al., T-cell antigen CD28 mediates adhesion with B cells by interacting with activation antigen B7/BB-1, Proc. Natl. Acad. Sci. USA, 1990, 5031-5035, 87.
Maekawa, Naoya et al., A canine chimeric monoclonal antibody targeting PD-LI and its clinical efficacy in canine pral malignant melanoma or undifferentiated sarcoma, Scientific Reports, 2017, 1-12, 7(1).
Mandelbrot, Didier A. et al., B7-1 or B7-2 Is Required to Produce the Lymphoproliferative Phenotype in Mice Lacking Cytotoxic T Lymphocyte-associated Antigen 4 (CTLA-4), J. Exp. Med., 1999, 435-440, 189.
Nishimura et al., Autoimmune Dilated Cardiomyopathy in PD-1 Receptor-Deficient Mice, Science, 2001, pp. 319-322, vol. 291.
Nishimura, Hiroyuki et al., Development of Lupus-like Autoimmune Diseases by Disruption of the PD-1 Gene Encoding an ITIM Motif-Carrying Immunoreceptor, Immunity, 1999, 141-151, 11(2).
Petrovas, Constantinos et al., PD-1 is a regulator of virus-specific CD8+ T cell survival in HIV infection, J. Exp. Med., 2006, 2281-2292, 203.
Phan, Giao Q. et al., Cancer regression and autoimmunity induced by cytotoxic T lymphocyte-associated antigen 4 blockade in patients with metastatic melanoma, PNAS, 2003, 8372-8377, 100.
Razi-Wolf, Ziba et al., Expression and function of the murine B7 antigen, the major costimulatory molecule expressed by peritoneal exudate cells, Proc. Natl. Acad. Sci. USA, 1992, 4210-4214, 89.
Reiser, Hans et al., Murine B7 antigen provides an efficient costimulatory signal for activation of murine T lymphocytes via the T-cell receptor/CD3 complex, Proc. Natl. Acad. Sci. USA, 1992, 271-275, 89.
Riley, James L. et al., The CD28 family: a T-cell rheostat for therapeutic control of T-cell activation, Blood, 2005, 13-21, 105.
Sansom, D. M., CD28, CTLA-4 and their ligands: who does what and to whom?, Immunology, 2000, 169-177, 101.
Sansom, David M. et al., B7/BB1, the ligand for CD28, is expressed on repeatedly activated human T cells in vitro. Eur J Immunol, 1993, 295-298, 23.
Schwartz, Ronald H., A Cell Culture Model for T Lymphocyte Clonal Anergy, Science, 1990, 1349-1356, 248.
Sharpe, Arlene H. et al., The B7-CD28 Superfamily, Nature Reviews, 2002, 116-126, 2.
Soskic, Blagoje et al., A Transendocytosis Perspective on the CD28/CTLA-4 Pathway, Advances in Immunology, 2014, 96-123, Chapter 4.
Tagawa, Michihito et al., Evaluation of costimulatory molecules in dogs with B cell high grade lymphoma, PLoS ONE, 2018, 1-14, 13(7).
Tivol, Elizabeth A. et al., CTLA4Ig prevents lymphoproliferation and fatal multiorgan tissue destruction in CTLA-4-deficient mice, J. Immunol., 1997, 5091-5094, 158.
Tivol, Elizabeth A. et al., Loss of CTLA-4 Leads to Massive Lymphoproliferation and Fatal Multiorgan Tissue Destruction, Revealing a Critical Negative Regulatory Role of CTLA-4, Immunity, 1995, 541-547, 3.
Van Der Merwe, P. Anton et al., CD80 (B7-1) Binds Both CD28 and CTLA-4 with a Low Affinity and Very Fast Kinetics, J. Exp. Med., 1997, 393-403, 185.
Walunas, Theresa L. et al., CTLA-4 Can Function as a Negative Regulator of T Cell Activation, Immunity, 1994, 405-413, 1.
Walunas, Theresa L. et al., CTLA-4 Ligation Blocks CD28-dependent T Cell Activation, J. Exp. Med., 1996, 2541-2550, 183.
Waterhouse, Paul et al., Lymphoproliferative Disorders with Early Lethality in Mice Deficient in Ctla-4, Science, 1995, 985-988, 270.
Zhang et al., Structural and Functional Analysis of the Costimulatory Receptor Programmed Death-1, Immunity, 2004, pp. 337-347, vol. 20.

A.

B.

SEQUENCE LISTING

```
<160> NUMBER OF SEQ ID NOS: 138

<210> SEQ ID NO 1
<211> LENGTH: 348
<212> TYPE: DNA
<213> ORGANISM: Mus musculus

<400> SEQUENCE: 1

cagatccagt tggtgcagtc tggacctgag ctgaagaagc ctggagagac agtcaagatc     60

tcctgcaagg cttctgggta taccttcaca aactatggaa tgaactgggt gaagcaggct    120

ccaggaaagg gtttaaagtg gatgggctgg ataaacacct acactggaga gccaacatat    180

gctgatgact tcaagggacg gtttgccttc tctttggaaa cctctgccag cactgcctat    240

ttgcagatca acaacctcaa aaatgaggac atggctacat atttctgtgc aagacggtca    300

atttattacc cgtactgggg ccaaggcacc actctcacag tctcctca                 348


<210> SEQ ID NO 2
<211> LENGTH: 116
<212> TYPE: PRT
<213> ORGANISM: Mus musculus

<400> SEQUENCE: 2

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Arg Ser Ile Tyr Tyr Pro Tyr Trp Gly Gln Gly Thr Thr Leu
            100                 105                 110

Thr Val Ser Ser
        115


<210> SEQ ID NO 3
```

<211> LENGTH: 348
<212> TYPE: DNA
<213> ORGANISM: Mus musculus

<400> SEQUENCE: 3
cagatccagt tggtacagtc tggacctgag ctgaagaagc ctggagagac agtcaagatc 60
tcctgcaagg cttctgggta taccttcaca acctatggag tgagctgggt gaaacaggct 120
ccaggaaagg gtttaaggtg gatgggctgg ataaacacct actctggaat gccaacatat 180
gttgatgact tcaagggacg gtttgccttc tctttggaaa cctctgccag cactgccttt 240
ttgcagatca acaacctcaa aaatgaggac acggctatat atttctgtgc aagacggggt 300
atctcctttg actactgggg ccaaggcacc actctcacag tctcctca 348

<210> SEQ ID NO 4
<211> LENGTH: 116
<212> TYPE: PRT
<213> ORGANISM: Mus musculus

<400> SEQUENCE: 4

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Thr Tyr
20 25 30

Gly Val Ser Trp Val Lys Gln Ala Pro Gly Lys Gly Leu Arg Trp Met
35 40 45

Gly Trp Ile Asn Thr Tyr Ser Gly Met Pro Thr Tyr Val Asp Asp Phe
50 55 60

Lys Gly Arg Phe Ala Phe Ser Leu Glu Thr Ser Ala Ser Thr Ala Phe
65 70 75 80

Leu Gln Ile Asn Asn Leu Lys Asn Glu Asp Thr Ala Ile Tyr Phe Cys
85 90 95

Ala Arg Arg Gly Ile Ser Phe Asp Tyr Trp Gly Gln Gly Thr Thr Leu
100 105 110

Thr Val Ser Ser
115

<210> SEQ ID NO 5
<211> LENGTH: 360
<212> TYPE: DNA
<213> ORGANISM: Mus musculus

<400> SEQUENCE: 5
gaggtgaagc tggtggagtc tggaggaggc ttggtacagc ctgggggttc cctgagtctc 60
tcctgtgcaa cttctggatt caccttcagt gattactaca tgagctgggt ccgccagtct 120
ccggggaagg cacttgagtg gatgggtttt attagaaaca aagctaatgg ttacacaaca 180
gagtacagcg catctctgaa gggtcggttc accatctcca gagataattc ccaaagcatc 240
ctctatcttc aaatgaatgt cctgagagct gaggacagtg ccacttatta ctgtgtaaga 300
tttgggttaa tgtactactt tgactactgg ggccaaggca ccactctcac agtctcctca 360

<210> SEQ ID NO 6
<211> LENGTH: 120
<212> TYPE: PRT
<213> ORGANISM: Mus musculus

<400> SEQUENCE: 6

Glu Val Lys Leu Val Glu Ser Gly Gly Gly Leu Val Gln Pro Gly Gly
1 5 10 15

Ser Leu Ser Leu Ser Cys Ala Thr Ser Gly Phe Thr Phe Ser Asp Tyr
20 25 30

Tyr Met Ser Trp Val Arg Gln Ser Pro Gly Lys Ala Leu Glu Trp Met
35 40 45

Gly Phe Ile Arg Asn Lys Ala Asn Gly Tyr Thr Thr Glu Tyr Ser Ala
50 55 60

Ser Leu Lys Gly Arg Phe Thr Ile Ser Arg Asp Asn Ser Gln Ser Ile
65 70 75 80

Leu Tyr Leu Gln Met Asn Val Leu Arg Ala Glu Asp Ser Ala Thr Tyr
85 90 95

Tyr Cys Val Arg Phe Gly Leu Met Tyr Tyr Phe Asp Tyr Trp Gly Gln
100 105 110

Gly Thr Thr Leu Thr Val Ser Ser
115 120

<210> SEQ ID NO 7
<211> LENGTH: 348
<212> TYPE: DNA
<213> ORGANISM: Mus musculus

<400> SEQUENCE: 7
cagatccagt tggtgcagtc tggacctgag ctgaagaagc ctggagagac agtcaagatc 60
tcctgcaagg cttctgggta taccttcaca aactatggaa tgaactgggt gaagcaggct 120
ccaggaaagg gtttaaagtg gatgggctgg ataaacacct acactggaga gccaacatat 180
gctgatgact tcaagggacg gtttgccttc tctttggaaa cctctgccag cactgcctat 240
ttgcagatca acaacctcaa aaatgaggac acggctacat atttctgtgc aagaaggggg 300
acctactata ggccctgggg ccaaggcacc actctcacag tctcctca 348

<210> SEQ ID NO 8
<211> LENGTH: 116
<212> TYPE: PRT
<213> ORGANISM: Mus musculus

<400> SEQUENCE: 8

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Ala Asp Asp Phe
50 55 60

Lys Gly Arg Phe Ala Phe Ser Leu Glu Thr Ser Ala Ser Thr Ala Tyr
65 70 75 80

Leu Gln Ile Asn Asn Leu Lys Asn Glu Asp Thr Ala Thr Tyr Phe Cys
85 90 95

Ala Arg Arg Gly Thr Tyr Tyr Arg Pro Trp Gly Gln Gly Thr Thr Leu
100 105 110

Thr Val Ser Ser
115

<210> SEQ ID NO 9
<211> LENGTH: 348
<212> TYPE: DNA
<213> ORGANISM: Mus musculus

<400> SEQUENCE: 9
cagatccagt tggtgcagtc tggacctgag ctgaagaagc ctggagagac agtcaagatc 60
tcctgcaagg cttctggata taccttcaca aactatggaa tgaactgggt gaagcaggct 120
ccaggaaagg gtttaaagtg gatgggctgg ataaacacct acactggaga gccaacatat 180
gctgatgact tcaagggacg gttgccttc tctttggaaa cctctgccag cactgccttt 240
ttgcagatca acaacctcaa aaatgaggac acggctacat atttctgtgc aaggcggggg 300
gtacgactgg actactgggg ccaaggcacc actctcacag tctcctca 348

<210> SEQ ID NO 10
<211> LENGTH: 116
<212> TYPE: PRT
<213> ORGANISM: Mus musculus

<400> SEQUENCE: 10

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Ala Asp Asp Phe
50 55 60

Lys Gly Arg Val Ala Phe Ser Leu Glu Thr Ser Ala Ser Thr Ala Phe
65 70 75 80

Leu Gln Ile Asn Asn Leu Lys Asn Glu Asp Thr Ala Thr Tyr Phe Cys
85 90 95

Ala Arg Arg Gly Val Arg Leu Asp Tyr Trp Gly Gln Gly Thr Thr Leu
100 105 110

Thr Val Ser Ser
115

<210> SEQ ID NO 11
<211> LENGTH: 363
<212> TYPE: DNA
<213> ORGANISM: Mus musculus

<400> SEQUENCE: 11
caggtccaac tgcagcagcc tgggactgaa ctggtgaagc ctggggcttc agtgaagctg 60
tcctgcaagg cctctggcta caccttcacc agctactgga tgcactgggt gaagcagagg 120
cctggacaag gccttgagtg gattggaaat atcaatccta gcaatggtgg tactaggttc 180
aatgagaagt tcaagaacaa ggccacactg actgaagaca aatcctccag cacagcctac 240
atgcagctca gtagcctgac atctgaggac tctgcggtct attattgtgc aagatcgaac 300
tacggtagtg gctgggcctg gtttgcttac tggggccaag ggactctggt cactgtctct 360
gca 363

<210> SEQ ID NO 12
<211> LENGTH: 121
<212> TYPE: PRT
<213> ORGANISM: Mus musculus

<400> SEQUENCE: 12

```
Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Arg Phe Asn Glu Lys Phe
    50                  55                  60

Lys Asn Lys Ala Thr Leu Thr Glu Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Asn Tyr Gly Ser Gly Trp Ala Trp Phe Ala Tyr Trp Gly
            100                 105                 110

Gln Gly Thr Leu Val Thr Val Ser Ala
        115                 120
```

<210> SEQ ID NO 13
<211> LENGTH: 336
<212> TYPE: DNA
<213> ORGANISM: Mus musculus

<400> SEQUENCE: 13

```
gatgttttga tgacccaaac tccactctcc ctgcctgtca gtcttggaga tcaagcctcc      60

atctcttgca gatctagtca gagcattgta tatagtaatg gaaacaccta tttagaatgg     120

tacctgcaga aaccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tctgggagtt tattactgct ttcaaggttc acatgttccg     300

tggacgttcg gtggaggcac caagctggaa atcaaa                               336
```

<210> SEQ ID NO 14
<211> LENGTH: 112
<212> TYPE: PRT
<213> ORGANISM: Mus musculus

<400> SEQUENCE: 14

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 15
<211> LENGTH: 336

<212> TYPE: DNA
<213> ORGANISM: Mus musculus

<400> SEQUENCE: 15
gatgttttga tgacccagac tccactctcc ctgcctgtca gtcttggaga tcacgcctcc 60
atctcttgca aatctagtca gagcattgta tatattaatg gaaacaccta tttagaatgg 120
tacctgcaga agccaggcca gtctccaaag ctcctgatct acaaagtttc caaacgattt 180
tctggggtcc cagacaggtt cagtggcagt ggatcaggga cagatttcac actcaagatc 240
agcagagtgg aggctgagga tctgggagtt tattactgct ttcaaggttc acatgttccg 300
tggacgttcg gtggaggcac caagctggaa atcaaa 336

<210> SEQ ID NO 16
<211> LENGTH: 112
<212> TYPE: PRT
<213> ORGANISM: Mus musculus

<400> SEQUENCE: 16

Asp Val Leu Met Thr Gln Thr Pro Leu Ser Leu Pro Val Ser Leu Gly
1 5 10 15

Asp His Ala Ser Ile Ser Cys Lys Ser Ser Gln Ser Ile Val Tyr Ile
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Lys Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Trp Thr Phe Gly Gly Gly Thr Lys Leu Glu Ile Lys
100 105 110

<210> SEQ ID NO 17
<211> LENGTH: 324
<212> TYPE: DNA
<213> ORGANISM: Mus musculus

<400> SEQUENCE: 17
gaaaatgtgc tcatccagtc tccagcaatc atgtctgctt ctccagggga aaaggtcacc 60
atgacctgca gggccagctc aagtgtaagt tccagttact tgcactggta ccagcagaag 120
tcaggtgcct cccccaaact ctggattttt agcacatcca acttggcttc tggagtccct 180
gctcgcttca gtggcagtgg gtctgggacc tcttattctc tcacaatcaa cagtgtggag 240
gctgaagatg ctgccactta ttactgccag cagtacagtg gtctcccact cacgttcgga 300
ggggggacca agctggaaat aaaa 324

<210> SEQ ID NO 18
<211> LENGTH: 108
<212> TYPE: PRT
<213> ORGANISM: Mus musculus

<400> SEQUENCE: 18

Glu Asn Val Leu Ile Gln Ser Pro Ala Ile Met Ser Ala Ser Pro Gly
1 5 10 15

Glu Lys Val Thr Met Thr Cys Arg Ala Ser Ser Ser Val Ser Ser Ser
20 25 30

```
Tyr Leu His Trp Tyr Gln Gln Lys Ser Gly Ala Ser Pro Lys Leu Trp
        35                  40                  45

Ile Phe Ser Thr Ser Asn Leu Ala Ser Gly Val Pro Ala Arg Phe Ser
    50                  55                  60

Gly Ser Gly Ser Gly Thr Ser Tyr Ser Leu Thr Ile Asn Ser Val Glu
65                  70                  75                  80

Ala Glu Asp Ala Ala Thr Tyr Tyr Cys Gln Gln Tyr Ser Gly Leu Pro
                85                  90                  95

Leu Thr Phe Gly Gly Gly Thr Lys Leu Glu Ile Lys
            100                 105


<210> SEQ ID NO 19
<211> LENGTH: 336
<212> TYPE: DNA
<213> ORGANISM: Mus musculus

<400> SEQUENCE: 19

gatgttttga tgacccaaac tccactctcc ctgcctgtca gtcttggaga tcaagcctcc      60

atctcttgca gatctagtca gagtattgta tatagtcatg gaaacaccta tttagaatgg     120

tacctgcaga aaccaggcca gtctccaaag gtcctgatct acaaagtttc caaccgattt     180

tctggggtcc cagacaggtt cagtggcagt ggatcaggga cagatttcac actcaagatc     240

agcagagtgg aggctgagga tctgggagtt tattactgct ttcaaggttc acatgttccg     300

tggacgttcg gtggaggcac caagctggaa atcaaa                               336


<210> SEQ ID NO 20
<211> LENGTH: 112
<212> TYPE: PRT
<213> ORGANISM: Mus musculus

<400> SEQUENCE: 20

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

His Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110


<210> SEQ ID NO 21
<211> LENGTH: 336
<212> TYPE: DNA
<213> ORGANISM: Mus musculus

<400> SEQUENCE: 21

gatgttttga tgacccaaac tccactctcc ctgcctgtca gtcttggaga tcaagcctcc      60

atctcttgca gatctagtca gagcattgta tatattagtg gaagcaccta tttagaatgg     120

tatctgcaga aaccaggcca gtctccaaag ctcctgatct acaaagtttc cagtcgattt     180
```

```
tctggggtcc cagacaggtt cagtggcagt ggatcaggga cagatttcac actcaagatc    240

agcagagtgg aggctgagga tctgggagtt tattactgct ttcaaggttc acatgttccg    300

tggacgttcg gtggaggcac caagctggaa atcaaa                              336


<210> SEQ ID NO 22
<211> LENGTH: 112
<212> TYPE: PRT
<213> ORGANISM: Mus musculus

<400> SEQUENCE: 22

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ile
            20                  25                  30

Ser Gly Ser Thr Tyr Leu Glu Trp Tyr Leu Gln Lys Pro Gly Gln Ser
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110


<210> SEQ ID NO 23
<211> LENGTH: 321
<212> TYPE: DNA
<213> ORGANISM: Mus musculus

<400> SEQUENCE: 23

gacatccaga tgaaccagtc tccatccagt ctgtctgcat cccttggaga cacaattacc     60

atcacttgcc atgccagtca gaacattaat gtttggttaa gctggtacca gcagaaacca    120

ggaaatattc ctaaactttt gatctataag tcttccaact tgcacacagg cgtcccatca    180

aggtttagtg gcagtggatc tggaacaggt ttcacattaa ccatcagcag cctgcagcct    240

gaagacattg ccacttacta ctgtcaacag ggtcaaagtt atccgtggac gttcggtgga    300

ggcaccaagc tggaaatcaa a                                              321


<210> SEQ ID NO 24
<211> LENGTH: 107
<212> TYPE: PRT
<213> ORGANISM: Mus musculus

<400> SEQUENCE: 24

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ser Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80
```

```
Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105


<210> SEQ ID NO 25
<211> LENGTH: 1353
<212> TYPE: DNA
<213> ORGANISM: Artificial Sequence
<220> FEATURE:
<223> OTHER INFORMATION: mus musculus-canis familiaris, chimeric

<400> SEQUENCE: 25

cagatccagt tggtgcagtc tggacctgag ctgaagaagc ctggagagac agtcaagatc     60

tcctgcaagg cttctgggta taccttcaca aactatggaa tgaactgggt gaagcaggct    120

ccaggaaagg gtttaaagtg gatgggctgg ataaacacct acactggaga gccaacatat    180

gctgatgact tcaagggacg gtttgccttc tctttggaaa cctctgccag cactgcctat    240

ttgcagatca acaacctcaa aaatgaggac atggctacat atttctgtgc aagacggtca    300

atttattacc cgtactgggg ccaaggcacc actctcacag tctcctcagc gagcaccacc    360

gcgccgagcg tgtttccgct ggcgccgagc tgcggcagca ccagcggcag caccgtggcg    420

ctggcgtgcc tggtgagcgg ctattttccg gaaccggtga ccgtgagctg gaacagcggc    480

agcctgacca gcggcgtgca tacctttccg agcgtgctgc agagcagcgg cctgtatagc    540

ctgagcagca tggtgaccgt gccgagcagc cgctggccga gcgaaacctt tacctgcaac    600

gtggcgcatc cggcgagcaa aaccaaagtg gataaaccgg tgccgaaacg cgaaaacggc    660

cgcgtgccgc gcccgccgga ttgcccgaaa tgcccggcgc cggaaatgct gggcggcccg    720

agcgtgttta tttttccgcc gaaaccgaaa gataccctgc tgattgcgcg caccccggaa    780

gtgacctgcg tggtggtgga tctggatccg gaagatccgg aagtgcagat tagctggttt    840

gtggatggca aacagatgca gaccgcgaaa acccagccgc gcgaagaaca gtttaacggc    900

acctatcgcg tggtgagcgt gctgccgatt ggccatcagg attggctgaa aggcaaacag    960

tttacctgca aagtgaacaa caaagcgctg ccgagcccga ttgaacgcac cattagcaaa   1020

gcgcgcggcc aggcgcatca gccgagcgtg tatgtgctgc cgccgagccg cgaagaactg   1080

agcaaaaaca ccgtgagcct gacctgcctg attaaagatt tttttccgcc ggatattgat   1140

gtggaatggc agagcaacgg ccagcaggaa ccggaaagca aatatcgcac caccccgccg   1200

cagctggatg aagatggcag ctattttctg tatagcaaac tgagcgtgga taaaagccgc   1260

tggcagcgcg gcgatacctt tatttgcgcg gtgatgcatg aagcgctgca taaccattat   1320

acccaggaaa gcctgagcca tagcccgggc aaa                                1353


<210> SEQ ID NO 26
<211> LENGTH: 451
<212> TYPE: PRT
<213> ORGANISM: Artificial Sequence
<220> FEATURE:
<223> OTHER INFORMATION: mus musculus-canis familiaris, chimeric

<400> SEQUENCE: 26

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30
```

```
Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Arg Ser Ile Tyr Tyr Pro Tyr Trp Gly Gln Gly Thr Thr Leu
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Asp Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Asn Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430
```

His Glu Ala Leu His Asn His Tyr Thr Gln Glu Ser Leu Ser His Ser
        435                 440                 445

Pro Gly Lys
    450

<210> SEQ ID NO 27
<211> LENGTH: 1353
<212> TYPE: DNA
<213> ORGANISM: Artificial Sequence
<220> FEATURE:
<223> OTHER INFORMATION: mus musculus-canis familiaris, chimeric

<400> SEQUENCE: 27
cagatccagt tggtacagtc tggacctgag ctgaagaagc ctggagagac agtcaagatc 60
tcctgcaagg cttctgggta taccttcaca acctatggag tgagctgggt gaaacaggct 120
ccaggaaagg gtttaaggtg gatgggctgg ataaacacct actctggaat gccaacatat 180
gttgatgact tcaagggacg gtttgccttc tctttggaaa cctctgccag cactgccttt 240
ttgcagatca acaacctcaa aaatgaggac acggctatat atttctgtgc aagacggggt 300
atctcctttg actactgggg ccaaggcacc actctcacag tctcctcagc gagcaccacc 360
gcgccgagcg tgtttccgct ggcgccgagc tgcggcagca ccagcggcag caccgtggcg 420
ctggcgtgcc tggtgagcgg ctattttccg gaaccggtga ccgtgagctg gaacagcggc 480
agcctgacca gcggcgtgca tacctttccg agcgtgctgc agagcagcgg cctgtatagc 540
ctgagcagca tggtgaccgt gccgagcagc cgctggccga gcgaaacctt tacctgcaac 600
gtggcgcatc cggcgagcaa aaccaaagtg gataaaccgg tgccgaaacg cgaaaacggc 660
cgcgtgccgc gcccgccgga ttgcccgaaa tgcccggcgc cggaaatgct gggcggcccg 720
agcgtgttta tttttccgcc gaaaccgaaa gataccctgc tgattgcgcg caccccggaa 780
gtgacctgcg tggtggtgga tctggatccg gaagatccgg aagtgcagat tagctggttt 840
gtggatggca aacagatgca gaccgcgaaa acccagccgc gcgaagaaca gtttaacggc 900
acctatcgcg tggtgagcgt gctgccgatt ggccatcagg attggctgaa aggcaaacag 960
tttacctgca aagtgaacaa caaagcgctg ccgagcccga ttgaacgcac cattagcaaa 1020
gcgcgcggcc aggcgcatca gccgagcgtg tatgtgctgc cgccgagccg cgaagaactg 1080
agcaaaaaca ccgtgagcct gacctgcctg attaaagatt tttttccgcc ggatattgat 1140
gtggaatggc agagcaacgg ccagcaggaa ccggaaagca aatatcgcac caccccgccg 1200
cagctggatg aagatggcag ctattttctg tatagcaaac tgagcgtgga taaaagccgc 1260
tggcagcgcg gcgatacctt tatttgcgcg gtgatgcatg aagcgctgca taaccattat 1320
acccaggaaa gcctgagcca tagcccgggc aaa 1353

<210> SEQ ID NO 28
<211> LENGTH: 451
<212> TYPE: PRT
<213> ORGANISM: Artificial Sequence
<220> FEATURE:
<223> OTHER INFORMATION: mus musculus-canis familiaris, chimeric

<400> SEQUENCE: 28

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

```
Gly Val Ser Trp Val Lys Gln Ala Pro Gly Lys Gly Leu Arg Trp Met
        35                  40                  45

Gly Trp Ile Asn Thr Tyr Ser Gly Met Pro Thr Tyr Val Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Ile Tyr Phe Cys
                85                  90                  95

Ala Arg Arg Gly Ile Ser Phe Asp Tyr Trp Gly Gln Gly Thr Thr Leu
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Asp Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Asn Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430
```

His Glu Ala Leu His Asn His Tyr Thr Gln Glu Ser Leu Ser His Ser
435 440 445

Pro Gly Lys
450

<210> SEQ ID NO 29
<211> LENGTH: 1365
<212> TYPE: DNA
<213> ORGANISM: Artificial Sequence
<220> FEATURE:
<223> OTHER INFORMATION: mus musculus-canis familiaris, chimeric

<400> SEQUENCE: 29
gaggtgaagc tggtggagtc tggaggaggc ttggtacagc ctgggggttc cctgagtctc 60
tcctgtgcaa cttctggatt caccttcagt gattactaca tgagctgggt ccgccagtct 120
ccggggaagg cacttgagtg gatgggtttt attagaaaca aagctaatgg ttacacaaca 180
gagtacagcg catctctgaa gggtcggttc accatctcca gagataattc ccaaagcatc 240
ctctatcttc aaatgaatgt cctgagagct gaggacagtg ccacttatta ctgtgtaaga 300
tttgggttaa tgtactactt tgactactgg ggccaaggca ccactctcac agtctcctca 360
gcgagcacca ccgcgccgag cgtgtttccg ctggcgccga gctgcggcag caccagcggc 420
agcaccgtgg cgctggcgtg cctggtgagc ggctattttc cggaaccggt gaccgtgagc 480
tggaacagcg gcagcctgac cagcggcgtg catacctttc cgagcgtgct gcagagcagc 540
ggcctgtata gcctgagcag catggtgacc gtgccgagca gccgctggcc gagcgaaacc 600
tttacctgca acgtggcgca tccggcgagc aaaaccaaag tggataaacc ggtgccgaaa 660
cgcgaaaacg gccgcgtgcc gcgcccgccg gattgcccga aatgcccggc gccggaaatg 720
ctgggcggcc cgagcgtgtt tatttttccg ccgaaaccga aagataccct gctgattgcg 780
cgcaccccgg aagtgacctg cgtggtggtg gatctggatc cggaagatcc ggaagtgcag 840
attagctggt ttgtggatgg caaacagatg cagaccgcga aaacccagcc gcgcgaagaa 900
cagtttaacg gcacctatcg cgtggtgagc gtgctgccga ttggccatca ggattggctg 960
aaaggcaaac agtttacctg caaagtgaac aacaaagcgc tgccgagccc gattgaacgc 1020
accattagca aagcgcgcgg ccaggcgcat cagccgagcg tgtatgtgct gccgccgagc 1080
cgcgaagaac tgagcaaaaa caccgtgagc ctgacctgcc tgattaaaga tttttttccg 1140
ccggatattg atgtggaatg gcagagcaac ggccagcagg aaccggaaag caaatatcgc 1200
accaccccgc cgcagctgga tgaagatggc agctattttc tgtatagcaa actgagcgtg 1260
gataaaagcc gctggcagcg cggcgatacc tttatttgcg cggtgatgca tgaagcgctg 1320
cataaccatt atacccagga aagcctgagc catagcccgg gcaaa 1365

<210> SEQ ID NO 30
<211> LENGTH: 455
<212> TYPE: PRT
<213> ORGANISM: Artificial Sequence
<220> FEATURE:
<223> OTHER INFORMATION: mus musculus-canis familiaris, chimeric

<400> SEQUENCE: 30

Glu Val Lys Leu Val Glu Ser Gly Gly Gly Leu Val Gln Pro Gly Gly
1 5 10 15

Ser Leu Ser Leu Ser Cys Ala Thr Ser Gly Phe Thr Phe Ser Asp Tyr
20 25 30

```
Tyr Met Ser Trp Val Arg Gln Ser Pro Gly Lys Ala Leu Glu Trp Met
        35                  40                  45

Gly Phe Ile Arg Asn Lys Ala Asn Gly Tyr Thr Thr Glu Tyr Ser Ala
    50                  55                  60

Ser Leu Lys Gly Arg Phe Thr Ile Ser Arg Asp Asn Ser Gln Ser Ile
65                  70                  75                  80

Leu Tyr Leu Gln Met Asn Val Leu Arg Ala Glu Asp Ser Ala Thr Tyr
                85                  90                  95

Tyr Cys Val Arg Phe Gly Leu Met Tyr Tyr Phe Asp Tyr Trp Gly Gln
            100                 105                 110

Gly Thr Thr Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Asn Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445
```

Leu Ser His Ser Pro Gly Lys
450 455

<210> SEQ ID NO 31
<211> LENGTH: 1353
<212> TYPE: DNA
<213> ORGANISM: Artificial Sequence
<220> FEATURE:
<223> OTHER INFORMATION: mus musculus-canis familiaris, chimeric

<400> SEQUENCE: 31
cagatccagt tggtgcagtc tggacctgag ctgaagaagc ctggagagac agtcaagatc 60
tcctgcaagg cttctgggta taccttcaca aactatggaa tgaactgggt gaagcaggct 120
ccaggaaagg gtttaaagtg gatgggctgg ataaacacct acactggaga gccaacatat 180
gctgatgact tcaagggacg gtttgccttc tctttggaaa cctctgccag cactgcctat 240
ttgcagatca acaacctcaa aaatgaggac acggctacat atttctgtgc aagaaggggg 300
acctactata ggccctgggg ccaaggcacc actctcacag tctcctcagc gagcaccacc 360
gcgccgagcg tgtttccgct ggcgccgagc tgcggcagca ccagcggcag caccgtggcg 420
ctggcgtgcc tggtgagcgg ctattttccg gaaccggtga ccgtgagctg gaacagcggc 480
agcctgacca gcggcgtgca tacctttccg agcgtgctgc agagcagcgg cctgtatagc 540
ctgagcagca tggtgaccgt gccgagcagc cgctggccga gcgaaacctt tacctgcaac 600
gtggcgcatc cggcgagcaa aaccaaagtg gataaaccgg tgccgaaacg cgaaaacggc 660
cgcgtgccgc gcccgccgga ttgcccgaaa tgcccggcgc cggaaatgct gggcggcccg 720
agcgtgttta tttttccgcc gaaaccgaaa gataccctgc tgattgcgcg caccccggaa 780
gtgacctgcg tggtggtgga tctggatccg gaagatccgg aagtgcagat tagctggttt 840
gtggatggca aacagatgca gaccgcgaaa acccagccgc gcgaagaaca gtttaacggc 900
acctatcgcg tggtgagcgt gctgccgatt ggccatcagg attggctgaa aggcaaacag 960
tttacctgca aagtgaacaa caaagcgctg ccgagcccga ttgaacgcac cattagcaaa 1020
gcgcgcggcc aggcgcatca gccgagcgtg tatgtgctgc cgccgagccg cgaagaactg 1080
agcaaaaaca ccgtgagcct gacctgcctg attaaagatt tttttccgcc ggatattgat 1140
gtggaatggc agagcaacgg ccagcaggaa ccggaaagca aatatcgcac caccccgccg 1200
cagctggatg aagatggcag ctattttctg tatagcaaac tgagcgtgga taaaagccgc 1260
tggcagcgcg gcgatacctt tatttgcgcg gtgatgcatg aagcgctgca taaccattat 1320
acccaggaaa gcctgagcca tagcccgggc aaa 1353

<210> SEQ ID NO 32
<211> LENGTH: 451
<212> TYPE: PRT
<213> ORGANISM: Artificial Sequence
<220> FEATURE:
<223> OTHER INFORMATION: mus musculus-canis familiaris, chimeric

<400> SEQUENCE: 32

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

```
Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Gly Thr Tyr Tyr Arg Pro Trp Gly Gln Gly Thr Thr Leu
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Asp Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Asn Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450
```

<210> SEQ ID NO 33
<211> LENGTH: 1353
<212> TYPE: DNA
<213> ORGANISM: Artificial Sequence
<220> FEATURE:
<223> OTHER INFORMATION: mus musculus-canis familiaris, chimeric

<400> SEQUENCE: 33
cagatccagt tggtgcagtc tggacctgag ctgaagaagc ctggagagac agtcaagatc 60
tcctgcaagg cttctggata taccttcaca aactatggaa tgaactgggt gaagcaggct 120
ccaggaaagg gtttaaagtg gatgggctgg ataaacacct acactggaga gccaacatat 180
gctgatgact tcaagggacg ggttgccttc tctttggaaa cctctgccag cactgccttt 240
ttgcagatca acaacctcaa aaatgaggac acggctacat atttctgtgc aaggcggggg 300
gtacgactgg actactgggg ccaaggcacc actctcacag tctcctcagc gagcaccacc 360
gcgccgagcg tgtttccgct ggcgccgagc tgcggcagca ccagcggcag caccgtggcg 420
ctggcgtgcc tggtgagcgg ctattttccg gaaccggtga ccgtgagctg gaacagcggc 480
agcctgacca gcggcgtgca tacctttccg agcgtgctgc agagcagcgg cctgtatagc 540
ctgagcagca tggtgaccgt gccgagcagc cgctggccga gcgaaacctt tacctgcaac 600
gtggcgcatc cggcgagcaa aaccaaagtg gataaaccgg tgccgaaacg cgaaaacggc 660
cgcgtgccgc gcccgccgga ttgcccgaaa tgcccggcgc cggaaatgct gggcggcccg 720
agcgtgttta tttttccgcc gaaaccgaaa gataccctgc tgattgcgcg caccccggaa 780
gtgacctgcg tggtggtgga tctggatccg gaagatccgg aagtgcagat tagctggttt 840
gtggatggca aacagatgca gaccgcgaaa acccagccgc gcgaagaaca gtttaacggc 900
acctatcgcg tggtgagcgt gctgccgatt ggccatcagg attggctgaa aggcaaacag 960
tttacctgca aagtgaacaa caaagcgctg ccgagcccga ttgaacgcac cattagcaaa 1020
gcgcgcggcc aggcgcatca gccgagcgtg tatgtgctgc cgccgagccg cgaagaactg 1080
agcaaaaaca ccgtgagcct gacctgcctg attaaagatt tttttccgcc ggatattgat 1140
gtggaatggc agagcaacgg ccagcaggaa ccggaaagca aatatcgcac caccccgccg 1200
cagctggatg aagatggcag ctattttctg tatagcaaac tgagcgtgga taaaagccgc 1260
tggcagcgcg gcgatacctt tatttgcgcg gtgatgcatg aagcgctgca taaccattat 1320
acccaggaaa gcctgagcca tagcccgggc aaa 1353

<210> SEQ ID NO 34
<211> LENGTH: 451
<212> TYPE: PRT
<213> ORGANISM: Artificial Sequence
<220> FEATURE:
<223> OTHER INFORMATION: mus musculus-canis familiaris, chimeric

<400> SEQUENCE: 34

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Val Ala Phe Ser Leu Glu Thr Ser Ala Ser Thr Ala Phe
65                  70                  75                  80

```
Leu Gln Ile Asn Asn Leu Lys Asn Glu Asp Thr Ala Thr Tyr Phe Cys
                85                  90                  95

Ala Arg Arg Gly Val Arg Leu Asp Tyr Trp Gly Gln Gly Thr Thr Leu
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Asp Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Asn Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450
```

<210> SEQ ID NO 35
<211> LENGTH: 1368
<212> TYPE: DNA
<213> ORGANISM: Artificial Sequence
<220> FEATURE:

<223> OTHER INFORMATION: mus musculus-canis familiaris, chimeric

<400> SEQUENCE: 35
caggtccaac tgcagcagcc tgggactgaa ctggtgaagc ctggggcttc agtgaagctg 60
tcctgcaagg cctctggcta taccttcacc agctactgga tgcactgggt gaagcagagg 120
cctggacaag gccttgagtg gattggaaat atcaatccta gcaatggtgg tactaggttc 180
aatgagaagt tcaagaacaa ggccacactg actgaagaca aatcctccag cacagcctac 240
atgcagctca gtagcctgac atctgaggac tctgcggtct attattgtgc aagatcgaac 300
tacggtagtg gctgggcctg gtttgcttac tggggccaag ggactctggt cactgtctct 360
gcagcgagca ccaccgcgcc gagcgtgttt ccgctggcgc cgagctgcgg cagcaccagc 420
ggcagcaccg tggcgctggc gtgcctggtg agcggctatt ttccggaacc ggtgaccgtg 480
agctggaaca gcggcagcct gaccagcggc gtgcatacct ttccgagcgt gctgcagagc 540
agcggcctgt atagcctgag cagcatggtg accgtgccga gcagccgctg gccgagcgaa 600
acctttacct gcaacgtggc gcatccggcg agcaaaacca aagtggataa accggtgccg 660
aaacgcgaaa acggccgcgt gccgcgcccg ccggattgcc cgaaatgccc ggcgccggaa 720
atgctgggcg gcccgagcgt gtttattttt ccgccgaaac cgaaagatac cctgctgatt 780
gcgcgcaccc cggaagtgac ctgcgtggtg gtggatctgg atccggaaga tccggaagtg 840
cagattagct ggtttgtgga tggcaaacag atgcagaccg cgaaaaccca gccgcgcgaa 900
gaacagttta acggcaccta tcgcgtggtg agcgtgctgc cgattggcca tcaggattgg 960
ctgaaaggca aacagtttac ctgcaaagtg aacaacaaag cgctgccgag cccgattgaa 1020
cgcaccatta gcaaagcgcg cggccaggcg catcagccga gcgtgtatgt gctgccgccg 1080
agccgcgaag aactgagcaa aaacaccgtg agcctgacct gcctgattaa agattttttt 1140
ccgccggata ttgatgtgga atggcagagc aacggccagc aggaaccgga aagcaaatat 1200
cgcaccaccc cgccgcagct ggatgaagat ggcagctatt ttctgtatag caaactgagc 1260
gtggataaaa gccgctggca gcgcggcgat acctttattt gcgcggtgat gcatgaagcg 1320
ctgcataacc attataccca ggaaagcctg agccatagcc cgggcaaa 1368

<210> SEQ ID NO 36
<211> LENGTH: 456
<212> TYPE: PRT
<213> ORGANISM: Artificial Sequence
<220> FEATURE:
<223> OTHER INFORMATION: mus musculus-canis familiaris, chimeric

<400> SEQUENCE: 36

Gln Val Gln Leu Gln Gln Pro Gly Thr Glu Leu Val Lys Pro Gly Ala
1 5 10 15

Ser Val Lys Leu Ser Cys Lys Ala Ser Gly Tyr Thr Phe Thr Ser Tyr
20 25 30

Trp Met His Trp Val Lys Gln Arg Pro Gly Gln Gly Leu Glu Trp Ile
35 40 45

Gly Asn Ile Asn Pro Ser Asn Gly Gly Thr Arg Phe Asn Glu Lys Phe
50 55 60

Lys Asn Lys Ala Thr Leu Thr Glu Asp Lys Ser Ser Ser Thr Ala Tyr
65 70 75 80

Met Gln Leu Ser Ser Leu Thr Ser Glu Asp Ser Ala Val Tyr Tyr Cys
85 90 95

```
Ala Arg Ser Asn Tyr Gly Ser Gly Trp Ala Trp Phe Ala Tyr Trp Gly
            100                 105                 110

Gln Gly Thr Leu Val Thr Val Ser Ala Ala Ser Thr Thr Ala Pro Ser
        115                 120                 125

Val Phe Pro Leu Ala Pro Ser Cys Gly Ser Thr Ser Gly Ser Thr Val
    130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu Tyr Ser Leu Ser Ser Met Val Thr Val
            180                 185                 190

Pro Ser Ser Arg Trp Pro Ser Glu Thr Phe Thr Cys Asn Val Ala His
        195                 200                 205

Pro Ala Ser Lys Thr Lys Val Asp Lys Pro Val Pro Lys Arg Glu Asn
    210                 215                 220

Gly Arg Val Pro Arg Pro Pro Asp Cys Pro Lys Cys Pro Ala Pro Glu
225                 230                 235                 240

Met Leu Gly Gly Pro Ser Val Phe Ile Phe Pro Pro Lys Pro Lys Asp
                245                 250                 255

Thr Leu Leu Ile Ala Arg Thr Pro Glu Val Thr Cys Val Val Val Asp
            260                 265                 270

Leu Asp Pro Glu Asp Pro Glu Val Gln Ile Ser Trp Phe Val Asp Gly
        275                 280                 285

Lys Gln Met Gln Thr Ala Lys Thr Gln Pro Arg Glu Glu Gln Phe Asn
    290                 295                 300

Gly Thr Tyr Arg Val Val Ser Val Leu Pro Ile Gly His Gln Asp Trp
305                 310                 315                 320

Leu Lys Gly Lys Gln Phe Thr Cys Lys Val Asn Asn Lys Ala Leu Pro
                325                 330                 335

Ser Pro Ile Glu Arg Thr Ile Ser Lys Ala Arg Gly Gln Ala His Gln
            340                 345                 350

Pro Ser Val Tyr Val Leu Pro Pro Ser Arg Glu Glu Leu Ser Lys Asn
        355                 360                 365

Thr Val Ser Leu Thr Cys Leu Ile Lys Asp Phe Phe Pro Pro Asp Ile
    370                 375                 380

Asp Val Glu Trp Gln Ser Asn Gly Gln Gln Glu Pro Glu Ser Lys Tyr
385                 390                 395                 400

Arg Thr Thr Pro Pro Gln Leu Asp Glu Asp Gly Ser Tyr Phe Leu Tyr
                405                 410                 415

Ser Lys Leu Ser Val Asp Lys Ser Arg Trp Gln Arg Gly Asp Thr Phe
            420                 425                 430

Ile Cys Ala Val Met His Glu Ala Leu His Asn His Tyr Thr Gln Glu
        435                 440                 445

Ser Leu Ser His Ser Pro Gly Lys
    450                 455
```

<210> SEQ ID NO 37
<211> LENGTH: 669
<212> TYPE: DNA
<213> ORGANISM: Artificial Sequence
<220> FEATURE:
<223> OTHER INFORMATION: mus musculus-canis familiaris, chimeric

<400> SEQUENCE: 37

```
gatgttttga tgacccaaac tccactctcc ctgcctgtca gtcttggaga tcaagcctcc     60

atctcttgca gatctagtca gagcattgta tatagtaatg gaaacaccta tttagaatgg    120

tacctgcaga aaccaggcca gtctccaaag ctcctgatct acaaagtttc caaccgattt    180

tctggggtcc cagacaggtt cagtggcagt ggatcaggga cagatttcac actcaagatc    240

agcagagtgg aggctgagga tctgggagtt tattactgct ttcaaggttc acatgttccg    300

tggacgttcg gtggaggcac caagctggaa atcaaacgca acgatgcgca gccggcggtg    360

tatctgtttc agccgagccc ggatcagctg cataccggca gcgcgagcgt ggtgtgcctg    420

ctgaacagct tttatccgaa agatattaac gtgaaatgga aagtggatgg cgtgattcag    480

gataccggca ttcaggaaag cgtgaccgaa caggatagca aagatagcac ctatagcctg    540

agcagcaccc tgaccatgag cagcaccgaa tatctgagcc atgaactgta tagctgcgaa    600

attacccata aaagcctgcc gagcaccctg attaaaagct ttcagcgcag cgaatgccag    660

cgcgtggat                                                            669
```

<210> SEQ ID NO 38
<211> LENGTH: 223
<212> TYPE: PRT
<213> ORGANISM: Artificial Sequence
<220> FEATURE:
<223> OTHER INFORMATION: mus musculus-canis familiaris, chimeric

<400> SEQUENCE: 38

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

<210> SEQ ID NO 39
<211> LENGTH: 669
<212> TYPE: DNA
<213> ORGANISM: Artificial Sequence
<220> FEATURE:
<223> OTHER INFORMATION: mus musculus-canis familiaris, chimeric

<400> SEQUENCE: 39
gatgttttga tgacccagac tccactctcc ctgcctgtca gtcttggaga tcacgcctcc 60
atctcttgca aatctagtca gagcattgta tatattaatg gaaacaccta tttagaatgg 120
tacctgcaga agccaggcca gtctccaaag ctcctgatct acaaagtttc caaacgattt 180
tctggggtcc cagacaggtt cagtggcagt ggatcaggga cagatttcac actcaagatc 240
agcagagtgg aggctgagga tctgggagtt tattactgct ttcaaggttc acatgttccg 300
tggacgttcg gtggaggcac caagctggaa atcaaacgca acgatgcgca gccggcggtg 360
tatctgtttc agccgagccc ggatcagctg cataccggca gcgcgagcgt ggtgtgcctg 420
ctgaacagct tttatccgaa agatattaac gtgaaatgga aagtggatgg cgtgattcag 480
gataccggca ttcaggaaag cgtgaccgaa caggatagca aagatagcac ctatagcctg 540
agcagcaccc tgaccatgag cagcaccgaa tatctgagcc atgaactgta tagctgcgaa 600
attacccata aaagcctgcc gagcaccctg attaaaagct ttcagcgcag cgaatgccag 660
cgcgtggat 669

<210> SEQ ID NO 40
<211> LENGTH: 223
<212> TYPE: PRT
<213> ORGANISM: Artificial Sequence
<220> FEATURE:
<223> OTHER INFORMATION: mus musculus-canis familiaris, chimeric

<400> SEQUENCE: 40

Asp Val Leu Met Thr Gln Thr Pro Leu Ser Leu Pro Val Ser Leu Gly
1 5 10 15

Asp His Ala Ser Ile Ser Cys Lys Ser Ser Gln Ser Ile Val Tyr Ile
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Lys Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Trp Thr Phe Gly Gly Gly Thr Lys Leu Glu Ile Lys
100 105 110

Arg Asn Asp Ala Gln Pro Ala Val Tyr Leu Phe Gln Pro Ser Pro Asp
115 120 125

Gln Leu His Thr Gly Ser Ala Ser Val Val Cys Leu Leu Asn Ser Phe
130 135 140

Tyr Pro Lys Asp Ile Asn Val Lys Trp Lys Val Asp Gly Val Ile Gln
145 150 155 160

Asp Thr Gly Ile Gln Glu Ser Val Thr Glu Gln Asp Ser Lys Asp Ser
165 170 175

Thr Tyr Ser Leu Ser Ser Thr Leu Thr Met Ser Ser Thr Glu Tyr Leu
180 185 190

Ser His Glu Leu Tyr Ser Cys Glu Ile Thr His Lys Ser Leu Pro Ser
195 200 205

Thr Leu Ile Lys Ser Phe Gln Arg Ser Glu Cys Gln Arg Val Asp
210 215 220

<210> SEQ ID NO 41
<211> LENGTH: 657
<212> TYPE: DNA
<213> ORGANISM: Artificial Sequence
<220> FEATURE:
<223> OTHER INFORMATION: mus musculus-canis familiaris, chimeric

<400> SEQUENCE: 41
gaaaatgtgc tcatccagtc tccagcaatc atgtctgctt ctccagggga aaaggtcacc 60
atgacctgca gggccagctc aagtgtaagt tccagttact tgcactggta ccagcagaag 120
tcaggtgcct cccccaaact ctggattttt agcacatcca acttggcttc tggagtccct 180
gctcgcttca gtggcagtgg gtctgggacc tcttattctc tcacaatcaa cagtgtggag 240
gctgaagatg ctgccactta ttactgccag cagtacagtg gtctcccact cacgttcgga 300
ggggggacca agctggaaat aaaacgcaac gatgcgcagc cggcggtgta tctgtttcag 360
ccgagcccgg atcagctgca taccggcagc gcgagcgtgg tgtgcctgct gaacagcttt 420
tatccgaaag atattaacgt gaaatggaaa gtggatggcg tgattcagga taccggcatt 480
caggaaagcg tgaccgaaca ggatagcaaa gatagcacct atagcctgag cagcaccctg 540
accatgagca gcaccgaata tctgagccat gaactgtata gctgcgaaat tacccataaa 600
agcctgccga gcaccctgat taaaagcttt cagcgcagcg aatgccagcg cgtggat 657

<210> SEQ ID NO 42
<211> LENGTH: 219
<212> TYPE: PRT
<213> ORGANISM: Artificial Sequence
<220> FEATURE:
<223> OTHER INFORMATION: mus musculus-canis familiaris, chimeric

<400> SEQUENCE: 42

Glu Asn Val Leu Ile Gln Ser Pro Ala Ile Met Ser Ala Ser Pro Gly
1 5 10 15

Glu Lys Val Thr Met Thr Cys Arg Ala Ser Ser Ser Val Ser Ser Ser
20 25 30

Tyr Leu His Trp Tyr Gln Gln Lys Ser Gly Ala Ser Pro Lys Leu Trp
35 40 45

Ile Phe Ser Thr Ser Asn Leu Ala Ser Gly Val Pro Ala Arg Phe Ser
50 55 60

Gly Ser Gly Ser Gly Thr Ser Tyr Ser Leu Thr Ile Asn Ser Val Glu
65 70 75 80

Ala Glu Asp Ala Ala Thr Tyr Tyr Cys Gln Gln Tyr Ser Gly Leu Pro
85 90 95

Leu Thr Phe Gly Gly Gly Thr Lys Leu Glu Ile Lys Arg Asn Asp Ala
100 105 110

Gln Pro Ala Val Tyr Leu Phe Gln Pro Ser Pro Asp Gln Leu His Thr
115 120 125

Gly Ser Ala Ser Val Val Cys Leu Leu Asn Ser Phe Tyr Pro Lys Asp
130 135 140

Ile Asn Val Lys Trp Lys Val Asp Gly Val Ile Gln Asp Thr Gly Ile
145 150 155 160

```
Gln Glu Ser Val Thr Glu Gln Asp Ser Lys Asp Ser Thr Tyr Ser Leu
                165                 170                 175

Ser Ser Thr Leu Thr Met Ser Ser Thr Glu Tyr Leu Ser His Glu Leu
            180                 185                 190

Tyr Ser Cys Glu Ile Thr His Lys Ser Leu Pro Ser Thr Leu Ile Lys
        195                 200                 205

Ser Phe Gln Arg Ser Glu Cys Gln Arg Val Asp
    210                 215


<210> SEQ ID NO 43
<211> LENGTH: 669
<212> TYPE: DNA
<213> ORGANISM: Artificial Sequence
<220> FEATURE:
<223> OTHER INFORMATION: mus musculus-canis familiaris, chimeric

<400> SEQUENCE: 43

gatgttttga tgacccaaac tccactctcc ctgcctgtca gtcttggaga tcaagcctcc      60

atctcttgca gatctagtca gagtattgta tatagtcatg gaaacaccta tttagaatgg     120

tacctgcaga aaccaggcca gtctccaaag gtcctgatct acaaagtttc caaccgattt     180

tctggggtcc cagacaggtt cagtggcagt ggatcaggga cagatttcac actcaagatc     240

agcagagtgg aggctgagga tctgggagtt tattactgct ttcaaggttc acatgttccg     300

tggacgttcg gtggaggcac caagctggaa atcaaacgca acgatgcgca gccggcggtg     360

tatctgtttc agccgagccc ggatcagctg cataccggca gcgcgagcgt ggtgtgcctg     420

ctgaacagct tttatccgaa agatattaac gtgaaatgga aagtggatgg cgtgattcag     480

gataccggca ttcaggaaag cgtgaccgaa caggatagca aagatagcac ctatagcctg     540

agcagcaccc tgaccatgag cagcaccgaa tatctgagcc atgaactgta tagctgcgaa     600

attacccata aaagcctgcc gagcaccctg attaaaagct ttcagcgcag cgaatgccag     660

cgcgtggat                                                             669


<210> SEQ ID NO 44
<211> LENGTH: 223
<212> TYPE: PRT
<213> ORGANISM: Artificial Sequence
<220> FEATURE:
<223> OTHER INFORMATION: mus musculus-canis familiaris, chimeric

<400> SEQUENCE: 44

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

His Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Asn Asp Ala Gln Pro Ala Val Tyr Leu Phe Gln Pro Ser Pro Asp
        115                 120                 125
```

```
Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220


<210> SEQ ID NO 45
<211> LENGTH: 669
<212> TYPE: DNA
<213> ORGANISM: Artificial Sequence
<220> FEATURE:
<223> OTHER INFORMATION: mus musculus-canis familiaris, chimeric

<400> SEQUENCE: 45

gatgttttga tgacccaaac tccactctcc ctgcctgtca gtcttggaga tcaagcctcc      60

atctcttgca gatctagtca gagcattgta tatattagtg gaagcaccta tttagaatgg     120

tatctgcaga aaccaggcca gtctccaaag ctcctgatct acaaagtttc cagtcgattt     180

tctggggtcc cagacaggtt cagtggcagt ggatcaggga cagatttcac actcaagatc     240

agcagagtgg aggctgagga tctgggagtt tattactgct ttcaaggttc acatgttccg     300

tggacgttcg gtggaggcac caagctggaa atcaaacgca acgatgcgca gccggcggtg     360

tatctgtttc agccgagccc ggatcagctg cataccggca gcgcgagcgt ggtgtgcctg     420

ctgaacagct tttatccgaa agatattaac gtgaaatgga aagtggatgg cgtgattcag     480

gataccggca ttcaggaaag cgtgaccgaa caggatagca aagatagcac ctatagcctg     540

agcagcaccc tgaccatgag cagcaccgaa tatctgagcc atgaactgta tagctgcgaa     600

attacccata aaagcctgcc gagcaccctg attaaaagct ttcagcgcag cgaatgccag     660

cgcgtggat                                                             669


<210> SEQ ID NO 46
<211> LENGTH: 223
<212> TYPE: PRT
<213> ORGANISM: Artificial Sequence
<220> FEATURE:
<223> OTHER INFORMATION: mus musculus-canis familiaris, chimeric

<400> SEQUENCE: 46

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ile
            20                  25                  30

Ser Gly Ser Thr Tyr Leu Glu Trp Tyr Leu Gln Lys Pro Gly Gln Ser
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220


<210> SEQ ID NO 47
<211> LENGTH: 654
<212> TYPE: DNA
<213> ORGANISM: Artificial Sequence
<220> FEATURE:
<223> OTHER INFORMATION: mus musculus-canis familiaris, chimeric

<400> SEQUENCE: 47

gacatccaga tgaaccagtc tccatccagt ctgtctgcat cccttggaga cacaattacc      60

atcacttgcc atgccagtca gaacattaat gtttggttaa gctggtacca gcagaaacca     120

ggaaatattc ctaaactttt gatctataag tcttccaact tgcacacagg cgtcccatca     180

aggtttagtg gcagtggatc tggaacaggt ttcacattaa ccatcagcag cctgcagcct     240

gaagacattg ccacttacta ctgtcaacag ggtcaaagtt atccgtggac gttcggtgga     300

ggcaccaagc tggaaatcaa acgcaacgat gcgcagccgg cggtgtatct gtttcagccg     360

agcccggatc agctgcatac cggcagcgcg agcgtggtgt gcctgctgaa cagcttttat     420

ccgaaagata ttaacgtgaa atggaaagtg gatggcgtga ttcaggatac cggcattcag     480

gaaagcgtga ccgaacagga tagcaaagat agcacctata gcctgagcag caccctgacc     540

atgagcagca ccgaatatct gagccatgaa ctgtatagct gcgaaattac ccataaaagc     600

ctgccgagca ccctgattaa aagctttcag cgcagcgaat gccagcgcgt ggat           654


<210> SEQ ID NO 48
<211> LENGTH: 218
<212> TYPE: PRT
<213> ORGANISM: Artificial Sequence
<220> FEATURE:
<223> OTHER INFORMATION: mus musculus-canis familiaris, chimeric

<400> SEQUENCE: 48

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45
```

```
Tyr Lys Ser Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Ser Lys Asp Ser Thr Tyr Ser Leu Ser
                165                 170                 175

Ser Thr Leu Thr Met Ser Ser Thr Glu Tyr Leu Ser His Glu Leu Tyr
            180                 185                 190

Ser Cys Glu Ile Thr His Lys Ser Leu Pro Ser Thr Leu Ile Lys Ser
        195                 200                 205

Phe Gln Arg Ser Glu Cys Gln Arg Val Asp
    210                 215
```

<210> SEQ ID NO 49
<211> LENGTH: 669
<212> TYPE: DNA
<213> ORGANISM: Artificial Sequence
<220> FEATURE:
<223> OTHER INFORMATION: caninized mus musculus

<400> SEQUENCE: 49

```
gatattgtga tgacccagac cccgctgagc ctgagcgtga gcccgggcga accggcgagc      60

attagctgcc gcagcagcca gagcattgtg tatagcaacg gcaacaccta tctggaatgg     120

tttcagcaga aaccgggcca gagcccgcag cgcctgattt ataaagtgag caaccgcttt     180

agcggcgtgc cggatcgctt tagcggcagc ggcagcggca ccgattttac cctgcgcatt     240

agccgcgtgg aagcggatga tgcgggcgtg tattattgct ttcagggcag ccatgtgccg     300

tggacctttg gcggcggcac caaactggaa attaaaagga acgacgctca gccagccgtg     360

tacctcttcc agccttcgcc ggaccagctt catacggggt cagcgtcggt ggtgtgcctg     420

ttgaactcgt tttaccccaa ggacattaac gtgaagtgga aggtagacgg ggtaattcaa     480

gacactggca ttcaagagtc cgtcacggaa caagactcaa aagactcaac gtattcactg     540

tcgtcaacct tgacgatgtc aagcaccgag tatcttagcc atgagctgta ttcgtgcgag     600

atcacccaca agtccctccc ctccactctt atcaaatcct ttcagcggtc ggaatgtcag     660

cgggtcgat                                                             669
```

<210> SEQ ID NO 50
<211> LENGTH: 223
<212> TYPE: PRT
<213> ORGANISM: Artificial Sequence
<220> FEATURE:
<223> OTHER INFORMATION: caninized mus musculus

<400> SEQUENCE: 50

```
Asp Ile Val Met Thr Gln Thr Pro Leu Ser Leu Ser Val Ser Pro Gly
1               5                   10                  15
```

```
Glu Pro Ala Ser Ile Ser Cys Arg Ser Ser Gln Ser Ile Val Tyr Ser
            20                  25                  30

Asn Gly Asn Thr Tyr Leu Glu Trp Phe Gln Gln Lys Pro Gly Gln Ser
        35                  40                  45

Pro Gln Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Ala Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

<210> SEQ ID NO 51
<211> LENGTH: 669
<212> TYPE: DNA
<213> ORGANISM: Artificial Sequence
<220> FEATURE:
<223> OTHER INFORMATION: caninized mus musculus

<400> SEQUENCE: 51

```
gatattgtga tgacccagac cccgctgagc ctgagcgtga gcccgggcga accggcgagc     60

attagctgcc gcagcagcca gagcattgtg tatagcaacg gcaacaccta tctggaatgg    120

tatcagcaga aaccgggcca gagcccgaaa ctgctgattt ataaagtgag caaccgcttt    180

agcggcgtgc cggatcgctt tagcggcagc ggcagcggca ccgattttac cctgcgcatt    240

agccgcgtgg aagcggatga tgcgggcgtg tattattgct ttcagggcag ccatgtgccg    300

tggacctttg gcggcggcac caaactggaa attaaaagga acgacgctca gccagccgtg    360

tacctcttcc agccttcgcc ggaccagctt catacggggt cagcgtcggt ggtgtgcctg    420

ttgaactcgt tttaccccaa ggacattaac gtgaagtgga aggtagacgg ggtaattcaa    480

gacactggca ttcaagagtc cgtcacggaa caagactcaa aagactcaac gtattcactg    540

tcgtcaacct tgacgatgtc aagcaccgag tatcttagcc atgagctgta ttcgtgcgag    600

atcacccaca agtccctccc ctccactctt atcaaatcct ttcagcggtc ggaatgtcag    660

cgggtcgat                                                           669
```

<210> SEQ ID NO 52
<211> LENGTH: 223
<212> TYPE: PRT
<213> ORGANISM: Artificial Sequence
<220> FEATURE:
<223> OTHER INFORMATION: caninized mus musculus

<400> SEQUENCE: 52

```
Asp Ile Val Met Thr Gln Thr Pro Leu Ser Leu Ser Val Ser Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Glu Trp Tyr Gln Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Ala Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

<210> SEQ ID NO 53
<211> LENGTH: 669
<212> TYPE: DNA
<213> ORGANISM: Artificial Sequence
<220> FEATURE:
<223> OTHER INFORMATION: caninized mus musculus

<400> SEQUENCE: 53

```
gatgtgctga tgacccagac cccgctgagc ctgagcgtga gcccgggcga accggcgagc     60

attagctgcc gcagcagcca gagcattgtg tatagcaacg gcaacaccta tctggaatgg    120

tatctgcaga aaccgggcca gagcccgaaa ctgctgattt ataaagtgag caaccgcttt    180

agcggcgtgc cggatcgctt tagcggcagc ggcagcggca ccgattttac cctgcgcatt    240

agccgcgtgg aagcggatga tgcgggcgtg tattattgct ttcagggcag ccatgtgccg    300

tggacctttg gcggcggcac caaactggaa ctgaaaagga acgacgctca gccagccgtg    360

tacctcttcc agccttcgcc ggaccagctt catacggggt cagcgtcggt ggtgtgcctg    420

ttgaactcgt tttaccccaa ggacattaac gtgaagtgga aggtagacgg ggtaattcaa    480

gacactggca ttcaagagtc cgtcacggaa caagactcaa aagactcaac gtattcactg    540

tcgtcaacct tgacgatgtc aagcaccgag tatcttagcc atgagctgta ttcgtgcgag    600
```

atcacccaca agtccctccc ctccactctt atcaaatcct ttcagcggtc ggaatgtcag 660
cgggtcgat 669

<210> SEQ ID NO 54
<211> LENGTH: 223
<212> TYPE: PRT
<213> ORGANISM: Artificial Sequence
<220> FEATURE:
<223> OTHER INFORMATION: caninized mus musculus

<400> SEQUENCE: 54

Asp Val Leu Met Thr Gln Thr Pro Leu Ser Leu Ser Val Ser Pro Gly
1 5 10 15

Glu Pro Ala Ser Ile Ser Cys Arg Ser Ser Gln Ser Ile Val Tyr Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Arg Ile
65 70 75 80

Ser Arg Val Glu Ala Asp Asp Ala Gly Val Tyr Tyr Cys Phe Gln Gly
85 90 95

Ser His Val Pro Trp Thr Phe Gly Gly Gly Thr Lys Leu Glu Leu Lys
100 105 110

Arg Asn Asp Ala Gln Pro Ala Val Tyr Leu Phe Gln Pro Ser Pro Asp
115 120 125

Gln Leu His Thr Gly Ser Ala Ser Val Val Cys Leu Leu Asn Ser Phe
130 135 140

Tyr Pro Lys Asp Ile Asn Val Lys Trp Lys Val Asp Gly Val Ile Gln
145 150 155 160

Asp Thr Gly Ile Gln Glu Ser Val Thr Glu Gln Asp Ser Lys Asp Ser
165 170 175

Thr Tyr Ser Leu Ser Ser Thr Leu Thr Met Ser Ser Thr Glu Tyr Leu
180 185 190

Ser His Glu Leu Tyr Ser Cys Glu Ile Thr His Lys Ser Leu Pro Ser
195 200 205

Thr Leu Ile Lys Ser Phe Gln Arg Ser Glu Cys Gln Arg Val Asp
210 215 220

<210> SEQ ID NO 55
<211> LENGTH: 657
<212> TYPE: DNA
<213> ORGANISM: Artificial Sequence
<220> FEATURE:
<223> OTHER INFORMATION: caninized mus musculus

<400> SEQUENCE: 55
gaaattgtga tgacccagag cccggcgagc ctgagcctga gccaggaaga aaaagtgacc 60
attacctgcc gcgcgagcag cagcgtgagc agcagctatc tgcattggta tcagcagaaa 120
ccgggccagg cgccgaaact gctgatttat agcaccagca acctggcgag cggcgtgccg 180
agccgcttta gcggcagcgg cagcggcacc gattttagct ttaccattag cagcctggaa 240
ccggaagatg tggcggtgta ttattgccag cagtatagcg gcctgccgct gacctttggc 300
ggcggcacca aactggaaat taaaaggaac gacgctcagc cagccgtgta cctcttccag 360
ccttcgccgg accagcttca tacggggtca gcgtcggtgg tgtgcctgtt gaactcgttt 420
taccccaagg acattaacgt gaagtggaag gtagacgggg taattcaaga cactggcatt 480
caagagtccg tcacggaaca agactcaaaa gactcaacgt attcactgtc gtcaaccttg 540
acgatgtcaa gcaccgagta tcttagccat gagctgtatt cgtgcgagat cacccacaag 600
tccctcccct ccactcttat caaatccttt cagcggtcgg aatgtcagcg ggtcgat 657

<210> SEQ ID NO 56
<211> LENGTH: 219
<212> TYPE: PRT
<213> ORGANISM: Artificial Sequence
<220> FEATURE:
<223> OTHER INFORMATION: caninized mus musculus

<400> SEQUENCE: 56

Glu Ile Val Met Thr Gln Ser Pro Ala Ser Leu Ser Leu Ser Gln Glu
1 5 10 15

Glu Lys Val Thr Ile Thr Cys Arg Ala Ser Ser Ser Val Ser Ser Ser
20 25 30

Tyr Leu His Trp Tyr Gln Gln Lys Pro Gly Gln Ala Pro Lys Leu Leu
35 40 45

Ile Tyr Ser Thr Ser Asn Leu Ala Ser Gly Val Pro Ser Arg Phe Ser
50 55 60

Gly Ser Gly Ser Gly Thr Asp Phe Ser Phe Thr Ile Ser Ser Leu Glu
65 70 75 80

Pro Glu Asp Val Ala Val Tyr Tyr Cys Gln Gln Tyr Ser Gly Leu Pro
85 90 95

Leu Thr Phe Gly Gly Gly Thr Lys Leu Glu Ile Lys Arg Asn Asp Ala
100 105 110

Gln Pro Ala Val Tyr Leu Phe Gln Pro Ser Pro Asp Gln Leu His Thr
115 120 125

Gly Ser Ala Ser Val Val Cys Leu Leu Asn Ser Phe Tyr Pro Lys Asp
130 135 140

Ile Asn Val Lys Trp Lys Val Asp Gly Val Ile Gln Asp Thr Gly Ile
145 150 155 160

Gln Glu Ser Val Thr Glu Gln Asp Ser Lys Asp Ser Thr Tyr Ser Leu
165 170 175

Ser Ser Thr Leu Thr Met Ser Ser Thr Glu Tyr Leu Ser His Glu Leu
180 185 190

Tyr Ser Cys Glu Ile Thr His Lys Ser Leu Pro Ser Thr Leu Ile Lys
195 200 205

Ser Phe Gln Arg Ser Glu Cys Gln Arg Val Asp
210 215

<210> SEQ ID NO 57
<211> LENGTH: 657
<212> TYPE: DNA
<213> ORGANISM: Artificial Sequence
<220> FEATURE:
<223> OTHER INFORMATION: caninized mus musculus

<400> SEQUENCE: 57
gaaaacgtgc tgacccagag cccggcgagc ctgagcctga gccaggaaga aaaagtgacc 60
attacctgcc gcgcgagcag cagcgtgagc agcagctatc tgcattggta tcagcagaaa 120
ccgggccagg cgccgaaact gtggattttt agcaccagca acctggcgag cggcgtgccg 180
agccgcttta gcggcagcgg cagcggcacc gattatagct ttaccattag cagcctggaa 240

```
ccggaagatg tggcggtgta ttattgccag cagtatagcg gcctgccgct gacctttggc    300

ggcggcacca aactggaact gaaaaggaac gacgctcagc cagccgtgta cctcttccag    360

ccttcgccgg accagcttca tacggggtca gcgtcggtgg tgtgcctgtt gaactcgttt    420

taccccaagg acattaacgt gaagtggaag gtagacgggg taattcaaga cactggcatt    480

caagagtccg tcacggaaca agactcaaaa gactcaacgt attcactgtc gtcaaccttg    540

acgatgtcaa gcaccgagta tcttagccat gagctgtatt cgtgcgagat cacccacaag    600

tccctcccct ccactcttat caaatccttt cagcggtcgg aatgtcagcg ggtcgat       657
```

<210> SEQ ID NO 58
<211> LENGTH: 219
<212> TYPE: PRT
<213> ORGANISM: Artificial Sequence
<220> FEATURE:
<223> OTHER INFORMATION: caninized mus musculus

<400> SEQUENCE: 58

```
Glu Asn Val Leu Thr Gln Ser Pro Ala Ser Leu Ser Leu Ser Gln Glu
1               5                   10                  15

Glu Lys Val Thr Ile Thr Cys Arg Ala Ser Ser Ser Val Ser Ser Ser
            20                  25                  30

Tyr Leu His Trp Tyr Gln Gln Lys Pro Gly Gln Ala Pro Lys Leu Trp
        35                  40                  45

Ile Phe Ser Thr Ser Asn Leu Ala Ser Gly Val Pro Ser Arg Phe Ser
    50                  55                  60

Gly Ser Gly Ser Gly Thr Asp Tyr Ser Phe Thr Ile Ser Ser Leu Glu
65                  70                  75                  80

Pro Glu Asp Val Ala Val Tyr Tyr Cys Gln Gln Tyr Ser Gly Leu Pro
                85                  90                  95

Leu Thr Phe Gly Gly Gly Thr Lys Leu Glu Leu Lys Arg Asn Asp Ala
            100                 105                 110

Gln Pro Ala Val Tyr Leu Phe Gln Pro Ser Pro Asp Gln Leu His Thr
        115                 120                 125

Gly Ser Ala Ser Val Val Cys Leu Leu Asn Ser Phe Tyr Pro Lys Asp
    130                 135                 140

Ile Asn Val Lys Trp Lys Val Asp Gly Val Ile Gln Asp Thr Gly Ile
145                 150                 155                 160

Gln Glu Ser Val Thr Glu Gln Asp Ser Lys Asp Ser Thr Tyr Ser Leu
                165                 170                 175

Ser Ser Thr Leu Thr Met Ser Ser Thr Glu Tyr Leu Ser His Glu Leu
            180                 185                 190

Tyr Ser Cys Glu Ile Thr His Lys Ser Leu Pro Ser Thr Leu Ile Lys
        195                 200                 205

Ser Phe Gln Arg Ser Glu Cys Gln Arg Val Asp
    210                 215
```

<210> SEQ ID NO 59
<211> LENGTH: 657
<212> TYPE: DNA
<213> ORGANISM: Artificial Sequence
<220> FEATURE:
<223> OTHER INFORMATION: caninized mus musculus

<400> SEQUENCE: 59

```
gaaaacgtgc tgacccagag cccggcgagc ctgagcctga gcccgggcga aaaagtgacc     60
attacctgcc gcgcgagcag cagcgtgagc agcagctatc tgcattggta tcagcagaaa    120
ccgggccaga gcccgaaact gtggattttt agcaccagca acctggcgag cggcgtgccg    180
agccgcttta gcggcagcgg cagcggcacc agctatagct ttaccattag cagcctggaa    240
ccggaagatg tggcggtgta ttattgccag cagtatagcg gcctgccgct gacctttggc    300
ggcggcacca aactggaact gaaaaggaac gacgctcagc cagccgtgta cctcttccag    360
ccttcgccgg accagcttca tacggggtca gcgtcggtgg tgtgcctgtt gaactcgttt    420
taccccaagg acattaacgt gaagtggaag gtagacgggg taattcaaga cactggcatt    480
caagagtccg tcacggaaca agactcaaaa gactcaacgt attcactgtc gtcaaccttg    540
acgatgtcaa gcaccgagta tcttagccat gagctgtatt cgtgcgagat cacccacaag    600
tccctcccct ccactcttat caaatccttt cagcggtcgg aatgtcagcg ggtcgat       657
```

<210> SEQ ID NO 60
<211> LENGTH: 219
<212> TYPE: PRT
<213> ORGANISM: Artificial Sequence
<220> FEATURE:
<223> OTHER INFORMATION: caninized mus musculus

<400> SEQUENCE: 60

```
Glu Asn Val Leu Thr Gln Ser Pro Ala Ser Leu Ser Leu Ser Pro Gly
1               5                   10                  15

Glu Lys Val Thr Ile Thr Cys Arg Ala Ser Ser Ser Val Ser Ser Ser
            20                  25                  30

Tyr Leu His Trp Tyr Gln Gln Lys Pro Gly Gln Ser Pro Lys Leu Trp
        35                  40                  45

Ile Phe Ser Thr Ser Asn Leu Ala Ser Gly Val Pro Ser Arg Phe Ser
    50                  55                  60

Gly Ser Gly Ser Gly Thr Ser Tyr Ser Phe Thr Ile Ser Ser Leu Glu
65                  70                  75                  80

Pro Glu Asp Val Ala Val Tyr Tyr Cys Gln Gln Tyr Ser Gly Leu Pro
                85                  90                  95

Leu Thr Phe Gly Gly Gly Thr Lys Leu Glu Leu Lys Arg Asn Asp Ala
            100                 105                 110

Gln Pro Ala Val Tyr Leu Phe Gln Pro Ser Pro Asp Gln Leu His Thr
        115                 120                 125

Gly Ser Ala Ser Val Val Cys Leu Leu Asn Ser Phe Tyr Pro Lys Asp
    130                 135                 140

Ile Asn Val Lys Trp Lys Val Asp Gly Val Ile Gln Asp Thr Gly Ile
145                 150                 155                 160

Gln Glu Ser Val Thr Glu Gln Asp Ser Lys Asp Ser Thr Tyr Ser Leu
                165                 170                 175

Ser Ser Thr Leu Thr Met Ser Ser Thr Glu Tyr Leu Ser His Glu Leu
            180                 185                 190

Tyr Ser Cys Glu Ile Thr His Lys Ser Leu Pro Ser Thr Leu Ile Lys
        195                 200                 205

Ser Phe Gln Arg Ser Glu Cys Gln Arg Val Asp
    210                 215
```

<210> SEQ ID NO 61

<211> LENGTH: 1353
<212> TYPE: DNA
<213> ORGANISM: Artificial Sequence
<220> FEATURE:
<223> OTHER INFORMATION: caninized mus musculus

<400> SEQUENCE: 61

```
gaagtgcagc tggtggaaag cggcggcgat ctggtgaaac cgggcggcag cctgcgcctg     60
agctgcgtgg cgagcggcta tacctttacc aactatggca tgaactgggt gcgccaggcg    120
ccgggcaaag gcctgcagtg ggtggcgtgg attaacacct ataccggcga accgacctat    180
gcggatgatt ttaaaggccg ctttaccatt agccgcgata acgcgaaaaa caccctgtat    240
ctgcagatga acagcctgcg cgcggaagat accgcggtgt attattgcgc gcgccgcagc    300
atttattatc cgtattgggg ccagggcacc accctgaccg tgagcagcgc ttccacaacc    360
gcgccatcag tctttccgtt ggccccatca tgcgggtcga cgagcggatc gactgtggcc    420
ctggcgtgct tggtgtcggg atactttccc gaacccgtca cggtcagctg gaactccgga    480
tcgcttacga gcggtgtgca tacgttcccc tcggtcttgc aatcatcagg gctctactcg    540
ctgtcgagca tggtaacggt gccctcatcg aggtggccct ccgaaacgtt cacatgtaac    600
gtagcacatc cagcctccaa aaccaaggtg gataaacccg tgccgaaaag agagaatggg    660
cgggtgcctc gacccccctga ttgccccaag tgtccggctc cggaaatgct cggtggaccc    720
tcagtgttta tcttccctcc gaagcccaag gacactctgc tgatcgcgcg cactccagaa    780
gtaacatgtg tagtggtgga ccttgatccc gaggaccccg aagtccagat ctcctggttt    840
gtagatggga aacagatgca gaccgcaaaa actcaaccca gagaggagca gttcaacgga    900
acataccgag tggtatccgt ccttccgatt ggccaccagg actggttgaa agggaagcag    960
tttacgtgta aagtcaacaa taaggggttg cctagcccta ttgagcggac gatttcgaaa   1020
gctaggggac aggcccacca gccatcggtc tatgtccttc cgccttcccg cgaggagctc   1080
tcgaagaata cagtgagcct tacatgcctc attaaggatt tcttcccgcc tgatatcgac   1140
gtagagtggc aatcaaacgg tcaacaggag ccggaatcca agtatagaac cactccgccc   1200
cagcttgacg aggacggatc atactttttg tattcaaaac tgtcggtgga taagagccgg   1260
tggcagagag gtgacacctt catctgtgcg gtgatgcacg aagcactcca taatcactac   1320
acccaagaga gcctctcgca ttcccccgga aag                                 1353
```

<210> SEQ ID NO 62
<211> LENGTH: 451
<212> TYPE: PRT
<213> ORGANISM: Artificial Sequence
<220> FEATURE:
<223> OTHER INFORMATION: caninized mus musculus

<400> SEQUENCE: 62

```
Glu Val Gln Leu Val Glu Ser Gly Gly Asp Leu Val Lys Pro Gly Gly
1               5                   10                  15

Ser Leu Arg Leu Ser Cys Val Ala Ser Gly Tyr Thr Phe Thr Asn Tyr
            20                  25                  30

Gly Met Asn Trp Val Arg Gln Ala Pro Gly Lys Gly Leu Gln Trp Val
        35                  40                  45

Ala Trp Ile Asn Thr Tyr Thr Gly Glu Pro Thr Tyr Ala Asp Asp Phe
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Arg Ser Ile Tyr Tyr Pro Tyr Trp Gly Gln Gly Thr Thr Leu
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Asp Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Asn Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450
```

<210> SEQ ID NO 63
<211> LENGTH: 1353
<212> TYPE: DNA
<213> ORGANISM: Artificial Sequence
<220> FEATURE:
<223> OTHER INFORMATION: caninized mus musculus

<400> SEQUENCE: 63

```
gaaattcagc tggtgcagag cggcggcgat ctggtgaaac cgggcggcag cctgcgcctg     60
agctgcaaag cgagcggcta tacctttacc aactatggca tgaactgggt gcgccaggcg    120
ccgggcaaag gcctgcagtg gatgggctgg attaacacct ataccggcga accgacctat    180
gcggatgatt ttaaaggccg ctttaccttt agcctggata acgcgaaaaa caccctgtat    240
ctgcagatga acagcctgcg cgcggaagat accgcggtgt atttttgcgc gcgccgcagc    300
atttattatc cgtattgggg ccagggcacc accctgaccg tgagcagcgc ttccacaacc    360
gcgccatcag tctttccgtt ggccccatca tgcgggtcga cgagcggatc gactgtggcc    420
ctggcgtgct tggtgtcggg atactttccc gaacccgtca cggtcagctg gaactccgga    480
tcgcttacga gcggtgtgca tacgttcccc tcggtcttgc aatcatcagg gctctactcg    540
ctgtcgagca tggtaacggt gccctcatcg aggtggccct ccgaaacgtt cacatgtaac    600
gtagcacatc cagcctccaa aaccaaggtg gataaacccg tgccgaaaag agagaatggg    660
cgggtgcctc gacccccctga ttgccccaag tgtccggctc cggaaatgct cggtggaccc    720
tcagtgttta tcttccctcc gaagcccaag gacactctgc tgatcgcgcg cactccagaa    780
gtaacatgtg tagtggtgga ccttgatccc gaggaccccg aagtccagat ctcctggttt    840
gtagatggga aacagatgca gaccgcaaaa actcaaccca gagaggagca gttcaacgga    900
acataccgag tggtatccgt ccttccgatt ggccaccagg actggttgaa agggaagcag    960
tttacgtgta aagtcaacaa taaggggttg cctagcccta ttgagcggac gatttcgaaa   1020
gctaggggac aggcccacca gccatcggtc tatgtccttc cgccttcccg cgaggagctc   1080
tcgaagaata cagtgagcct tacatgcctc attaaggatt tcttcccgcc tgatatcgac   1140
gtagagtggc aatcaaacgg tcaacaggag ccggaatcca agtatagaac cactccgccc   1200
cagcttgacg aggacggatc atactttttg tattcaaaac tgtcggtgga taagagccgg   1260
tggcagagag gtgacacctt catctgtgcg gtgatgcacg aagcactcca taatcactac   1320
acccaagaga gcctctcgca ttcccccgga aag                                1353
```

<210> SEQ ID NO 64
<211> LENGTH: 451
<212> TYPE: PRT
<213> ORGANISM: Artificial Sequence
<220> FEATURE:
<223> OTHER INFORMATION: caninized mus musculus

<400> SEQUENCE: 64

```
Glu Ile Gln Leu Val Gln Ser Gly Gly Asp Leu Val Lys Pro Gly Gly
1               5                   10                  15

Ser Leu Arg Leu Ser Cys Lys Ala Ser Gly Tyr Thr Phe Thr Asn Tyr
            20                  25                  30

Gly Met Asn Trp Val Arg Gln Ala Pro Gly Lys Gly Leu Gln Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Phe Ser Leu Asp Asn Ala Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Arg Ser Ile Tyr Tyr Pro Tyr Trp Gly Gln Gly Thr Thr Leu
            100                 105                 110
```

```
Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Asp Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Asn Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450
```

<210> SEQ ID NO 65
<211> LENGTH: 1353
<212> TYPE: DNA
<213> ORGANISM: Artificial Sequence
<220> FEATURE:
<223> OTHER INFORMATION: caninized mus musculus

<400> SEQUENCE: 65

```
gaaattcagc tggtgcagag cggcggcgat ctggtgaaac cgggcggcag cgtgcgcctg     60
agctgcaaag cgagcggcta tacctttacc aactatggca tgaactgggt gaaacaggcg    120
ccgggcaaag gcctgcagtg gatgggctgg attaacacct ataccggcga accgacctat    180
gcggatgatt ttaaaggccg ctttaccttt agcctggata acgcgaaaaa caccgcgtat    240
ctgcagatta acagcctgcg cgcggaagat accgcggtgt atttttgcgc gcgccgcagc    300
atttattatc cgtattgggg ccagggcacc accctgaccg tgagcagcgc ttccacaacc    360
gcgccatcag tctttccgtt ggccccatca tgcgggtcga cgagcggatc gactgtggcc    420
ctggcgtgct tggtgtcggg atactttccc gaacccgtca cggtcagctg gaactccgga    480
tcgcttacga gcggtgtgca tacgttcccc tcggtcttgc aatcatcagg gctctactcg    540
ctgtcgagca tggtaacggt gccctcatcg aggtggccct ccgaaacgtt cacatgtaac    600
gtagcacatc cagcctccaa aaccaaggtg gataaacccg tgccgaaaag agagaatggg    660
cgggtgcctc gacccccctga ttgccccaag tgtccggctc cggaaatgct cggtggaccc    720
tcagtgttta tcttccctcc gaagcccaag gacactctgc tgatcgcgcg cactccagaa    780
gtaacatgtg tagtggtgga ccttgatccc gaggaccccg aagtccagat ctcctggttt    840
gtagatggga aacagatgca gaccgcaaaa actcaaccca gagaggagca gttcaacgga    900
acataccgag tggtatccgt ccttccgatt ggccaccagg actggttgaa agggaagcag    960
tttacgtgta aagtcaacaa taaggggttg cctagcccta ttgagcggac gatttcgaaa   1020
gctaggggac aggcccacca gccatcggtc tatgtccttc cgccttcccg cgaggagctc   1080
tcgaagaata cagtgagcct tacatgcctc attaaggatt tcttcccgcc tgatatcgac   1140
gtagagtggc aatcaaacgg tcaacaggag ccggaatcca agtatagaac cactccgccc   1200
cagcttgacg aggacggatc atactttttg tattcaaaac tgtcggtgga taagagccgg   1260
tggcagagag gtgacacctt catctgtgcg gtgatgcacg aagcactcca taatcactac   1320
acccaagaga gcctctcgca ttcccccgga aag                                 1353
```

<210> SEQ ID NO 66
<211> LENGTH: 451
<212> TYPE: PRT
<213> ORGANISM: Artificial Sequence
<220> FEATURE:
<223> OTHER INFORMATION: caninized mus musculus

<400> SEQUENCE: 66

```
Glu Ile Gln Leu Val Gln Ser Gly Gly Asp Leu Val Lys Pro Gly Gly
1               5                   10                  15

Ser Val Arg Leu Ser Cys Lys Ala Ser Gly Tyr Thr Phe Thr Asn Tyr
            20                  25                  30

Gly Met Asn Trp Val Lys Gln Ala Pro Gly Lys Gly Leu Gln Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Phe Ser Leu Asp Asn Ala Lys Asn Thr Ala Tyr
65                  70                  75                  80

Leu Gln Ile Asn Ser Leu Arg Ala Glu Asp Thr Ala Val Tyr Phe Cys
                85                  90                  95

Ala Arg Arg Ser Ile Tyr Tyr Pro Tyr Trp Gly Gln Gly Thr Thr Leu
            100                 105                 110
```

```
Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Asp Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Asn Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450
```

<210> SEQ ID NO 67
<211> LENGTH: 1365
<212> TYPE: DNA
<213> ORGANISM: Artificial Sequence
<220> FEATURE:
<223> OTHER INFORMATION: caninized mus musculus

<400> SEQUENCE: 67
gaagtgcagc tggtggaaag cggcggcgat ctggtgaaac cgggcggcag cctgcgcctg 60
agctgcgtgg cgagcggctt tacctttagc gattattata tgagctgggt gcgccaggcg 120
ccgggcaaag gcctggaatg ggtggcgttt attcgcaaca aagcgaacgg ctataccacc 180
gaatatagcg cgagcctgaa aggccgcttt accattagcc gcgataacgc gaaaaacatg 240
gcgtatctgc agatgaacag cctgcgcgcg gaagataccg cggtgtatta ttgcgcgagc 300
tttggcctga tgtattattt tgattattgg ggccagggca ccaccctgac cgtgagcagc 360
gcttccacaa ccgcgccatc agtctttccg ttggccccat catgcgggtc gacgagcgga 420
tcgactgtgg ccctggcgtg cttggtgtcg ggatactttc ccgaacccgt cacggtcagc 480
tggaactccg gatcgcttac gagcggtgtg catacgttcc cctcggtctt gcaatcatca 540
gggctctact cgctgtcgag catggtaacg gtgccctcat cgaggtggcc ctccgaaacg 600
ttcacatgta acgtagcaca tccagcctcc aaaaccaagg tggataaacc cgtgccgaaa 660
agagagaatg ggcgggtgcc tcgaccccct gattgcccca agtgtccggc tccggaaatg 720
ctcggtggac cctcagtgtt tatcttccct ccgaagccca aggacactct gctgatcgcg 780
cgcactccag aagtaacatg tgtagtggtg gaccttgatc ccgaggaccc cgaagtccag 840
atctcctggt ttgtagatgg gaaacagatg cagaccgcaa aaactcaacc cagagaggag 900
cagttcaacg gaacataccg agtggtatcc gtccttccga ttggccacca ggactggttg 960
aaagggaagc agtttacgtg taaagtcaac aataaggggt tgcctagccc tattgagcgg 1020
acgatttcga aagctagggg acaggcccac cagccatcgg tctatgtcct tccgccttcc 1080
cgcgaggagc tctcgaagaa tacagtgagc cttacatgcc tcattaagga tttcttcccg 1140
cctgatatcg acgtagagtg gcaatcaaac ggtcaacagg agccggaatc caagtataga 1200
accactccgc cccagcttga cgaggacgga tcatactttt tgtattcaaa actgtcggtg 1260
gataagagcc ggtggcagag aggtgacacc ttcatctgtg cggtgatgca cgaagcactc 1320
cataatcact acacccaaga gagcctctcg cattcccccg gaaag 1365

<210> SEQ ID NO 68
<211> LENGTH: 455
<212> TYPE: PRT
<213> ORGANISM: Artificial Sequence
<220> FEATURE:
<223> OTHER INFORMATION: caninized mus musculus

<400> SEQUENCE: 68

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Phe Ile Arg Asn Lys Ala Asn Gly Tyr Thr Thr Glu Tyr Ser Ala
    50                  55                  60

Ser Leu Lys Gly Arg Phe Thr Ile Ser Arg Asp Asn Ala Lys Asn Met
65                  70                  75                  80

Ala Tyr Leu Gln Met Asn Ser Leu Arg Ala Glu Asp Thr Ala Val Tyr
                85                  90                  95

Tyr Cys Ala Ser Phe Gly Leu Met Tyr Tyr Phe Asp Tyr Trp Gly Gln
            100                 105                 110

```
Gly Thr Thr Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Asn Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455
```

<210> SEQ ID NO 69
<211> LENGTH: 1365
<212> TYPE: DNA
<213> ORGANISM: Artificial Sequence
<220> FEATURE:
<223> OTHER INFORMATION: caninized mus musculus

<400> SEQUENCE: 69

```
gaagtgcagc tggtggaaag cggcggcgat ctggtgaaac cgggcggcag cctgcgcctg     60
agctgcgcga ccagcggctt tacctttagc gattattata tgagctgggt gcgccaggcg    120
ccgggcaaag gcctggaatg gatgggcttt attcgcaaca aagcgaacgg ctataccacc    180
gaatatagcg cgagcctgaa aggccgcttt accattagcc gcgataacgc gaaaaacatg    240
gcgtatctgc agatgaacag cctgcgcgcg gaagataccg cggtgtatta ttgcgtgcgc    300
tttggcctga tgtattattt tgattattgg ggccagggca ccaccctgac cgtgagcagc    360
gcttccacaa ccgcgccatc agtctttccg ttggccccat catgcgggtc gacgagcgga    420
tcgactgtgg ccctggcgtg cttggtgtcg ggatactttc ccgaacccgt cacggtcagc    480
tggaactccg gatcgcttac gagcggtgtg catacgttcc cctcggtctt gcaatcatca    540
gggctctact cgctgtcgag catggtaacg gtgccctcat cgaggtggcc ctccgaaacg    600
ttcacatgta acgtagcaca tccagcctcc aaaaccaagg tggataaacc cgtgccgaaa    660
agagagaatg ggcgggtgcc tcgacccccct gattgcccca agtgtccggc tccggaaatg    720
ctcggtggac cctcagtgtt tatcttccct ccgaagccca aggacactct gctgatcgcg    780
cgcactccag aagtaacatg tgtagtggtg gaccttgatc ccgaggaccc cgaagtccag    840
atctcctggt ttgtagatgg gaaacagatg cagaccgcaa aaactcaacc cagagaggag    900
cagttcaacg gaacataccg agtggtatcc gtccttccga ttggccacca ggactggttg    960
aaagggaagc agtttacgtg taaagtcaac aataaggggt tgcctagccc tattgagcgg   1020
acgatttcga aagctagggg acaggcccac cagccatcgg tctatgtcct tccgccttcc   1080
cgcgaggagc tctcgaagaa tacagtgagc cttacatgcc tcattaagga tttcttcccg   1140
cctgatatcg acgtagagtg gcaatcaaac ggtcaacagg agccggaatc caagtataga   1200
accactccgc cccagcttga cgaggacgga tcatactttt tgtattcaaa actgtcggtg   1260
gataagagcc ggtggcagag aggtgacacc ttcatctgtg cggtgatgca cgaagcactc   1320
cataatcact acacccaaga gagcctctcg cattcccccg gaaag                  1365
```

<210> SEQ ID NO 70
<211> LENGTH: 455
<212> TYPE: PRT
<213> ORGANISM: Artificial Sequence
<220> FEATURE:
<223> OTHER INFORMATION: caninized mus musculus

<400> SEQUENCE: 70

```
Glu Val Gln Leu Val Glu Ser Gly Gly Asp Leu Val Lys Pro Gly Gly
1               5                   10                  15

Ser Leu Arg Leu Ser Cys Ala Thr Ser Gly Phe Thr Phe Ser Asp Tyr
            20                  25                  30

Tyr Met Ser Trp Val Arg Gln Ala Pro Gly Lys Gly Leu Glu Trp Met
        35                  40                  45

Gly Phe Ile Arg Asn Lys Ala Asn Gly Tyr Thr Thr Glu Tyr Ser Ala
    50                  55                  60

Ser Leu Lys Gly Arg Phe Thr Ile Ser Arg Asp Asn Ala Lys Asn Met
65                  70                  75                  80

Ala Tyr Leu Gln Met Asn Ser Leu Arg Ala Glu Asp Thr Ala Val Tyr
                85                  90                  95

Tyr Cys Val Arg Phe Gly Leu Met Tyr Tyr Phe Asp Tyr Trp Gly Gln
            100                 105                 110
```

```
Gly Thr Thr Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Asn Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455
```

<210> SEQ ID NO 71
<211> LENGTH: 1365
<212> TYPE: DNA
<213> ORGANISM: Artificial Sequence
<220> FEATURE:
<223> OTHER INFORMATION: caninized mus musculus

<400> SEQUENCE: 71

```
gaagtgaaac tggtggaaag cggcggcgat ctggtgaaac cgggcggcag cctgcgcctg     60
agctgcgcga ccagcggctt tacctttagc gattattata tgagctgggt gcgccaggcg    120
ccgggcaaag cgctggaatg gatgggcttt attcgcaaca aagcgaacgg ctataccacc    180
gaatatagcg cgagcctgaa aggccgcttt accattagcc gcgataacgc gaaaaacatg    240
ctgtatctgc agatgaacag cctgcgcgcg gaagataccg cggtgtatta ttgcgtgcgc    300
tttggcctga tgtattattt tgattattgg ggccagggca ccaccctgac cgtgagcagc    360
gcttccacaa ccgcgccatc agtctttccg ttggccccat catgcgggtc gacgagcgga    420
tcgactgtgg ccctggcgtg cttggtgtcg ggatactttc ccgaacccgt cacggtcagc    480
tggaactccg gatcgcttac gagcggtgtg catacgttcc cctcggtctt gcaatcatca    540
gggctctact cgctgtcgag catggtaacg gtgccctcat cgaggtggcc ctccgaaacg    600
ttcacatgta acgtagcaca tccagcctcc aaaaccaagg tggataaacc cgtgccgaaa    660
agagagaatg ggcgggtgcc tcgaccccct gattgcccca agtgtccggc tccggaaatg    720
ctcggtggac cctcagtgtt tatcttccct ccgaagccca aggacactct gctgatcgcg    780
cgcactccag aagtaacatg tgtagtggtg gaccttgatc ccgaggaccc cgaagtccag    840
atctcctggt ttgtagatgg gaaacagatg cagaccgcaa aaactcaacc cagagaggag    900
cagttcaacg gaacataccg agtggtatcc gtccttccga ttggccacca ggactggttg    960
aaagggaagc agtttacgtg taaagtcaac aataaggggt tgcctagccc tattgagcgg   1020
acgatttcga aagctagggg acaggcccac cagccatcgg tctatgtcct tccgccttcc   1080
cgcgaggagc tctcgaagaa tacagtgagc cttacatgcc tcattaagga tttcttcccg   1140
cctgatatcg acgtagagtg gcaatcaaac ggtcaacagg agccggaatc caagtataga   1200
accactccgc cccagcttga cgaggacgga tcatactttt tgtattcaaa actgtcggtg   1260
gataagagcc ggtggcagag aggtgacacc ttcatctgtg cggtgatgca cgaagcactc   1320
cataatcact acacccaaga gagcctctcg cattcccccg gaaag                   1365
```

<210> SEQ ID NO 72
<211> LENGTH: 455
<212> TYPE: PRT
<213> ORGANISM: Artificial Sequence
<220> FEATURE:
<223> OTHER INFORMATION: caninized mus musculus

<400> SEQUENCE: 72

```
Glu Val Lys Leu Val Glu Ser Gly Gly Asp Leu Val Lys Pro Gly Gly
1               5                   10                  15

Ser Leu Arg Leu Ser Cys Ala Thr Ser Gly Phe Thr Phe Ser Asp Tyr
            20                  25                  30

Tyr Met Ser Trp Val Arg Gln Ala Pro Gly Lys Ala Leu Glu Trp Met
        35                  40                  45

Gly Phe Ile Arg Asn Lys Ala Asn Gly Tyr Thr Thr Glu Tyr Ser Ala
    50                  55                  60

Ser Leu Lys Gly Arg Phe Thr Ile Ser Arg Asp Asn Ala Lys Asn Met
65                  70                  75                  80

Leu Tyr Leu Gln Met Asn Ser Leu Arg Ala Glu Asp Thr Ala Val Tyr
                85                  90                  95

Tyr Cys Val Arg Phe Gly Leu Met Tyr Tyr Phe Asp Tyr Trp Gly Gln
            100                 105                 110
```

```
Gly Thr Thr Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Asn Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455
```

<210> SEQ ID NO 73
<211> LENGTH: 1353
<212> TYPE: DNA
<213> ORGANISM: Artificial Sequence
<220> FEATURE:
<223> OTHER INFORMATION: caninized mus musculus

<400> SEQUENCE: 73
gaagtgcagc tggtggaaag cggcggcgat ctggtgaaac cgggcggcag cctgcgcctg 60
agctgcgtgg cgagcggcta tacctttacc aactatggca tgaactgggt gcgccaggcg 120
ccgggcaaag gcctgcagtg ggtggcgtgg attaacacct ataccggcga accgacctat 180
gcggatgatt ttaaaggccg ctttaccatt agccgcgata acgcgaaaaa caccctgtat 240
ctgcagatga acagcctgcg cgcggaagat accgcggtgt attattgcgc gcgccgcagc 300
atttattatc cgtattgggg ccagggcacc accctgaccg tgagcagcgc ttccacaacc 360
gcgccatcag tctttccgtt ggccccatca tgcgggtcga cgagcggatc gactgtggcc 420
ctggcgtgct tggtgtcggg atactttccc gaacccgtca cggtcagctg gaactccgga 480
tcgcttacga gcggtgtgca tacgttcccc tcggtcttgc aatcatcagg gctctactcg 540
ctgtcgagca tggtaacggt gccctcatcg aggtggccct ccgaaacgtt cacatgtaac 600
gtagcacatc cagcctccaa aaccaaggtg gataaacccg tgccgaaaag agagaatggg 660
cgggtgcctc gacccccctga ttgccccaag tgtccggctc cggaaatgct cggtggaccc 720
tcagtgttta tcttccctcc gaagcccaag gacactctgc tgatcgcgcg cactccagaa 780
gtaacatgtg tagtggtggc tcttgatccc gaggaccccg aagtccagat ctcctggttt 840
gtagatggga aacagatgca gaccgcaaaa actcaaccca gagaggagca gttcgccgga 900
acataccgag tggtatccgt ccttccgatt ggccaccagg actggttgaa agggaagcag 960
tttacgtgta aagtcaacaa taaggggttg cctagcccta ttgagcggac gatttcgaaa 1020
gctaggggac aggcccacca gccatcggtc tatgtccttc cgccttcccg cgaggagctc 1080
tcgaagaata cagtgagcct tacatgcctc attaaggatt tcttcccgcc tgatatcgac 1140
gtagagtggc aatcaaacgg tcaacaggag ccggaatcca agtatagaac cactccgccc 1200
cagcttgacg aggacggatc atactttttg tattcaaaac tgtcggtgga taagagccgg 1260
tggcagagag gtgacacctt catctgtgcg gtgatgcacg aagcactcca taatcactac 1320
acccaagaga gcctctcgca ttcccccgga aag 1353

<210> SEQ ID NO 74
<211> LENGTH: 451
<212> TYPE: PRT
<213> ORGANISM: Artificial Sequence
<220> FEATURE:
<223> OTHER INFORMATION: caninized mus musculus

<400> SEQUENCE: 74

Glu Val Gln Leu Val Glu Ser Gly Gly Asp Leu Val Lys Pro Gly Gly
1               5                   10                  15

Ser Leu Arg Leu Ser Cys Val Ala Ser Gly Tyr Thr Phe Thr Asn Tyr
            20                  25                  30

Gly Met Asn Trp Val Arg Gln Ala Pro Gly Lys Gly Leu Gln Trp Val
        35                  40                  45

Ala Trp Ile Asn Thr Tyr Thr Gly Glu Pro Thr Tyr Ala Asp Asp Phe
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Ile Tyr Tyr Pro Tyr Trp Gly Gln Gly Thr Thr Leu
            100                 105                 110

```
Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Ala Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Ala Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450


<210> SEQ ID NO 75
<211> LENGTH: 1353
<212> TYPE: DNA
<213> ORGANISM: Artificial Sequence
<220> FEATURE:
<223> OTHER INFORMATION: caninized mus musculus
```

<400> SEQUENCE: 75

```
gaaattcagc tggtgcagag cggcggcgat ctggtgaaac cgggcggcag cctgcgcctg     60
agctgcaaag cgagcggcta tacctttacc aactatggca tgaactgggt gcgccaggcg    120
ccgggcaaag gcctgcagtg gatgggctgg attaacacct ataccggcga accgacctat    180
gcggatgatt ttaaaggccg ctttaccttt agcctggata acgcgaaaaa caccctgtat    240
ctgcagatga acagcctgcg cgcggaagat accgcggtgt atttttgcgc gcgccgcagc    300
atttattatc cgtattgggg ccagggcacc accctgaccg tgagcagcgc ttccacaacc    360
gcgccatcag tctttccgtt ggccccatca tgcgggtcga cgagcggatc gactgtggcc    420
ctggcgtgct tggtgtcggg atactttccc gaacccgtca cggtcagctg gaactccgga    480
tcgcttacga gcggtgtgca tacgttcccc tcggtcttgc aatcatcagg gctctactcg    540
ctgtcgagca tggtaacggt gccctcatcg aggtggccct ccgaaacgtt cacatgtaac    600
gtagcacatc cagcctccaa aaccaaggtg gataaacccg tgccgaaaag agagaatggg    660
cgggtgcctc gacccccctga ttgccccaag tgtccggctc cggaaatgct cggtggaccc    720
tcagtgttta tcttccctcc gaagcccaag gacactctgc tgatcgcgcg cactccagaa    780
gtaacatgtg tagtggtggc tcttgatccc gaggaccccg aagtccagat ctcctggttt    840
gtagatggga aacagatgca gaccgcaaaa actcaaccca gagaggagca gttcgccgga    900
acataccgag tggtatccgt ccttccgatt ggccaccagg actggttgaa agggaagcag    960
tttacgtgta aagtcaacaa taaggggttg cctagcccta ttgagcggac gatttcgaaa   1020
gctaggggac aggcccacca gccatcggtc tatgtccttc cgccttcccg cgaggagctc   1080
tcgaagaata cagtgagcct tacatgcctc attaaggatt tcttcccgcc tgatatcgac   1140
gtagagtggc aatcaaacgg tcaacaggag ccggaatcca agtatagaac cactccgccc   1200
cagcttgacg aggacggatc atactttttg tattcaaaac tgtcggtgga taagagccgg   1260
tggcagagag gtgacacctt catctgtgcg gtgatgcacg aagcactcca taatcactac   1320
acccaagaga gcctctcgca ttcccccgga aag                                1353
```

<210> SEQ ID NO 76
<211> LENGTH: 451
<212> TYPE: PRT
<213> ORGANISM: Artificial Sequence
<220> FEATURE:
<223> OTHER INFORMATION: caninized mus musculus

<400> SEQUENCE: 76

```
Glu Ile Gln Leu Val Gln Ser Gly Gly Asp Leu Val Lys Pro Gly Gly
1               5                   10                  15

Ser Leu Arg Leu Ser Cys Lys Ala Ser Gly Tyr Thr Phe Thr Asn Tyr
            20                  25                  30

Gly Met Asn Trp Val Arg Gln Ala Pro Gly Lys Gly Leu Gln Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Phe Ser Leu Asp Asn Ala Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Arg Ser Ile Tyr Tyr Pro Tyr Trp Gly Gln Gly Thr Thr Leu
            100                 105                 110
```

```
Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Ala Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Ala Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450
```

<210> SEQ ID NO 77
<211> LENGTH: 1353
<212> TYPE: DNA
<213> ORGANISM: Artificial Sequence
<220> FEATURE:
<223> OTHER INFORMATION: caninized mus musculus

<400> SEQUENCE: 77
gaaattcagc tggtgcagag cggcggcgat ctggtgaaac cgggcggcag cgtgcgcctg 60
agctgcaaag cgagcggcta tacctttacc aactatggca tgaactgggt gaaacaggcg 120
ccgggcaaag gcctgcagtg gatgggctgg attaacacct ataccggcga accgacctat 180
gcggatgatt ttaaaggccg ctttaccttt agcctggata acgcgaaaaa caccgcgtat 240
ctgcagatta acagcctgcg cgcggaagat accgcggtgt atttttgcgc gcgccgcagc 300
atttattatc cgtattgggg ccagggcacc accctgaccg tgagcagcgc ttccacaacc 360
gcgccatcag tctttccgtt ggccccatca tgcgggtcga cgagcggatc gactgtggcc 420
ctggcgtgct tggtgtcggg atactttccc gaacccgtca cggtcagctg gaactccgga 480
tcgcttacga gcggtgtgca tacgttcccc tcggtcttgc aatcatcagg gctctactcg 540
ctgtcgagca tggtaacggt gccctcatcg aggtggccct ccgaaacgtt cacatgtaac 600
gtagcacatc cagcctccaa aaccaaggtg gataaacccg tgccgaaaag agagaatggg 660
cgggtgcctc gacccccctga ttgccccaag tgtccggctc cggaaatgct cggtggaccc 720
tcagtgttta tcttccctcc gaagcccaag gacactctgc tgatcgcgcg cactccagaa 780
gtaacatgtg tagtggtggc tcttgatccc gaggaccccg aagtccagat ctcctggttt 840
gtagatggga aacagatgca gaccgcaaaa actcaaccca gagaggagca gttcgccgga 900
acataccgag tggtatccgt ccttccgatt ggccaccagg actggttgaa agggaagcag 960
tttacgtgta aagtcaacaa taaggggttg cctagcccta ttgagcggac gatttcgaaa 1020
gctaggggac aggcccacca gccatcggtc tatgtccttc cgccttcccg cgaggagctc 1080
tcgaagaata cagtgagcct tacatgcctc attaaggatt tcttcccgcc tgatatcgac 1140
gtagagtggc aatcaaacgg tcaacaggag ccggaatcca agtatagaac cactccgccc 1200
cagcttgacg aggacggatc atactttttg tattcaaaac tgtcggtgga taagagccgg 1260
tggcagagag gtgacacctt catctgtgcg gtgatgcacg aagcactcca taatcactac 1320
acccaagaga gcctctcgca ttcccccgga aag 1353

<210> SEQ ID NO 78
<211> LENGTH: 451
<212> TYPE: PRT
<213> ORGANISM: Artificial Sequence
<220> FEATURE:
<223> OTHER INFORMATION: caninized mus musculus

<400> SEQUENCE: 78

Glu Ile Gln Leu Val Gln Ser Gly Gly Asp Leu Val Lys Pro Gly Gly
1 5 10 15

Ser Val Arg Leu Ser Cys Lys Ala Ser Gly Tyr Thr Phe Thr Asn Tyr
20 25 30

Gly Met Asn Trp Val Lys Gln Ala Pro Gly Lys Gly Leu Gln Trp Met
35 40 45

Gly Trp Ile Asn Thr Tyr Thr Gly Glu Pro Thr Tyr Ala Asp Asp Phe
50 55 60

Lys Gly Arg Phe Thr Phe Ser Leu Asp Asn Ala Lys Asn Thr Ala Tyr
65 70 75 80

Leu Gln Ile Asn Ser Leu Arg Ala Glu Asp Thr Ala Val Tyr Phe Cys
85 90 95

Ala Arg Arg Ser Ile Tyr Tyr Pro Tyr Trp Gly Gln Gly Thr Thr Leu
100 105 110

```
Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
                165                 170                 175

Gly Leu Tyr Ser Leu Ser Ser Met Val Thr Val Pro Ser Ser Arg Trp
            180                 185                 190

Pro Ser Glu Thr Phe Thr Cys Asn Val Ala His Pro Ala Ser Lys Thr
        195                 200                 205

Lys Val Asp Lys Pro Val Pro Lys Arg Glu Asn Gly Arg Val Pro Arg
    210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Ala Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Ala Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450


<210> SEQ ID NO 79
<211> LENGTH: 1365
<212> TYPE: DNA
<213> ORGANISM: Artificial Sequence
<220> FEATURE:
<223> OTHER INFORMATION: caninized mus musculus
```

<400> SEQUENCE: 79

```
gaagtgcagc tggtggaaag cggcggcgat ctggtgaaac cgggcggcag cctgcgcctg     60
agctgcgtgg cgagcggctt tacctttagc gattattata tgagctgggt gcgccaggcg    120
ccgggcaaag gcctggaatg ggtggcgttt attcgcaaca aagcgaacgg ctataccacc    180
gaatatagcg cgagcctgaa aggccgcttt accattagcc gcgataacgc gaaaaacatg    240
gcgtatctgc agatgaacag cctgcgcgcg gaagataccg cggtgtatta ttgcgcgagc    300
tttggcctga tgtattattt tgattattgg ggccagggca ccaccctgac cgtgagcagc    360
gcttccacaa ccgcgccatc agtctttccg ttggccccat catgcgggtc gacgagcgga    420
tcgactgtgg ccctggcgtg cttggtgtcg ggatactttc ccgaacccgt cacggtcagc    480
tggaactccg gatcgcttac gagcggtgtg catacgttcc cctcggtctt gcaatcatca    540
gggctctact cgctgtcgag catggtaacg gtgccctcat cgaggtggcc ctccgaaacg    600
ttcacatgta acgtagcaca tccagcctcc aaaaccaagg tggataaacc cgtgccgaaa    660
agagagaatg ggcgggtgcc tcgacccccct gattgcccca agtgtccggc tccggaaatg    720
ctcggtggac cctcagtgtt tatcttccct ccgaagccca aggacactct gctgatcgcg    780
cgcactccag aagtaacatg tgtagtggtg gctcttgatc ccgaggaccc cgaagtccag    840
atctcctggt ttgtagatgg gaaacagatg cagaccgcaa aaactcaacc cagagaggag    900
cagttcgccg gaacataccg agtggtatcc gtccttccga ttggccacca ggactggttg    960
aaagggaagc agtttacgtg taaagtcaac aataaggggt tgcctagccc tattgagcgg   1020
acgatttcga aagctagggg acaggcccac cagccatcgg tctatgtcct tccgccttcc   1080
cgcgaggagc tctcgaagaa tacagtgagc cttacatgcc tcattaagga tttcttcccg   1140
cctgatatcg acgtagagtg gcaatcaaac ggtcaacagg agccggaatc caagtataga   1200
accactccgc cccagcttga cgaggacgga tcatactttt tgtattcaaa actgtcggtg   1260
gataagagcc ggtggcagag aggtgacacc ttcatctgtg cggtgatgca cgaagcactc   1320
cataatcact acacccaaga gagcctctcg cattcccccg gaaag                   1365
```

<210> SEQ ID NO 80
<211> LENGTH: 455
<212> TYPE: PRT
<213> ORGANISM: Artificial Sequence
<220> FEATURE:
<223> OTHER INFORMATION: caninized mus musculus

<400> SEQUENCE: 80

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Phe Ile Arg Asn Lys Ala Asn Gly Tyr Thr Thr Glu Tyr Ser Ala
    50                  55                  60

Ser Leu Lys Gly Arg Phe Thr Ile Ser Arg Asp Asn Ala Lys Asn Met
65                  70                  75                  80

Ala Tyr Leu Gln Met Asn Ser Leu Arg Ala Glu Asp Thr Ala Val Tyr
                85                  90                  95

Tyr Cys Ala Ser Phe Gly Leu Met Tyr Tyr Phe Asp Tyr Trp Gly Gln
            100                 105                 110
```

```
Gly Thr Thr Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Ala Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Ala Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455
```

```
<210> SEQ ID NO 81
<211> LENGTH: 1365
<212> TYPE: DNA
<213> ORGANISM: Artificial Sequence
<220> FEATURE:
<223> OTHER INFORMATION: caninized mus musculus
```

<400> SEQUENCE: 81
gaagtgcagc tggtggaaag cggcggcgat ctggtgaaac cgggcggcag cctgcgcctg 60
agctgcgcga ccagcggctt tacctttagc gattattata tgagctgggt gcgccaggcg 120
ccgggcaaag gcctggaatg gatgggcttt attcgcaaca aagcgaacgg ctataccacc 180
gaatatagcg cgagcctgaa aggccgcttt accattagcc gcgataacgc gaaaaacatg 240
gcgtatctgc agatgaacag cctgcgcgcg gaagataccg cggtgtatta ttgcgtgcgc 300
tttggcctga tgtattattt tgattattgg ggccagggca ccaccctgac cgtgagcagc 360
gcttccacaa ccgcgccatc agtctttccg ttggccccat catgcgggtc gacgagcgga 420
tcgactgtgg ccctggcgtg cttggtgtcg ggatactttc ccgaacccgt cacggtcagc 480
tggaactccg gatcgcttac gagcggtgtg catacgttcc cctcggtctt gcaatcatca 540
gggctctact cgctgtcgag catggtaacg gtgccctcat cgaggtggcc ctccgaaacg 600
ttcacatgta acgtagcaca tccagcctcc aaaaccaagg tggataaacc cgtgccgaaa 660
agagagaatg ggcgggtgcc tcgacccccct gattgcccca agtgtccggc tccggaaatg 720
ctcggtggac cctcagtgtt tatcttccct ccgaagccca aggacactct gctgatcgcg 780
cgcactccag aagtaacatg tgtagtggtg gctcttgatc ccgaggaccc cgaagtccag 840
atctcctggt ttgtagatgg gaaacagatg cagaccgcaa aaactcaacc cagagaggag 900
cagttcgccg gaacataccg agtggtatcc gtccttccga ttggccacca ggactggttg 960
aaagggaagc agtttacgtg taaagtcaac aataaggggt tgcctagccc tattgagcgg 1020
acgatttcga aagctagggg acaggcccac cagccatcgg tctatgtcct tccgccttcc 1080
cgcgaggagc tctcgaagaa tacagtgagc cttacatgcc tcattaagga tttcttcccg 1140
cctgatatcg acgtagagtg gcaatcaaac ggtcaacagg agccggaatc caagtataga 1200
accactccgc cccagcttga cgaggacgga tcatactttt tgtattcaaa actgtcggtg 1260
gataagagcc ggtggcagag aggtgacacc ttcatctgtg cggtgatgca cgaagcactc 1320
cataatcact acacccaaga gagcctctcg cattcccccg gaaag 1365

<210> SEQ ID NO 82
<211> LENGTH: 455
<212> TYPE: PRT
<213> ORGANISM: Artificial Sequence
<220> FEATURE:
<223> OTHER INFORMATION: caninized mus musculus

<400> SEQUENCE: 82

Glu Val Gln Leu Val Glu Ser Gly Gly Asp Leu Val Lys Pro Gly Gly
1 5 10 15

Ser Leu Arg Leu Ser Cys Ala Thr Ser Gly Phe Thr Phe Ser Asp Tyr
20 25 30

Tyr Met Ser Trp Val Arg Gln Ala Pro Gly Lys Gly Leu Glu Trp Met
35 40 45

Gly Phe Ile Arg Asn Lys Ala Asn Gly Tyr Thr Thr Glu Tyr Ser Ala
50 55 60

Ser Leu Lys Gly Arg Phe Thr Ile Ser Arg Asp Asn Ala Lys Asn Met
65 70 75 80

Ala Tyr Leu Gln Met Asn Ser Leu Arg Ala Glu Asp Thr Ala Val Tyr
85 90 95

Tyr Cys Val Arg Phe Gly Leu Met Tyr Tyr Phe Asp Tyr Trp Gly Gln
100 105 110

```
Gly Thr Thr Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Ala Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Ala Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455
```

<210> SEQ ID NO 83
<211> LENGTH: 1365
<212> TYPE: DNA
<213> ORGANISM: Artificial Sequence
<220> FEATURE:
<223> OTHER INFORMATION: caninized mus musculus

<400> SEQUENCE: 83
gaagtgaaac tggtggaaag cggcggcgat ctggtgaaac cgggcggcag cctgcgcctg 60
agctgcgcga ccagcggctt tacctttagc gattattata tgagctgggt gcgccaggcg 120
ccgggcaaag cgctggaatg gatgggcttt attcgcaaca aagcgaacgg ctataccacc 180
gaatatagcg cgagcctgaa aggccgcttt accattagcc gcgataacgc gaaaaacatg 240
ctgtatctgc agatgaacag cctgcgcgcg gaagataccg cggtgtatta ttgcgtgcgc 300
tttggcctga tgtattattt tgattattgg ggccagggca ccaccctgac cgtgagcagc 360
gcttccacaa ccgcgccatc agtctttccg ttggccccat catgcgggtc gacgagcgga 420
tcgactgtgg ccctggcgtg cttggtgtcg ggatactttc ccgaacccgt cacggtcagc 480
tggaactccg gatcgcttac gagcggtgtg catacgttcc cctcggtctt gcaatcatca 540
gggctctact cgctgtcgag catggtaacg gtgccctcat cgaggtggcc ctccgaaacg 600
ttcacatgta acgtagcaca tccagcctcc aaaaccaagg tggataaacc cgtgccgaaa 660
agagagaatg ggcgggtgcc tcgaccccct gattgcccca agtgtccggc tccggaaatg 720
ctcggtggac cctcagtgtt tatcttccct ccgaagccca aggacactct gctgatcgcg 780
cgcactccag aagtaacatg tgtagtggtg gctcttgatc ccgaggaccc cgaagtccag 840
atctcctggt ttgtagatgg gaaacagatg cagaccgcaa aaactcaacc cagagaggag 900
cagttcgccg gaacataccg agtggtatcc gtccttccga ttggccacca ggactggttg 960
aaagggaagc agtttacgtg taaagtcaac aataaggggt tgcctagccc tattgagcgg 1020
acgatttcga aagctagggg acaggcccac cagccatcgg tctatgtcct tccgccttcc 1080
cgcgaggagc tctcgaagaa tacagtgagc cttacatgcc tcattaagga tttcttcccg 1140
cctgatatcg acgtagagtg gcaatcaaac ggtcaacagg agccggaatc caagtataga 1200
accactccgc cccagcttga cgaggacgga tcatactttt tgtattcaaa actgtcggtg 1260
gataagagcc ggtggcagag aggtgacacc ttcatctgtg cggtgatgca cgaagcactc 1320
cataatcact acacccaaga gagcctctcg cattcccccg gaaag 1365

<210> SEQ ID NO 84
<211> LENGTH: 455
<212> TYPE: PRT
<213> ORGANISM: Artificial Sequence
<220> FEATURE:
<223> OTHER INFORMATION: caninized mus musculus

<400> SEQUENCE: 84

Glu Val Lys Leu Val Glu Ser Gly Gly Asp Leu Val Lys Pro Gly Gly
1 5 10 15

Ser Leu Arg Leu Ser Cys Ala Thr Ser Gly Phe Thr Phe Ser Asp Tyr
20 25 30

Tyr Met Ser Trp Val Arg Gln Ala Pro Gly Lys Ala Leu Glu Trp Met
35 40 45

Gly Phe Ile Arg Asn Lys Ala Asn Gly Tyr Thr Thr Glu Tyr Ser Ala
50 55 60

Ser Leu Lys Gly Arg Phe Thr Ile Ser Arg Asp Asn Ala Lys Asn Met
65 70 75 80

Leu Tyr Leu Gln Met Asn Ser Leu Arg Ala Glu Asp Thr Ala Val Tyr
85 90 95

Tyr Cys Val Arg Phe Gly Leu Met Tyr Tyr Phe Asp Tyr Trp Gly Gln
100 105 110

```
Gly Thr Thr Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Ala Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Ala Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455
```

<210> SEQ ID NO 85
<211> LENGTH: 15
<212> TYPE: DNA
<213> ORGANISM: Mus musculus

<400> SEQUENCE: 85
aactatggaa tgaac 15

<210> SEQ ID NO 86

<211> LENGTH: 5
<212> TYPE: PRT
<213> ORGANISM: Mus musculus

<400> SEQUENCE: 86

Asn Tyr Gly Met Asn
1 5

<210> SEQ ID NO 87
<211> LENGTH: 51
<212> TYPE: DNA
<213> ORGANISM: Mus musculus

<400> SEQUENCE: 87
tggataaaca cctacactgg agagccaaca tatgctgatg acttcaaggg a 51

<210> SEQ ID NO 88
<211> LENGTH: 17
<212> TYPE: PRT
<213> ORGANISM: Mus musculus

<400> SEQUENCE: 88

Trp Ile Asn Thr Tyr Thr Gly Glu Pro Thr Tyr Ala Asp Asp Phe Lys
1 5 10 15

Gly

<210> SEQ ID NO 89
<211> LENGTH: 21
<212> TYPE: DNA
<213> ORGANISM: Mus musculus

<400> SEQUENCE: 89
cggtcaattt attacccgta c 21

<210> SEQ ID NO 90
<211> LENGTH: 7
<212> TYPE: PRT
<213> ORGANISM: Mus musculus

<400> SEQUENCE: 90

Arg Ser Ile Tyr Tyr Pro Tyr
1 5

<210> SEQ ID NO 91
<211> LENGTH: 48
<212> TYPE: DNA
<213> ORGANISM: Mus musculus

<400> SEQUENCE: 91
agatctagtc agagcattgt atatagtaat ggaaacacct atttagaa 48

<210> SEQ ID NO 92
<211> LENGTH: 16
<212> TYPE: PRT
<213> ORGANISM: Mus musculus

<400> SEQUENCE: 92

Arg Ser Ser Gln Ser Ile Val Tyr Ser Asn Gly Asn Thr Tyr Leu Glu
1 5 10 15

<210> SEQ ID NO 93
<211> LENGTH: 21
<212> TYPE: DNA
<213> ORGANISM: Mus musculus

<400> SEQUENCE: 93
aaagtttcca accgattttc t 21

<210> SEQ ID NO 94
<211> LENGTH: 7
<212> TYPE: PRT
<213> ORGANISM: Mus musculus

<400> SEQUENCE: 94

Lys Val Ser Asn Arg Phe Ser
1 5

<210> SEQ ID NO 95
<211> LENGTH: 27
<212> TYPE: DNA
<213> ORGANISM: Mus musculus

<400> SEQUENCE: 95
tttcaaggtt cacatgttcc gtggacg 27

<210> SEQ ID NO 96
<211> LENGTH: 9
<212> TYPE: PRT
<213> ORGANISM: Mus musculus

<400> SEQUENCE: 96

Phe Gln Gly Ser His Val Pro Trp Thr
1 5

<210> SEQ ID NO 97
<211> LENGTH: 15
<212> TYPE: DNA
<213> ORGANISM: Mus musculus

<400> SEQUENCE: 97
gattactaca tgagc 15

<210> SEQ ID NO 98
<211> LENGTH: 5
<212> TYPE: PRT
<213> ORGANISM: Mus musculus

<400> SEQUENCE: 98

Asp Tyr Tyr Met Ser
1 5

<210> SEQ ID NO 99
<211> LENGTH: 57
<212> TYPE: DNA
<213> ORGANISM: Mus musculus

<400> SEQUENCE: 99
tttattagaa acaaagctaa tggttacaca acagagtaca gcgcatctct gaagggt 57

<210> SEQ ID NO 100
<211> LENGTH: 19
<212> TYPE: PRT
<213> ORGANISM: Mus musculus

<400> SEQUENCE: 100

Phe Ile Arg Asn Lys Ala Asn Gly Tyr Thr Thr Glu Tyr Ser Ala Ser
1 5 10 15

Leu Lys Gly

<210> SEQ ID NO 101
<211> LENGTH: 27
<212> TYPE: DNA
<213> ORGANISM: Mus musculus

<400> SEQUENCE: 101
tttgggttaa tgtactactt tgactac 27

<210> SEQ ID NO 102
<211> LENGTH: 9
<212> TYPE: PRT
<213> ORGANISM: Mus musculus

<400> SEQUENCE: 102

Phe Gly Leu Met Tyr Tyr Phe Asp Tyr
1 5

<210> SEQ ID NO 103
<211> LENGTH: 36
<212> TYPE: DNA
<213> ORGANISM: Mus musculus

<400> SEQUENCE: 103
agggccagct caagtgtaag ttccagttac ttgcac 36

<210> SEQ ID NO 104
<211> LENGTH: 12
<212> TYPE: PRT
<213> ORGANISM: Mus musculus

<400> SEQUENCE: 104

Arg Ala Ser Ser Ser Val Ser Ser Ser Tyr Leu His
1 5 10

<210> SEQ ID NO 105
<211> LENGTH: 21
<212> TYPE: DNA
<213> ORGANISM: Mus musculus

<400> SEQUENCE: 105
agcacatcca acttggcttc t 21

<210> SEQ ID NO 106
<211> LENGTH: 7
<212> TYPE: PRT
<213> ORGANISM: Mus musculus

<400> SEQUENCE: 106

Ser Thr Ser Asn Leu Ala Ser
1 5

<210> SEQ ID NO 107
<211> LENGTH: 27
<212> TYPE: DNA
<213> ORGANISM: Mus musculus

<400> SEQUENCE: 107
cagcagtaca gtggtctccc actcacg 27

<210> SEQ ID NO 108
<211> LENGTH: 9
<212> TYPE: PRT
<213> ORGANISM: Mus musculus

<400> SEQUENCE: 108

Gln Gln Tyr Ser Gly Leu Pro Leu Thr
1 5

<210> SEQ ID NO 109
<211> LENGTH: 5
<212> TYPE: PRT
<213> ORGANISM: Mus musculus

<400> SEQUENCE: 109

Thr Tyr Gly Val Ser
1 5

<210> SEQ ID NO 110
<211> LENGTH: 5
<212> TYPE: PRT
<213> ORGANISM: Mus musculus

<400> SEQUENCE: 110

Ser Tyr Trp Met His
1 5

<210> SEQ ID NO 111
<211> LENGTH: 17
<212> TYPE: PRT
<213> ORGANISM: Mus musculus

<400> SEQUENCE: 111

Trp Ile Asn Thr Tyr Ser Gly Met Pro Thr Tyr Val Asp Asp Phe Lys
1 5 10 15

Gly

<210> SEQ ID NO 112
<211> LENGTH: 17
<212> TYPE: PRT
<213> ORGANISM: Mus musculus

<400> SEQUENCE: 112

Asn Ile Asn Pro Ser Asn Gly Gly Thr Arg Phe Asn Glu Lys Phe Lys
1 5 10 15

Asn

<210> SEQ ID NO 113
<211> LENGTH: 7
<212> TYPE: PRT
<213> ORGANISM: Mus musculus

<400> SEQUENCE: 113

Arg Gly Thr Tyr Tyr Arg Pro
1 5

<210> SEQ ID NO 114
<211> LENGTH: 7
<212> TYPE: PRT

<213> ORGANISM: Mus musculus

<400> SEQUENCE: 114

Arg Gly Ile Ser Phe Asp Tyr
1 5

<210> SEQ ID NO 115
<211> LENGTH: 7
<212> TYPE: PRT
<213> ORGANISM: Mus musculus

<400> SEQUENCE: 115

Arg Gly Val Arg Leu Asp Tyr
1 5

<210> SEQ ID NO 116
<211> LENGTH: 12
<212> TYPE: PRT
<213> ORGANISM: Mus musculus

<400> SEQUENCE: 116

Ser Asn Tyr Gly Ser Gly Trp Ala Trp Phe Ala Tyr
1 5 10

<210> SEQ ID NO 117
<211> LENGTH: 16
<212> TYPE: PRT
<213> ORGANISM: Mus musculus

<400> SEQUENCE: 117

Arg Ser Ser Gln Ser Ile Val Tyr Ser His Gly Asn Thr Tyr Leu Glu
1 5 10 15

<210> SEQ ID NO 118
<211> LENGTH: 16
<212> TYPE: PRT
<213> ORGANISM: Mus musculus

<400> SEQUENCE: 118

Lys Ser Ser Gln Ser Ile Val Tyr Ile Asn Gly Asn Thr Tyr Leu Glu
1 5 10 15

<210> SEQ ID NO 119
<211> LENGTH: 16
<212> TYPE: PRT
<213> ORGANISM: Mus musculus

<400> SEQUENCE: 119

Arg Ser Ser Gln Ser Ile Val Tyr Ile Ser Gly Ser Thr Tyr Leu Glu
1 5 10 15

<210> SEQ ID NO 120
<211> LENGTH: 11
<212> TYPE: PRT
<213> ORGANISM: Mus musculus

<400> SEQUENCE: 120

His Ala Ser Gln Asn Ile Asn Val Trp Leu Ser
1 5 10

<210> SEQ ID NO 121
<211> LENGTH: 7
<212> TYPE: PRT
<213> ORGANISM: Mus musculus

<400> SEQUENCE: 121

Lys Val Ser Lys Arg Phe Ser
1 5

<210> SEQ ID NO 122
<211> LENGTH: 7
<212> TYPE: PRT
<213> ORGANISM: Mus musculus

<400> SEQUENCE: 122

Lys Val Ser Ser Arg Phe Ser
1 5

<210> SEQ ID NO 123
<211> LENGTH: 7
<212> TYPE: PRT
<213> ORGANISM: Mus musculus

<400> SEQUENCE: 123

Lys Ser Ser Asn Leu His Thr
1 5

<210> SEQ ID NO 124
<211> LENGTH: 9
<212> TYPE: PRT
<213> ORGANISM: Mus musculus

<400> SEQUENCE: 124

Gln Gln Gly Gln Ser Tyr Pro Trp Thr
1 5

<210> SEQ ID NO 125
<211> LENGTH: 669
<212> TYPE: DNA
<213> ORGANISM: Canis familiaris

<400> SEQUENCE: 125
atggcgggct ttggctttcg ccgccatggc gcgcagccgg atctggcgag ccgcacctgg 60
ccgtgcaccg cgctgtttag cctgctgttt attccggtgt ttagcaaagg catgcatgtg 120
gcgcagccgg cggtggtgct ggcgagcagc cgcggcgtgg cgagctttgt gtgcgaatat 180
ggcagcagcg gcaacgcggc ggaagtgcgc gtgaccgtgc tgcgccaggc gggcagccag 240
atgaccgaag tgtgcgcggc gacctatacc gtggaagatg aactggcgtt tctggatgat 300
agcacctgca ccggcaccag cagcggcaac aaagtgaacc tgaccattca gggcctgcgc 360
gcgatggata ccggcctgta tatttgcaaa gtggaactga tgtatccgcc gccgtattat 420
gtgggcatgg gcaacggcac ccagatttat gtgattgatc cggaaccgtg cccggatagc 480
gattttctgc tgtggattct ggcggcggtg agcagcggcc tgttttttta tagctttctg 540
attaccgcgg tgagcctgag caaaatgctg aaaaaacgca gcccgctgac caccggcgtg 600
tatgtgaaaa tgccgccgac cgaaccggaa tgcgaaaaac agtttcagcc gtattttatt 660
ccgattaac 669

<210> SEQ ID NO 126
<211> LENGTH: 223
<212> TYPE: PRT
<213> ORGANISM: Canis familiaris

<400> SEQUENCE: 126

Met Ala Gly Phe Gly Phe Arg Arg His Gly Ala Gln Pro Asp Leu Ala
1 5 10 15

Ser Arg Thr Trp Pro Cys Thr Ala Leu Phe Ser Leu Leu Phe Ile Pro
20 25 30

Val Phe Ser Lys Gly Met His Val Ala Gln Pro Ala Val Val Leu Ala
35 40 45

Ser Ser Arg Gly Val Ala Ser Phe Val Cys Glu Tyr Gly Ser Ser Gly
50 55 60

Asn Ala Ala Glu Val Arg Val Thr Val Leu Arg Gln Ala Gly Ser Gln
65 70 75 80

Met Thr Glu Val Cys Ala Ala Thr Tyr Thr Val Glu Asp Glu Leu Ala
85 90 95

Phe Leu Asp Asp Ser Thr Cys Thr Gly Thr Ser Ser Gly Asn Lys Val
100 105 110

Asn Leu Thr Ile Gln Gly Leu Arg Ala Met Asp Thr Gly Leu Tyr Ile
115 120 125

Cys Lys Val Glu Leu Met Tyr Pro Pro Pro Tyr Tyr Val Gly Met Gly
130 135 140

Asn Gly Thr Gln Ile Tyr Val Ile Asp Pro Glu Pro Cys Pro Asp Ser
145 150 155 160

Asp Phe Leu Leu Trp Ile Leu Ala Ala Val Ser Ser Gly Leu Phe Phe
165 170 175

Tyr Ser Phe Leu Ile Thr Ala Val Ser Leu Ser Lys Met Leu Lys Lys
180 185 190

Arg Ser Pro Leu Thr Thr Gly Val Tyr Val Lys Met Pro Pro Thr Glu
195 200 205

Pro Glu Cys Glu Lys Gln Phe Gln Pro Tyr Phe Ile Pro Ile Asn
210 215 220

<210> SEQ ID NO 127
<211> LENGTH: 215
<212> TYPE: PRT
<213> ORGANISM: Artificial Sequence
<220> FEATURE:
<223> OTHER INFORMATION: genetically modified canis familiaris

<400> SEQUENCE: 127

Leu Gly Gly Pro Ser Val Phe Ile Phe Pro Pro Lys Pro Lys Asp Thr
1 5 10 15

Leu Leu Ile Ala Arg Thr Pro Glu Val Thr Cys Val Val Val Ala Leu
20 25 30

Asp Pro Glu Asp Pro Glu Val Gln Ile Ser Trp Phe Val Asp Gly Lys
35 40 45

Gln Met Gln Thr Ala Lys Thr Gln Pro Arg Glu Glu Gln Phe Ala Gly
50 55 60

Thr Tyr Arg Val Val Ser Val Leu Pro Ile Gly His Gln Asp Trp Leu
65 70 75 80

Lys Gly Lys Gln Phe Thr Cys Lys Val Asn Asn Lys Ala Leu Pro Ser
85 90 95

Pro Ile Glu Arg Thr Ile Ser Lys Ala Arg Gly Gln Ala His Gln Pro
100 105 110

Ser Val Tyr Val Leu Pro Pro Ser Arg Glu Glu Leu Ser Lys Asn Thr
115 120 125

```
Val Ser Leu Thr Cys Leu Ile Lys Asp Phe Phe Pro Pro Asp Ile Asp
    130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Glu Ser
        195                 200                 205

Leu Ser His Ser Pro Gly Lys
    210                 215


<210> SEQ ID NO 128
<211> LENGTH: 17
<212> TYPE: PRT
<213> ORGANISM: Canis familiaris

<400> SEQUENCE: 128

Phe Asn Glu Cys Arg Cys Thr Asp Thr Pro Pro Cys Pro Val Pro Glu
1               5                   10                  15

Pro


<210> SEQ ID NO 129
<211> LENGTH: 22
<212> TYPE: PRT
<213> ORGANISM: Canis familiaris

<400> SEQUENCE: 129

Pro Lys Arg Glu Asn Gly Arg Val Pro Arg Pro Pro Asp Cys Pro Lys
1               5                   10                  15

Cys Pro Ala Pro Glu Met
            20


<210> SEQ ID NO 130
<211> LENGTH: 20
<212> TYPE: PRT
<213> ORGANISM: Canis familiaris

<400> SEQUENCE: 130

Ala Lys Glu Cys Glu Cys Lys Cys Asn Cys Asn Asn Cys Pro Cys Pro
1               5                   10                  15

Gly Cys Gly Leu
            20


<210> SEQ ID NO 131
<211> LENGTH: 17
<212> TYPE: PRT
<213> ORGANISM: Artificial Sequence
<220> FEATURE:
<223> OTHER INFORMATION: genetically modified canis familiarus

<400> SEQUENCE: 131

Pro Lys Glu Ser Thr Cys Lys Cys Ile Pro Pro Cys Pro Val Pro Glu
1               5                   10                  15

Ser


<210> SEQ ID NO 132
<211> LENGTH: 31
<212> TYPE: PRT
<213> ORGANISM: Canis familiaris
```

<400> SEQUENCE: 132

Ala Glu Val Arg Val Thr Val Leu Arg Gln Ala Gly Ser Gln Met Thr
1 5 10 15

Glu Val Cys Ala Ala Thr Tyr Thr Val Glu Asp Glu Leu Ala Phe
20 25 30

<210> SEQ ID NO 133
<211> LENGTH: 21
<212> TYPE: PRT
<213> ORGANISM: Canis familiaris

<400> SEQUENCE: 133

Tyr Ile Cys Lys Val Glu Leu Met Tyr Pro Pro Pro Tyr Tyr Val Gly
1 5 10 15

Met Gly Asn Gly Thr
20

<210> SEQ ID NO 134
<211> LENGTH: 8
<212> TYPE: PRT
<213> ORGANISM: Canis familiaris

<400> SEQUENCE: 134

Thr Val Leu Arg Gln Ala Gly Ser
1 5

<210> SEQ ID NO 135
<211> LENGTH: 5
<212> TYPE: PRT
<213> ORGANISM: Canis familiaris

<400> SEQUENCE: 135

Ala Thr Tyr Thr Val
1 5

<210> SEQ ID NO 136
<211> LENGTH: 13
<212> TYPE: PRT
<213> ORGANISM: Canis familiaris

<400> SEQUENCE: 136

Tyr Ile Cys Lys Val Glu Leu Met Tyr Pro Pro Pro Tyr
1 5 10

<210> SEQ ID NO 137
<211> LENGTH: 6
<212> TYPE: PRT
<213> ORGANISM: Canis familiaris

<400> SEQUENCE: 137

Met Tyr Pro Pro Pro Tyr
1 5

<210> SEQ ID NO 138
<211> LENGTH: 186
<212> TYPE: PRT
<213> ORGANISM: Canis familiaris

<400> SEQUENCE: 138

Met His Val Ala Gln Pro Ala Val Val Leu Ala Ser Ser Arg Gly Val
1 5 10 15

-continued

```
Ala Ser Phe Val Cys Glu Tyr Gly Ser Ser Gly Asn Ala Ala Glu Val
            20                  25                  30

Arg Val Thr Val Leu Arg Gln Ala Gly Ser Gln Met Thr Glu Val Cys
        35                  40                  45

Ala Ala Thr Tyr Thr Val Glu Asp Glu Leu Ala Phe Leu Asp Asp Ser
    50                  55                  60

Thr Cys Thr Gly Thr Ser Ser Gly Asn Lys Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Val Gly Met Gly Asn Gly Thr Gln Ile
            100                 105                 110

Tyr Val Ile Asp Pro Glu Pro Cys Pro Asp Ser Asp Phe Leu Leu Trp
        115                 120                 125

Ile Leu Ala Ala Val Ser Ser Gly Leu Phe Phe Tyr Ser Phe Leu Ile
    130                 135                 140

Thr Ala Val Ser Leu Ser Lys Met Leu Lys Lys Arg Ser Pro Leu Thr
145                 150                 155                 160

Thr Gly Val Tyr Val Lys Met Pro Pro Thr Glu Pro Glu Cys Glu Lys
                165                 170                 175

Gln Phe Gln Pro Tyr Phe Ile Pro Ile Asn
            180                 185
```

CANINIZED ANTIBODIES AGAINST CANINE CTLA-4

CROSS-REFERENCE TO RELATED APPLICATIONS

This application is a National Stage application of International Patent Application No. PCT/EP2020/069923, filed Jul. 15, 2020, which claims priority under 35 U.S.C. § 119 (e) of provisional applications U.S. Ser. No. 62/874,287, filed on Jul. 15, 2019, U.S. Ser. No. 62/926,047, filed on Oct. 25, 2019, and U.S. Ser. No. 63/048,873 filed on Jul. 7, 2020, the contents of U.S. Ser. No. 62/874,287, U.S. Ser. No. 62/926,047 and U.S. Ser. No. 63/048,873 are hereby incorporated by reference in their entireties.

SEQUENCE LISTING

This application incorporates by reference in its entirety the Computer Readable Form (CRF) of a Substitute Sequence Listing in ASCII text format submitted via Patent Center. The Substitute Sequence Listing text file submitted via Patent Center is entitled "14463-250-999_SUB_SL.txt," was created on Mar. 10, 2025, and is 177,205 bytes in size.

FIELD OF THE INVENTION

The present invention relates to antibodies to proteins involved in co-stimulatory or co-inhibitory signaling pathways, including CTLA-4. More particularly, the present invention further relates to caninized antibodies to canine CTLA-4 that have specific sequences and a high binding affinity for canine CTLA-4. The present invention also relates to use of the antibodies of the present invention in the treatment of cancer in canines.

BACKGROUND OF THE INVENTION

The initiation or termination of immune responses is mediated via signaling pathways that are activated by complex interactions between a set of proteins expressed on the surface of many immune cells, most notably T lymphocytes and antigen presenting cells (APCs). Co-stimulatory signaling pathways lead to the development of immune responses and have been shown to be mediated most importantly through the interaction of CD28 on the surface of T cells and B7.1 (also known as CD80) and B7.2 (also known as CD86) family members on the surface of APCs. B7.1 and B7.2 are thought to perform similar functions.

In contrast, co-inhibitory pathways lead to the inhibition or termination of the immune responses and have been shown to be mediated via the interaction between Cytotoxic T-Lymphocyte-Associated protein 4 (CTLA-4) on T cells and CD80/CD86 proteins on APCs. Additional co-inhibitory signaling pathways have been shown to be mediated via the interaction between programmed cell death receptor 1 (PD-1) on T cells and programmed cell death receptor ligands 1 or 2 (PD-L1/PD-L2) proteins on APCs. Furthermore, it has also been shown that the interaction between PD-L1 and CD80 can also result in inhibitory signals in T cells.

CD80 and CD86 are members of the immunoglobulin (Ig) superfamily [Sharpe and Freeman, *Nature Reviews,* 2:116-126 (2002)]. CD80 is expressed on activated B cells, activated T cells, as well as macrophages, and dendritic cells [Swanson and Hall, *Eur J. Immunol.,* 23:295-298 (1993); Razi-Wolfe et al., *PNAS,* 89:4210-4214 (1992)]. CD86 is constitutively expressed on dendritic cells, Langerhans cells, and B cells. In addition, CD86 is expressed on monocytes and is up-regulated following IFN-gamma stimulation [Larsen et al., *Immunol,* 152:5208-5219 (1994); Inaba, *J. Exp. Med.* 180:1849-1860 (1994)].

CD80 and CD86 bind CD28 and CTLA-4 with different functional consequences [Linsley et al., *PNAS,* 87:5031-5035 (1990); Linsley et al., *J. Exp. Med.,* 173:721-730 (1991); Azuma et al., *Nature* 366:76-79 (1993); Freeman et al., *Science* 262:909-912 (1993)]. The binding of CD80 and CD86 to CTLA-4 has a much higher affinity than the binding of CD80/CD86 to CD28 [van der Merwe, *J. Exp. Med.* 185:393-402 (1997)].

CD28 is a homodimeric glycoprotein that is a member of the Ig superfamily [Aruffo and Seed, *PNAS,* 84:8573-8577 (1987)]. The mature protein has a single extracellular variable domain of 134 amino acid residues containing a hexapeptide motif MYPPPY that is essential for counter receptor binding [Riley and June, *Blood,* 105:13-21 (2005)]. The 41-amino acid cytoplasmic domain of CD28 contains four tyrosine residues that can be phosphorylated upon activation [Sharpe and Freeman, *Nat. Rev. Immunol.,* 2:116-126 (2002)]. CD28 is expressed on the majority of $CD4^{+}$ T cells and about 50% of $CD8^{+}$ T cells [Gross et al., *J. Immunol.,* 149:380-388 (1992); Riley and June, *Blood,* 105:13-21 (2005)]. After T cell receptor (TCR) ligation, B7.1/B7.2 binding to CD28 provides a critical co-stimulatory signal to the T cell allowing for T cell activation and subsequent development of the immune response [Reiser et al., *PNAS,* 89:271-275 (1992); Jenkins et al., *J. Immunol.,* 147:2461-2466 (1991)]. It has been shown that in the absence of CD28 signal, the T cells undergo apoptosis or enter a state of unresponsiveness [Jenkins et al., *J. Exp. Med.* 165:302-319 (1987); Jenkins et al., *PNAS,* 84:5409-5413 (1987); *Schwartz, Science,* 248:1349-1356 (1990)]. CD28-B7.1/B7.2 binding can alter the threshold level of TCR ligation (e.g., the amount of antigen-MHC complex) required for activation, reduce the time needed to stimulate naïve cells and enhance the magnitude of the T cell response [Soskic et al., *Advances in Immunology,* 124:96-123 (2014)].

CTLA-4 (CD152) is also a member of the Ig superfamily and consists of a single extracellular domain, a transmembrane domain and a short cytoplasmic tail [Swanson, Immunology; 1010:169-177 (2000)]. In addition, CTLA-4 shares about 30% amino acid identity with CD28. CTLA-4 is not constitutively expressed on naïve T cells, although it is rapidly up-regulated soon after CD28 ligation and T cell activation with a peak expression level of CTLA-4 at about 48-96 hours after the initial T cell activation [Alegre et al., *J. Immunol.,* 157:4762-4770 (1996); Freeman et al., *J. Immunol.,* 149:3795-3801 (1992)]. CTLA-4 binds to both B7.1 and B7.2 with a much higher affinity than CD28 [van der Merwe et al., *J. Exp. Med.,* 185:393-402 (1997)]. However, in contrast to the stimulatory effects of CD28 binding B7.1 or B7.2, CTLA-4 acts as an inhibitory receptor that is vital for down-modulation of the immune response [Walnus et al., *Immunity,* 1:405-413 (1994); Walnus, *J. Exp. Med.,* 183:2541-2550 (1996); Krummel and Allison, *J. Exp. Med.,* 183:2533-2540 (1996)]. The mechanism by which CTLA-4 mediates its immune inhibitory functions are related to its capacity to act as a competitive inhibitor of the interaction between CD28 and CD80/CD86 [reviewed in Swanson, Immunology, 1010:169-177 (2000)]. The critical role of CTLA-4 in immune down-regulation is demonstrated in CTLA-4 deficient mice, which die by 3-5 weeks of age because of the development of a lymphoproliferative disease characterized by T cell infiltration of multiple organs [Tivol et al., *Immunity,* 3:541-5417 (1995); Waterhouse et al.,

*Science,* 270:985-988 (1995)]. It was also demonstrated that the consequences of CTLA-4 knockout is dependent on the interaction of CD28 with its ligands CD80 and CD86 as shown by the lack of disease in the CTLA-4/CD80/CD86 triple knockout mice [Mandelbrot et al., *J. Exp. Med.,* 189:435-440 (1999)]. This is also confirmed by the protection against lymphoproliferation afforded by repeated administration of CTLA-4 Ig in CTLA-4 knockout mice [Tivol et al., *J Immunol.,* 158:5091-5094 (1997)].

In addition, blocking the effect of CTLA-4 with antibodies has been shown to enhance in vitro and in vivo T cell responses and to increase anti-tumor immune responses [Leach et al., *Science,* 271:1734-1736 (1996)]. Based on these findings, the development of CTLA-4 blockers such as monoclonal antibodies were undertaken to provide therapeutic modalities for treatment of cancer [Hodi et al., *PNAS,* 100(8):4712-4717 (2003); Phan G Q et al., *PNAS,* 100(14): 8372-8377 (2003); Attia, *Journal of Clinical Oncology,* 23(25):6043-6053 (2005); Comin-Anduix et al., *Journal of Translational Medicine,* 6:22-22 (2008); WO2000037504 A2; U.S. Pat. No. 8,017,114 B2; WO2010097597A1; WO2012120125 A1; and Boutros et al., *Nat Rev Clin Oncol.,* 13(8):473-486 (2016)].

PD-1 is a member of the CD28/CTLA-4 family of immune modulatory receptors. PD-1 is also a member of the Ig superfamily and contains an extracellular variable domain that binds its ligands and a cytoplasmic tail that binds signaling molecules [reviewed in Zak et al., *Cell Structure,* 25:1163-1174 (2017)]. The cytoplasmic tail of PD-1 contains two tyrosine-based signaling motifs [Zhang et al., *Immunity* 20:337-347 (2004)]. PD-1 expression is not found on unstimulated T cells, B cells, or myeloid cells. However, PD-1 expression is up-regulated on these cells following activation [Chemnitz et al., *J. Immunol.,* 173:945-954 (2004); Petrvas et al., *J. Exp. Med.,* 203:2281-2292 (2006)]. PD-1 is most closely related to CTLA-4, sharing approximately 24% amino acid identity [Jin et al., *Current Topics in Microbiology and Immunology,* 350:17-37 (2010)]. PD-1 attenuates T cell activation when bound to PD-L1 and PD-L2, which are expressed on the surface of APCs. The binding of either of these ligands to PD-1 negatively regulates antigen signaling via the T cell receptor (TCR). To date, only PD-L1 and PD-L2 have been found to function as ligands for PD-1. As with CTLA-4, PD-1 ligation appears to transmit a negative immunomodulatory signal. Ligation of PD-1 by PD-L1 or PD-L2 results in the inhibition of TCR-mediated proliferation and cytokine production [Jin et al., *Current Topics in Microbiology and Immunology,* 350: 17-37 (2010)]. In contrast to CTLA-4 deficient animals, PD-1 deficient mice die much later in life and display signs of autoimmunity although the severity of the observed effects is not as profound as those exhibited by CTLA-4 deficient animals [Nishimura et al., *Immunity,* 11(2):141-151 (1999); Nishimura et al., *Science,* 291(5502):319-322 (2001)]. Although the PD-1 signaling pathways are currently under intense investigation, research to date suggests that the PD-L1/PD-L2/PD-1 interactions are involved in the negative regulation of some immune responses because of diminishing the signals downstream of TCR stimulation leading to decreased cytokine secretion and impairment of T cell proliferation and decrease in the production of cytotoxic molecules by T cells [Freeman et al., *J. Exp. Med.,* 192 (7):1027-1034 (2000)].

PD-L1 (CD274) is a type 1 membrane protein and consists of IgV-like and IgC-like extracellular domains, a hydrophobic transmembrane domain, and a short cytoplasmic tail made from 30 amino acids, with unknown signal transduction properties. PD-L1 is recognized as a member of the B7 family and shares approximately 20% amino acid identity with B7 family members. PD-L1 binds to its receptor, PD-1, found on activated T cells, B cells, and myeloid cells. PD-L1 also binds to the costimulatory molecule CD80, but not to CD86 [Butte et al., *Immunology,* 45 (13):3567-3572 (2008)]. The affinity of CD80 for PD-L1 is intermediate between its affinities for CD28 and CTLA-4. The related molecule PD-L2 has no affinity for either CD80 or CD86, but shares PD-1 as a receptor. Engagement of PD-L1 with its receptor PD-1 on T cells delivers a signal that inhibits TCR-mediated IL-2 production and T cell proliferation. PD-L1 binding to PD-1 also contributes to ligand-induced TCR down-modulation during antigen presentation to naive T cells. Additionally, PD-L1 binding to CD80 on T cells leads to T cell apoptosis. The role of PD-1 and PD-L1 as inhibitors of T cell activation has been demonstrated in many studies. Based on these findings, the development of PD-1 and PD-L1 blockers such as monoclonal antibodies, were undertaken to provide therapeutic modalities for treatment of cancer and infectious diseases.

Humanized monoclonal antibodies that block the binding and activity of canine PD-1, PD-L1, and CTLA-4 have been developed and are currently available for use in the treatment of human subjects diagnosed with one of several different types of cancer. Similarly, caninized monoclonal antibodies that block the binding and activity of canine PD-1 and PD-L1 have also been reported [U.S. Pat. No. 9,944,704 B2, U.S. Pat. No. 10,106,607 B2, and U.S.2018/0237535 A1, the contents of which are hereby incorporated by reference in their entireties]. However, heretofore there have been no reports of a caninized monoclonal antibody that blocks the binding and activity of canine CTLA-4.

The citation of any reference herein should not be construed as an admission that such reference is available as "prior art" to the instant application.

SUMMARY OF THE INVENTION

The present invention relates to anti-canine Cytotoxic T-Lymphocyte-Associated protein 4 (CTLA-4) antibodies that bind canine CTLA-4. In particular embodiments, the antibodies to canine CTLA-4 bind canine CTLA-4 with specificity. In more particular embodiments, the antibodies to canine CTLA-4 also have the ability to block the binding of canine CTLA-4 with canine CD80. In other particular embodiments, the antibodies to canine CTLA-4 also have the ability to block the binding of canine CTLA-4 with canine CD86. In still other particular embodiments, the antibodies to canine CTLA-4 have the ability to both block the binding of canine CTLA-4 with canine CD80 and to block the binding of canine CTLA-4 with canine CD86.

Moreover, the present invention relates to the complementary determining regions (CDRs) comprised by these antibodies and the combination of these CDRs (e.g., obtained from murine anti-canine CTLA-4 antibodies) into canine frames to form caninized anti-canine CTLA-4 antibodies. The present invention also relates to use of such antibodies in the treatment of conditions such as cancer.

Accordingly, the present invention provides unique sets of CDRs from six (6) exemplified murine anti-canine CTLA-4 antibodies. The six exemplified murine anti-canine CTLA-4 antibodies have unique sets of CDRs, i.e., three light chain CDRs: CDR light 1 (CDRL1), CDR light 2 (CDRL2), and CDR light 3 (CDRL3) and three heavy chain CDRs: CDR heavy 1 (CDRH1), CDR heavy 2 (CDRH2) and CDR heavy 3 (CDRH3). As detailed below, there is substantial sequence homology within each group of CDRs, and even some redundancy (e.g., see, the set of VL CDR-3's below in Table 1). Therefore, the present invention not only provides the amino acid sequences of the six CDRs from the six exemplified murine anti-canine CTLA-4 antibodies, but further provides conservatively modified variants of these CDRs, as well as variants that comprise (e.g., share) the same canonical structure and/or bind to one or more (e.g., 1, 2, 3, 4, or more) amino acid residues of canine CTLA-4 that are comprised by an epitope of canine CTLA-4.

One aspect of the present invention provides mammalian antibodies that bind canine Cytotoxic T-Lymphocyte-Associated protein 4 (CTLA-4). In particular embodiments, a mammalian antibody or antigen binding fragment thereof of the present invention is a murine antibody. In preferred embodiments, the mammalian antibodies of the present invention, including murine antibodies of the present invention, or antigen binding fragments thereof are caninized antibodies or a caninized antigen binding fragment thereof.

In particular embodiments, the mammalian antibodies bind canine CTLA-4 with specificity. In more particular embodiments, the mammalian antibodies to canine CTLA-4 also have the ability to block the binding of canine CTLA-4 with canine CD80. In other particular embodiments, the mammalian antibodies to canine CTLA-4 also have the ability to block the binding of canine CTLA-4 with canine CD86. In still other particular embodiments, the mammalian antibodies to canine CTLA-4 have the ability to both block the binding of canine CTLA-4 with canine CD80 and to block the binding of canine CTLA-4 with canine CD86.

In certain embodiments the mammalian antibodies that bind canine CTLA-4 are isolated antibodies. The present invention further provides antigenic binding fragments of any of these mammalian antibodies that bind canine CTLA-4. In particular embodiments the antibodies comprises three light chain complementary determining regions (CDRs): CDR light 1 (CDRL1), CDR light 2 (CDRL2), and CDR light 3 (CDRL3); and three heavy chain CDRs: CDR heavy 1 (CDRH1), CDR heavy 2 (CDRH2) and CDR heavy 3 (CDRH3).

In particular embodiments, the mammalian antibody or an antigen binding fragment thereof comprises a CDRH3 that comprises the amino acid sequence of SEQ ID NO: 90, a conservatively modified variant of the amino acid sequence of SEQ ID NO: 90, or a variant of SEQ ID NO: 90 that comprises the canonical structure class of 7. In more particular embodiments, the mammalian antibody or an antigen binding fragment thereof further comprises a CDRH2 that comprises the amino acid sequence of SEQ ID NO: 88, a conservatively modified variant of the amino acid sequence of SEQ ID NO: 88, or a variant of SEQ ID NO: 88 that comprises the canonical structure class of 2A. In even more particular embodiments, the mammalian antibody or an antigen binding fragment thereof also further comprises a CDRH1 that comprises the amino acid sequence of SEQ ID NO: 86, a CDRH1 that comprises a conservatively modified variant of the amino acid sequence of SEQ ID NO: 86, or a variant of SEQ ID NO: 86 that comprises the canonical structure class of 1. In still more particular embodiments, the mammalian antibody or an antigen binding fragment thereof also further comprises a CDRL3 that comprises the amino acid sequence of SEQ ID NO: 96, a conservatively modified variant of the amino acid sequence of SEQ ID NO: 96, or a variant of SEQ ID NO: 96 that comprises the canonical structure class of 1. In yet more particular embodiments, the mammalian antibody or an antigen binding fragment thereof further comprises a CDRL2 that comprises the amino acid sequence of SEQ ID NO: 94, a conservatively modified variant of the amino acid sequence of SEQ ID NO: 94, or a variant of SEQ ID NO: 94 that comprises the canonical structure class of 1. In even more particular embodiments, the mammalian antibody or an antigen binding fragment thereof also further comprises a CDRL1 that comprises the amino acid sequence of SEQ ID NO: 92, a conservatively modified variant of the amino acid sequence of SEQ ID NO: 92, or a variant of SEQ ID NO: 92 that comprises the canonical structure class of 4.

In alternative embodiments, the mammalian antibody or an antigen binding fragment thereof comprises a CDRH3 that comprises the amino acid sequence of SEQ ID NO: 102, a conservatively modified variant of the amino acid sequence of SEQ ID NO: 102, or a variant of SEQ ID NO: 102 that comprises the canonical structure class of 9. In more particular embodiments, the mammalian antibody or an antigen binding fragment thereof further comprises a CDRH2 that comprises the amino acid sequence of SEQ ID NO: 100, a conservatively modified variant of the amino acid sequence of SEQ ID NO: 100, or a variant of SEQ ID NO: 100 that comprises the canonical structure class of 4. In even more particular embodiments, the mammalian antibody or an antigen binding fragment thereof also further comprises a CDRH1 that comprises the amino acid sequence of SEQ ID NO: 98, a CDRH1 that comprises a conservatively modified variant of the amino acid sequence of SEQ ID NO: 98, or a variant of SEQ ID NO: 98 that comprises the canonical structure class of 1. In still more particular embodiments, the mammalian antibody or an antigen binding fragment thereof also further comprises a CDRL3 that comprises the amino acid sequence of SEQ ID NO: 108, a conservatively modified variant of the amino acid sequence of SEQ ID NO: 108, or a variant of SEQ ID NO: 108 that comprises the canonical structure class of 1. In yet more particular embodiments, the mammalian antibody or an antigen binding fragment thereof also further comprises a CDRL2 that comprises the amino acid sequence of SEQ ID NO: 106, a conservatively modified variant of the amino acid sequence of SEQ ID NO: 106, or a variant of SEQ ID NO: 106 that comprises the canonical structure class of 1. In even more particular embodiments, the mammalian antibody or an antigen binding fragment thereof also further comprises a CDRL1 that comprises the amino acid sequence of SEQ ID NO: 104, a conservatively modified variant of the amino acid sequence of SEQ ID NO: 104, or a variant of SEQ ID NO: 104 that comprises the canonical structure class of 1.

In other alternative embodiments, the mammalian antibody or an antigen binding fragment thereof comprises a CDRH3 that comprises the amino acid sequence of SEQ ID NO: 113, a conservatively modified variant of the amino acid sequence of SEQ ID NO: 113, or a variant of SEQ ID NO: 113 that comprises the canonical structure class of 7. In more particular embodiments, the mammalian antibody or an antigen binding fragment thereof further comprises a CDRH2 that comprises the amino acid sequence of SEQ ID NO: 88, a conservatively modified variant of the amino acid sequence of SEQ ID NO: 88, or a variant of SEQ ID NO: 88 that comprises the canonical structure class of 2A. In even more particular embodiments, the mammalian antibody or an antigen binding fragment thereof also further comprises a CDRH1 that comprises the amino acid sequence of SEQ ID NO: 86, a CDRH1 that comprises a conservatively modified variant of the amino acid sequence of SEQ ID NO: 86, or a variant of SEQ ID NO: 86 that comprises the canonical structure class of 1. In still more particular embodiments, the mammalian antibody or an antigen binding fragment thereof also further comprises a CDRL3 that comprises the amino acid sequence of SEQ ID NO: 96, a conservatively modified variant of the amino acid sequence of SEQ ID NO: 96, or a variant of SEQ ID NO: 96 that comprises the canonical structure class of 1. In yet more particular embodiments, the mammalian antibody or an antigen binding fragment thereof also further comprises a CDRL2 that comprises the amino acid sequence of SEQ ID NO: 94, a conservatively modified variant of the amino acid sequence of SEQ ID NO: 94, or a variant of SEQ ID NO: 94 that comprises the canonical structure class of 1. In even more particular embodiments, the mammalian antibody or an antigen binding fragment thereof also further comprises a CDRL1 that comprises the amino acid sequence of SEQ ID NO: 117, a conservatively modified variant of the amino acid sequence of SEQ ID NO: 117, or a variant of SEQ ID NO: 117 that comprises the canonical structure class of 4.

In yet other alternative embodiments, the mammalian antibody or an antigen binding fragment thereof comprises a CDRH3 that comprises the amino acid sequence of SEQ ID NO: 115, a conservatively modified variant of the amino acid sequence of SEQ ID NO: 115, or a variant of SEQ ID NO: 115 that comprises the canonical structure class of 7. In more particular embodiments, the mammalian antibody or an antigen binding fragment thereof further comprises a CDRH2 that comprises the amino acid sequence of SEQ ID NO: 88, a conservatively modified variant of the amino acid sequence of SEQ ID NO: 88, or a variant of SEQ ID NO: 88 that comprises the canonical structure class of 2A. In even more particular embodiments, the mammalian antibody or an antigen binding fragment thereof also further comprises a CDRH1 that comprises the amino acid sequence of SEQ ID NO: 86, a CDRH1 that comprises a conservatively modified variant of the amino acid sequence of SEQ ID NO: 86, or a variant of SEQ ID NO: 86 that comprises the canonical structure class of 1. In still more particular embodiments, the mammalian antibody or an antigen binding fragment thereof also further comprises a CDRL3 that comprises the amino acid sequence of SEQ ID NO: 96, a conservatively modified variant of the amino acid sequence of SEQ ID NO: 96, or a variant of SEQ ID NO: 96 that comprises the canonical structure class of 1. In yet more particular embodiments, the mammalian antibody or an antigen binding fragment thereof also further comprises a CDRL2 that comprises the amino acid sequence of SEQ ID NO: 122, a conservatively modified variant of the amino acid sequence of SEQ ID NO: 122, or a variant of SEQ ID NO: 122 that comprises the canonical structure class of 1. In even more particular embodiments, the mammalian antibody or an antigen binding fragment thereof also further comprises a CDRL1 that comprises the amino acid sequence of SEQ ID NO: 119, a conservatively modified variant of the amino acid sequence of SEQ ID NO: 119, or a variant of SEQ ID NO: 119 that comprises the canonical structure class of 4.

In still other alternative embodiments, the mammalian antibody or an antigen binding fragment thereof comprises a CDRH3 that comprises the amino acid sequence of SEQ ID NO: 114, a conservatively modified variant of the amino acid sequence of SEQ ID NO: 114, or a variant of SEQ ID NO: 114 that comprises the canonical structure class of 7. In more particular embodiments, the mammalian antibody or an antigen binding fragment thereof further comprises a CDRH2 that comprises the amino acid sequence of SEQ ID NO: 111, a conservatively modified variant of the amino acid sequence of SEQ ID NO: 111, or a variant of SEQ ID NO: 111 that comprises the canonical structure class of 2A. In even more particular embodiments, the mammalian antibody or an antigen binding fragment thereof also further comprises a CDRH1 that comprises the amino acid sequence of SEQ ID NO: 109, a CDRH1 that comprises a conservatively modified variant of the amino acid sequence of SEQ ID NO: 109, or a variant of SEQ ID NO: 109 that comprises the canonical structure class of 1. In still more particular embodiments, the mammalian antibody or an antigen binding fragment thereof also further comprises a CDRL3 that comprises the amino acid sequence of SEQ ID NO: 96, a conservatively modified variant of the amino acid sequence of SEQ ID NO: 96, or a variant of SEQ ID NO: 96 that comprises the canonical structure class of 1. In yet more particular embodiments, the mammalian antibody or an antigen binding fragment thereof also further comprises a CDRL2 that comprises the amino acid sequence of SEQ ID NO: 121, a conservatively modified variant of the amino acid sequence of SEQ ID NO: 121, or a variant of SEQ ID NO: 121 that comprises the canonical structure class of 1. In even more particular embodiments, the mammalian antibody or an antigen binding fragment thereof also further comprises a CDRL1 that comprises the amino acid sequence of SEQ ID NO: 118, a conservatively modified variant of the amino acid sequence of SEQ ID NO: 118, or a variant of SEQ ID NO: 118 that comprises the canonical structure class of 4.

In yet other alternative embodiments, the mammalian antibody or an antigen binding fragment thereof comprises a CDRH3 that comprises the amino acid sequence of SEQ ID NO: 116, a conservatively modified variant of the amino acid sequence of SEQ ID NO: 116, or a variant of SEQ ID NO: 116 that comprises the canonical structure class of 12. In more particular embodiments, the mammalian antibody or an antigen binding fragment thereof further comprises a CDRH2 that comprises the amino acid sequence of SEQ ID NO: 112, a conservatively modified variant of the amino acid sequence of SEQ ID NO: 112, or a variant of SEQ ID NO: 112 that comprises the canonical structure class of 2A. In even more particular embodiments, the mammalian antibody or an antigen binding fragment thereof also further comprises a CDRH1 that comprises the amino acid sequence of SEQ ID NO: 110, a CDRH1 that comprises a conservatively modified variant of the amino acid sequence of SEQ ID NO: 110, or a variant of SEQ ID NO: 110 that comprises the canonical structure class of 1. In still more particular embodiments, the mammalian antibody or an antigen binding fragment thereof also further comprises a CDRL3 that comprises the amino acid sequence of SEQ ID NO: 124, a conservatively modified variant of the amino acid sequence of SEQ ID NO: 124, or a variant of SEQ ID NO: 124 that comprises the canonical structure class of 1. In yet more particular embodiments, the mammalian antibody or an antigen binding fragment thereof also further comprises a CDRL2 that comprises the amino acid sequence of SEQ ID NO: 123, a conservatively modified variant of the amino acid sequence of SEQ ID NO: 123, or a variant of SEQ ID NO: 123 that comprises the canonical structure class of 1. In even more particular embodiments, the mammalian antibody or an antigen binding fragment thereof also further comprises a CDRL1 that comprises the amino acid sequence of SEQ ID NO: 120, a conservatively modified variant of the amino acid sequence of SEQ ID NO: 120, or a variant of SEQ ID NO: 120 that comprises the canonical structure class of 2.

As indicated above, caninized antibodies to canine CTLA-4 or caninized antigen binding fragments thereof are an important aspect of the present invention and the present invention provides caninized mammalian antibodies, including caninized murine antibodies, of all of such mammalian antibodies. Accordingly, the present invention also provides an isolated caninized antibody or antigen binding fragment thereof that specifically binds CTLA-4 comprising a canine IgG heavy chain and a canine kappa or lambda light chain. In particular embodiments of this type, the canine kappa or lambda light chain comprises three light chain complementary determining regions (CDRs): CDR light 1 (CDRL1), CDR light 2 (CDRL2), and CDR light 3 (CDRL3); and the canine IgG heavy chain comprises three heavy chain CDRs: CDR heavy 1 (CDRH1), CDR heavy 2 (CDRH2) and CDR heavy 3 (CDRH3) that are obtained from murine anti-canine CTLA-4 antibodies. Particular embodiments of the caninized antibodies and antigen binding fragments thereof of the present invention bind canine CTLA-4 and/or block the binding of canine CTLA-4 to canine CD80 and/or to canine CD86.

A caninized antibody of the present invention or caninized antigen binding fragment thereof, can comprise a IgGD that comprises a hinge region that comprises the amino acid sequence of SEQ ID NO: 128. In a related embodiment, the hinge region comprises the amino acid sequence of SEQ ID NO: 129. In yet another related embodiment, the hinge region comprises the amino acid sequence of SEQ ID NO: 130. In still another related embodiment, the hinge region comprises the amino acid sequence of SEQ ID NO: 131.

In alternative embodiments, a caninized antibody comprises a heavy chain that comprises the amino acid sequence of SEQ ID NO: 62. In specific embodiments of this type, the heavy chain is encoded by the nucleotide sequence of SEQ ID NO: 61. In other embodiments, a caninized antibody comprises a heavy chain that comprises the amino acid sequence of SEQ ID NO: 64. In specific embodiments of this type, the heavy chain is encoded by the nucleotide sequence of SEQ ID NO: 63. In still other embodiments, a caninized antibody comprises a heavy chain that comprises the amino acid sequence of SEQ ID NO: 66. In specific embodiments of this type, the heavy chain is encoded by the nucleotide sequence of SEQ ID NO: 65. In more particular embodiments, the caninized antibody further comprises a light chain that comprises the amino acid sequence of SEQ ID NO: 50. In specific embodiments of this type, the light chain is encoded by the nucleotide sequence of SEQ ID NO: 49. In other particular embodiments, the caninized antibody further comprises a light chain that comprises the amino acid sequence of SEQ ID NO: 52. In specific embodiments of this type, the light chain is encoded by the nucleotide sequence of SEQ ID NO: 51. In still other particular embodiments, the caninized antibody further comprises a light chain that comprises the amino acid sequence of SEQ ID NO: 54. In specific embodiments of this type, the light chain is encoded by the nucleotide sequence of SEQ ID NO: 53.

In alternative embodiments, a caninized antibody comprises a modified heavy chain that comprises the amino acid sequence of SEQ ID NO: 74. In specific embodiment of this type, the modified heavy chain is encoded by the nucleotide sequence of SEQ ID NO: 73. In other embodiments, a caninized antibody comprises a modified heavy chain that comprises the amino acid sequence of SEQ ID NO: 76. In specific embodiment of this type, the modified heavy chain is encoded by the nucleotide sequence of SEQ ID NO: 75. In yet other embodiments, a caninized antibody comprises a modified heavy chain that comprises the amino acid sequence of SEQ ID NO: 78. In specific embodiments of this type, the modified heavy chain is encoded by the nucleotide sequence of SEQ ID NO: 77. In more particular embodiments, the caninized antibody further comprises a light chain that comprises the amino acid sequence of SEQ ID NO: 50. In specific embodiment of this type, the light chain is encoded by the nucleotide sequence of SEQ ID NO: 49. In other particular embodiments, the caninized antibody further comprises a light chain that comprises the amino acid sequence of SEQ ID NO: 52. In specific embodiment of this type, the light chain is encoded by the nucleotide sequence of SEQ ID NO: 51. In still other particular embodiments, the caninized antibody further comprises a light chain that comprises the amino acid sequence of SEQ ID NO: 54. In specific embodiment of this type, the light chain is encoded by the nucleotide sequence of SEQ ID NO: 53.

In particular embodiments, the caninized antibodies comprise a heavy chain that comprises the amino acid sequence of SEQ ID NO: 66 and a light chain that comprises the amino acid sequence of SEQ ID NO: 52. In other embodiments, the caninized antibodies comprise a heavy chain that comprises the amino acid sequence of SEQ ID NO: 66 and a light chain that comprises the amino acid sequence of SEQ ID NO: 54.

In alternative embodiments, the caninized antibodies comprise a modified heavy chain that comprises the amino acid sequence of SEQ ID NO: 78 and a light chain that comprises the amino acid sequence of SEQ ID NO: 52. In other embodiments, the caninized antibodies comprise a modified heavy chain that comprises the amino acid sequence of SEQ ID NO: 78 and a light chain that comprises the amino acid sequence of SEQ ID NO: 54.

In other embodiments, a caninized antibody comprises a heavy chain that comprises the amino acid sequence of SEQ ID NO: 68. In specific embodiments of this type, the heavy chain is encoded by the nucleotide sequence of SEQ ID NO: 67. In other embodiments, a caninized antibody comprises a heavy chain that comprises the amino acid sequence of SEQ ID NO: 70. In specific embodiments of this type, the heavy chain is encoded by the nucleotide sequence of SEQ ID NO: 69. In still other embodiments, a caninized antibody comprises a heavy chain that comprises the amino acid sequence of SEQ ID NO: 72. In specific embodiments of this type, the heavy chain is encoded by the nucleotide sequence of SEQ ID NO: 71. In more particular embodiments, the caninized antibody further comprises a light chain that comprises the amino acid sequence of SEQ ID NO: 56. In specific embodiments of this type, the light chain is encoded by the nucleotide sequence of SEQ ID NO: 55. In other particular embodiments, the caninized antibody further comprises a light chain that comprises the amino acid sequence of SEQ ID NO: 58. In specific embodiments of this type, the light chain is encoded by the nucleotide sequence of SEQ ID NO: 57. In still other particular embodiments, the caninized antibody further comprises a light chain that comprises the amino acid sequence of SEQ ID NO: 60. In specific embodiments of this type, the light chain is encoded by the nucleotide sequence of SEQ ID NO: 59.

In alternative embodiments, a caninized antibody comprises a modified heavy chain that comprises the amino acid sequence of SEQ ID NO: 80. In specific embodiment of this type, the modified heavy chain is encoded by the nucleotide sequence of SEQ ID NO: 79. In other embodiments, a caninized antibody comprises a modified heavy chain that comprises the amino acid sequence of SEQ ID NO: 82. In specific embodiment of this type, the modified heavy chain is encoded by the nucleotide sequence of SEQ ID NO: 81. In yet other embodiments, a caninized antibody comprises a modified heavy chain that comprises the amino acid sequence of SEQ ID NO: 84. In specific embodiments of this type, the modified heavy chain is encoded by the nucleotide sequence of SEQ ID NO: 83. In more particular embodiments, the caninized antibody further comprises a light chain that comprises the amino acid sequence of SEQ ID NO: 56. In specific embodiments of this type, the light chain is encoded by the nucleotide sequence of SEQ ID NO: 55. In other particular embodiments, the caninized antibody further comprises a light chain that comprises the amino acid sequence of SEQ ID NO: 58. In specific embodiments of this type, the light chain is encoded by the nucleotide sequence of SEQ ID NO: 57. In still other particular embodiments, the caninized antibody further comprises a light chain that comprises the amino acid sequence of SEQ ID NO: 60. In specific embodiments of this type, the light chain is encoded by the nucleotide sequence of SEQ ID NO: 59.

In particular embodiments, the caninized antibodies comprise a modified heavy chain that comprises the amino acid sequence of SEQ ID NO: 72 and a light chain that comprises the amino acid sequence of SEQ ID NO: 58. In other embodiments, the caninized antibodies comprise a heavy chain that comprises the amino acid sequence of SEQ ID NO: 72 and a light chain that comprises the amino acid sequence of SEQ ID NO: 60.

In alternative embodiments, the caninized antibodies comprise a modified heavy chain that comprises the amino acid sequence of SEQ ID NO: 84 and a light chain that comprises the amino acid sequence of SEQ ID NO: 58. In other embodiments, the caninized antibodies comprise a modified heavy chain that comprises the amino acid sequence of SEQ ID NO: 84 and a light chain that comprises the amino acid sequence of SEQ ID NO: 60.

The present invention further provides mammalian antibodies or antigen binding fragments thereof that bind to canine CTLA-4 with a dissociation constant (Kd) that is lower than $1\times10^{-12}$ M (e.g., $5\times10^{-13}$ M, or lower). In other embodiments the mammalian antibodies or antigen binding fragments thereof bind to canine CTLA-4 with a dissociation constant of $1\times10^{-5}$ M to $1\times10^{-12}$ M. In more particular embodiments the mammalian antibodies or antigen binding fragments thereof bind to canine CTLA-4 with a dissociation constant of $1\times10^{-7}$ M to $1\times10^{-11}$ M. In still more particular embodiments the mammalian antibodies or antigen binding fragments thereof bind to canine CTLA-4 with a dissociation constant of $1\times10^{-8}$ M to $1\times10^{-11}$ M. In yet more particular embodiments the mammalian antibodies or antigen binding fragments thereof bind to canine CTLA-4 with a dissociation constant of $1\times10^{-8}$ M to $1\times10^{-10}$ M.

The present invention also provides mammalian antibodies or antigen binding fragments thereof that bind to canine CTLA-4 with an on rate ($k_0$) that is greater than $1\times10^{7}$ $M^{-1}s^{-1}$. In other embodiments the mammalian antibodies or antigen binding fragments thereof bind to canine CTLA-4 with an on rate of $1\times10^{2}$ $M^{-1}s^{-1}$ to $1\times10^{7}$ $M^{-1}s^{-1}$. In more particular embodiments the mammalian antibodies or antigen binding fragments thereof bind to canine CTLA-4 with an on rate of $1\times10^{3}$ $M^{-1}s^{-1}$ to $1\times10^{6}$ $M^{-1}s^{-1}$. In still more particular embodiments the mammalian antibodies or antigen binding fragments thereof bind to canine CTLA-4 with an on rate of $1\times10^{3}$ $M^{-1}s^{-1}$ to $1\times10^{5}$ $M^{-1}s^{-1}$. In yet more particular embodiments the mammalian antibodies or antigen binding fragments thereof bind to canine CTLA-4 on rate of $1\times10^{4}$ $M^{-1}s^{-1}$ to $1\times10^{5}$ $M^{-1}s^{-1}$.

The present invention further provides mammalian antibodies or antigen binding fragments thereof that bind to canine CTLA-4 with an off rate (kw) slower than $1\times10^{-7}$ $s^{-1}$. In other embodiments, the mammalian antibodies or antigen binding fragments thereof bind to canine CTLA-4 with an off rate of $1\times10^{-3}$ $s^{-1}$ to 1×10'$s^{-1}$. In more particular embodiments the mammalian antibodies or antigen binding fragments thereof bind to canine CTLA-4 with an off rate of $1\times10^{4}$ $s^{-1}$ to $1\times10^{-7}$ $s^{-1}$. In still more particular embodiments the mammalian antibodies or antigen binding fragments thereof bind to canine CTLA-4 with an off rate of $1\times10^{-5}s^{-1}$ to $1\times10^{-7}s^{-1}$.

In particular embodiments, a mammalian antibody of the present invention (including chimeric antibodies) blocks the binding of canine CD80 and/or CD86 with canine CTLA-4. In more particular embodiments the antibody blocks the binding of canine CD80 and/or CD86 with canine CTLA-4 with a minimum EC50 of $1\times10^{-8}$ M to $1\times10^{-9}$ M or an even lower concentration. In still more particular embodiments the EC50 is $5\times10^{-9}$ M to $5\times10^{-13}$ M. In still more particular embodiments the EC50 is between $5\times10^{-9}$ M and $5\times10^{-11}$ M. Accordingly, in particular embodiments, the antibodies of the present invention can exhibit one, two, three, four, or all these properties, i.e., the aforesaid dissociation constants with canine CTLA-4, the aforesaid on rates for binding with canine CTLA-4, the aforesaid off rates for dissociating from the antibody-canine CTLA-4 binding complex, or effective treating cancer in an animal subject.

The present invention further provides caninized mammalian antibodies and antigen-binding fragments that cross-compete with the mammalian antibodies disclosed herein. In particular embodiments, the caninized mammalian antibodies cross-compete with an antibody comprising the 6 CDRs of 45A9 [see, Table 1 below]. In related embodiments, the caninized mammalian antibodies cross-compete with an antibody comprising the 6 CDRs of 27G12 [see, Table 1 below]. In still other related embodiments, the caninized mammalian antibodies cross-compete with an antibody comprising the 6 CDRs of 22A11 [see, Table 1 below]. In yet other related embodiments, the caninized mammalian antibodies cross-compete with an antibody comprising the 6 CDRs of 110E3 [see, Table 1 below]. In specific embodiments, the caninized mammalian antibodies cross-compete with an antibody comprising the 6 CDRs of 12B3 [see, Tables 1 and 3 below]. In other specific embodiments, the caninized mammalian antibodies cross-compete with an antibody comprising the 6 CDRs of 39A11 [see, Tables 1 and 3 below]. In particular embodiments, the assay is a standard binding assay. In one such embodiment, the standard binding assay is performed with BIACore®. In another such embodiment, the standard binding assay is performed with an ELISA. In yet another such embodiment, the standard binding assay is performed by flow cytometry.

As indicated above, the antibodies (and antigen binding fragments thereof) of the present invention, including the aforesaid antibodies (and antigen binding fragments thereof), can be monoclonal antibodies (and antigen binding fragments thereof), mammalian antibodies (and antigen binding fragments thereof), e.g., murine (mouse) antibodies (and antigen binding fragments thereof), caninized antibodies (and antigen binding fragments thereof) including caninized murine antibodies (and antigen binding fragments thereof). In certain embodiments, the antibodies (and antigen binding fragments thereof) are isolated.

In preferred embodiments, a caninized antibody of the present invention or antigenic fragment thereof, binds to an epitope of the amino acid sequence of canine CTLA-4. In a particular embodiment, the caninized antibody interacts with one or more of the amino acid residue at positions T35, R38, T51, T53, Y90, K93, Y98 and Y102 of the amino acid sequence of SEQ ID NO: 138. In another embodiment the caninized antibody interacts with one or more of the amino acid residue at positions 35T, R38, S42, K93 and Y102 of the amino acid sequence of SEQ ID NO: 138.

The present invention further provides caninized antibodies that bind to one or more epitopes or portions thereof of the amino acid sequences of SEQ ID NO: 132, SEQ ID NO: 133, SEQ ID NO: 134, SEQ ID NO: 135, SEQ ID NO: 136, and SEQ ID NO: 137. In particular embodiments, a caninized antibody of the present invention or antigenic fragment thereof, binds to an epitope or a portion thereof comprised by the amino acid sequence of SEQ ID NO: 132. In a more particular embodiment of this type, the epitope or portion thereof is comprised by the amino acid sequence of SEQ ID NO: 134. In another embodiment of this type, the epitope or a portion thereof is comprised by the amino acid sequence of SEQ ID NO: 135. In certain embodiments, the epitope or a portion thereof is comprised by the amino acid sequence of SEQ ID NO: 133. In a more particular embodiment of this type, the epitope or portion thereof is comprised by the amino acid sequence of SEQ ID NO: 136. In related embodiments, the caninized antibodies bind to one or more epitopes or portions thereof that are comprised by the amino acid sequences of SEQ ID NO: 134 and/or SEQ ID NO: 136 and/or SEQ ID NO: 135.

The present invention further provides nucleic acids (including isolated and/or recombinant nucleic acids) that encode any one of the light chains of the caninized antibody of the present invention. Similarly, the present invention provides isolated nucleic acids (including isolated and/or recombinant nucleic acids) that encode any one of the heavy chains of the caninized antibody of the present invention.

The present invention further provides expression vectors that comprise one or more of the nucleic acids (including isolated nucleic acids) of the present invention. The present invention also provides host cells that comprise one or more expression vectors of the present invention.

In particular embodiments, the antibody is a recombinant antibody or an antigen binding fragment thereof. In related embodiments, the variable heavy chain domain and variable light chain domain are connected by a flexible linker to form a single-chain antibody. In particular embodiments, the antibody or antigen binding fragment is a Fab fragment. In other embodiments, the antibody or antigen binding fragment is a Fab' fragment. In yet other embodiments, the antibody or antigen binding fragment is a $(Fab')_2$ fragment. In still other embodiments, the antibody or antigen binding fragment is a diabody. In particular embodiments, the antibody or antigen binding fragment is a domain antibody. In particular embodiments, the antibody or antigen binding fragment is a single domain antibody.

In particular embodiments, a caninized murine anti-canine CTLA-4 antibody or antigen binding fragment binds to CTLA-4 in an animal subject (e.g., canine) being treated for cancer. In more particular embodiments, administration of a caninized murine anti-canine CTLA-4 antibody or antigen binding fragment of the present invention serves to ameliorate one or more symptom of cancer in the animal subject (e.g., canine) being treated.

The present invention further provides isolated nucleic acids that encode caninized murine anti-canine CTLA-4 antibodies or portions thereof. In related embodiments such antibodies or antigen binding fragments can be used for the preparation of a medicament to treat cancer in a canine subject. Alternatively, or in conjunction, the present invention provides for the use of any of the antibodies or antibody fragments of the present invention for diagnostic use. In yet additional embodiments, a kit is provided comprising any of the caninized antibodies or antigen binding fragments disclosed herein.

The present invention further provides isolated peptides that bind to a caninized antibody of the present invention, that comprise 5 to 25 amino acid residues, and are 90% identical or more to the amino acid sequence of SEQ ID NO: 132. In particular embodiments, the isolated peptides are identical to the amino acid sequence of SEQ ID NO: 132. In more particular embodiments, the isolated peptides comprise 10 to 20 amino acid residues. In related embodiments, the isolated peptides bind to a caninized antibody of the present invention, comprise 5 to 25 amino acid residues, and are 90% identical or more to the amino acid sequence of SEQ ID NO: 133. In particular embodiments, the isolated peptides are identical to the amino acid sequence of SEQ ID NO: 133. In more particular embodiments of this type, the isolated peptides comprise 10 to 20 amino acid residues.

In still other embodiments, the isolated peptides that bind to a caninized antibody of the present invention comprise amino acid sequences that are 90% identical or more to the amino acid sequence of SEQ ID NO: 134. In yet other embodiments, the isolated peptides comprise amino acid sequences that are identical to the amino acid sequence of SEQ ID NO: 134. In other embodiments, the isolated peptides that bind to a caninized antibody of the present invention comprise amino acid sequences that are 90% identical or more to the amino acid sequence of SEQ ID NO: 135. In still other embodiments, the isolated peptides comprise amino acid sequences that are identical to the amino acid sequence of SEQ ID NO: 135. In other embodiments, the isolated peptides that bind to a caninized antibody of the present invention comprise amino acid sequences that are 90% identical or more to the amino acid sequence of SEQ ID NO: 136. In yet other embodiments, the isolated peptides comprise amino acid sequences that are identical to the amino acid sequence of SEQ ID NO: 136.

The present invention further provides fusion proteins that comprise such isolated peptides that bind to a caninized antibody of the present invention. The present invention further provides fusion proteins that comprise any of the aforesaid peptides. In a particular embodiment, the fusion protein comprises such an antigenic peptide and an Fc region of a non-canine mammalian IgG antibody. In a more particular embodiment the fusion protein comprises an Fc region of a non-canine mammalian IgG antibody. In certain embodiments the non-canine mammalian IgG antibody is a murine IgG. In alternative embodiments the non-canine mammalian IgG antibody is a human IgG. In other embodiments the non-canine mammalian IgG antibody is an equine IgG. In still other embodiments the non-canine mammalian IgG antibody is a porcine IgG. In yet other embodiments the non-canine mammalian IgG antibody is a bovine IgG.

In particular embodiments the non-canine mammalian IgG antibody is an IgG1. In other embodiments the non-canine mammalian IgG antibody is an IgG2a. In still other embodiments the non-canine mammalian IgG antibody is an IgG3. In yet other embodiments the non-canine mammalian IgG antibody is an IgG4. In other embodiments the fusion protein comprises any of the aforesaid antigenic peptides and maltose-binding protein. In yet other embodiments, the fusion protein comprises any of the aforesaid antigenic peptides and beta-galactosidase. In still other embodiments the fusion protein comprises any of the aforesaid antigenic peptides and glutathione S-transferase. In yet other embodiments, the fusion protein comprises any of the aforesaid antigenic peptides and thioredoxin. In still other embodiments the fusion protein comprises any of the aforesaid antigenic peptides and Gro EL. In yet other embodiments the fusion protein comprises any of the aforesaid antigenic peptides and NusA.

The present invention also provides nucleic acids (including isolated and/or recombinant nucleic acids) that encode one or more isolated immunogenic and/or antigenic peptide and/or the fusion proteins of the present invention. The present invention further provides expression vectors comprising such isolated nucleic acids, as well as host cells that comprise one or more expression vectors of the present invention.

Pharmaceutical compositions can also comprise antigenic peptides (including isolated antigenic peptides) from canine CTLA-4, fusion proteins comprising the antigenic peptides from canine CTLA-4 of the present invention, nucleic acids (including isolated nucleic acids) encoding the antigenic fragments and/or fusion proteins of the present invention, the expression vectors comprising such nucleic acids, or any combination thereof, and a pharmaceutically acceptable carrier or diluent. In addition, the present invention includes pharmaceutical compositions comprising anti-canine CTLA-4 antibodies (including caninized murine anti-canine CTLA-4 antibodies) or antigen binding fragments thereof of the present invention. Such pharmaceutical compositions can be used to treat cancer, an infection or infective disease, be used as a vaccine adjuvant, and/or, in a method of increasing the activity of an immune cell, comprising administering to a subject in need thereof a therapeutically effective amount of the pharmaceutical composition.

In particular embodiments, such pharmaceutical compositions further comprise an anti-canine PD-1 antibody (including a caninized murine anti-canine PD-1 antibody) or antigen binding fragment thereof. In more particular embodiments, the anti-canine PD-1 antibody is a caninized murine anti-canine PD-1 antibody or a antigen binding fragment of the caninized murine anti-canine PD-1 antibody.

In related embodiments, such pharmaceutical compositions further comprise an anti-canine PD-L1 antibody (including a caninized murine anti-canine PD-L1 antibody) or an antigen binding fragment thereof. In particular embodiments the anti-canine PD-L1 antibody is a caninized murine anti-canine PD-1 antibody or an antigen binding fragment of a caninized murine anti-canine PD-1 antibody.

Accordingly, the present invention provides pharmaceutical compositions that comprise one, two, three, or more of the following: an anti-canine PD-L1 antibody, an anti-canine PD-1 antibody, an anti-canine CTLA-4 antibody, an antigen binding fragment of an anti-canine PD-L1 antibody, an antigen binding fragment of an anti-canine PD-1 antibody, or an antigen binding fragment of an anti-canine CTLA-4 antibody. In particular embodiments, such anti-canine protein (i.e., anti-canine PD-L1, PD-1, or CTLA-4) antibodies or the antigen binding fragments thereof are murine anti-canine protein antibodies. In other embodiments, such anti-canine protein antibodies or the antigen binding fragments thereof are caninized anti-canine protein antibodies. In more particular embodiments, the anti-canine protein antibodies or the antigen binding fragments thereof are caninized murine anti-canine protein antibodies.

In addition, the present invention provides methods of increasing the activity of an immune cell, comprising administering to a subject in need thereof a therapeutically effective amount of a pharmaceutical composition of the present invention. In certain embodiments the method is used in the treatment of cancer. In other embodiments, the method is used in the treatment of an infection or infectious disease. In still other embodiments, a caninized antibody of the present invention or antigen binding fragment thereof is used as a vaccine adjuvant. In particular embodiments a pharmaceutical composition comprising a caninized murine anti-canine CTLA-4 antibody or antigen binding fragment thereof can be administered before, after or concurrently with a caninized murine anti-canine PD-1 antibody or antigen binding fragment thereof and/or a caninized murine anti-canine PD-L1 antibody or antigen binding fragment thereof.

These and other aspects of the present invention will be better appreciated by reference to the following Brief Description of the Drawings and the Detailed Description.

BRIEF DESCRIPTION OF THE DRAWINGS

FIG. 1 depicts a plot of the quantity of the individual canine CTLA-4 antibodies in ng/ml (Ab Log) added to canine CTLA-4 in an ELISA demonstrating the binding activity of the antibodies to cCTLA-4. The individual antibodies to canine CTLA-4 are denoted as 27G12, 110E3,12B3,45A9,39A11, and 22A11.

FIG. 4A is the Iso-control, FIG. 4B is 39A11, FIG. 4C is 27G12, FIG. 4D is 12B3, FIG. 4E is 45A9, FIG. 4F is 110E3, and FIG. 4G is 22A11. As can be seen, the antibodies can bind to the CHO cells expressing cCTLA-4.

DETAILED DESCRIPTION OF THE INVENTION

Abbreviations

Figure 1:
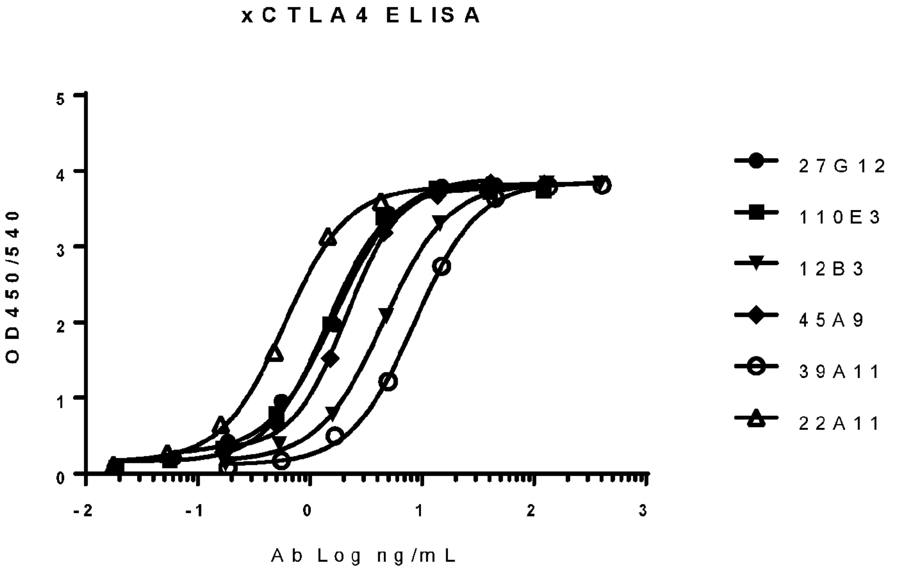
FIG. 1 displays the binding activity of six antibodies with canine CTLA-4 (cCTLA-4). Accordingly.

Throughout the detailed description and examples of the invention the following abbreviations will be used:

ADCC Antibody-dependent cellular cytotoxicity
CDC Complement-dependent cyotoxicity
CDR Complementarity determining region in the immunoglobulin variable regions, defined using the Kabat numbering system
CHO Chinese hamster ovary
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat [*Sequences of Proteins of Immunological Interest,* 5th Ed. Public Health Service, National Institutes of Health, Bethesda, Md. (1991)]
mAb Monoclonal antibody (also Mab or MAb)
MES 2-(N-morpholino)ethanesulfonic acid
MOA Mechanism of action
NHS Normal human serum
PCR Polymerase chain reaction
PK Pharmacokinetics
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VL Immunoglobulin light chain variable region
VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as “a,” “an,” and “the,” include their corresponding plural references unless the context clearly dictates otherwise.

“CTLA-4” is an abbreviation for “cytotoxic T-lymphocyte-associated protein 4”, also known as CD152 (cluster of differentiation 152), which is a protein receptor that functions as an immune checkpoint and downregulates immune responses. The amino acid sequence of canine CTLA-4 is SEQ ID NO: 126. The present invention further provides caninized murine antibodies to canine CTLA-4.

“Activation” as it applies to cells or to receptors refers to the activation or treatment of a cell or receptor with a ligand, unless indicated otherwise by the context or explicitly. Activation” can refer to cell activation as regulated by internal mechanisms as well as by external or environmental factors.

“Ligand” encompasses natural and synthetic ligands, e.g., cytokines, cytokine variants, analogues, muteins, and binding compounds derived from antibodies. “Ligand” also encompasses small molecules, e.g., peptide mimetics of cytokines and peptide mimetics of antibodies.”

“Activity” of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. “Activity” of a molecule may also refer to activity in modulating or maintaining cell-to-cell interactions, e.g., adhesion, or activity in maintaining a structure of a cell, e.g., cell membranes or cytoskeleton. “Activity” can also mean specific activity, e.g., [catalytic activity]/[mg protein], or [immunological activity]/[mg protein], concentration in a biological compartment, or the like. “Activity” may refer to modulation of components of the innate or the adaptive immune systems.

“Administration” and “treatment,” as it applies to an animal, e.g., a canine subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell.

“Administration” and “treatment” also means in vitro and ex vivo treatments, e.g., of a cell, by a reagent, diagnostic, binding compound, or by another cell.

The term “subject” includes any organism, preferably an animal, more preferably a mammal (e.g., canine, feline, or human) and most preferably a canine.

“Treat” or “treating” means to administer a therapeutic agent, such as a composition containing any of the antibodies or antigen binding fragments of the present invention, internally or externally to e.g., a canine subject or patient having one or more disease symptoms, or being suspected of having a disease, for which the agent has therapeutic activity.

Typically, the agent is administered in an amount effective to alleviate and/or ameliorate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the “therapeutically effective amount”) may vary according to factors such as the disease state, age, and weight of the patient (e.g., canine), and the ability of the pharmaceutical composition to elicit a desired response in the subject. Whether a disease symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary (e.g., canine), or research subject, refers to therapeutic treatment, as well as research and diagnostic applications. "Treatment" as it applies to a human, veterinary (e.g., canine), or research subject, or cell, tissue, or organ, encompasses contact of the antibodies or antigen binding fragments of the present invention to e.g., a canine or other animal subject, a cell, tissue, physiological compartment, or physiological fluid.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, including domestic cats, pure-bred and/or mongrel companion cats, show cats, laboratory cats, cloned cats, and wild or feral cats.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a mouse antibody) in both chains. Optionally the heavy and/or light chains of the canine antibody may contain some foreign non-CDR residues, e.g., so as to preserve the conformation of the foreign CDRs within the canine antibody, and/or to modify the Fc function, as exemplified below.

Canine CTLA-4 has been found to comprise the amino acid sequence of SEQ ID NO: 126 (including the signal sequence]. In a specific embodiment canine CTLA-4 is encoded by a nucleic acid that comprises the nucleotide sequence of SEQ ID NO: 125. Canine CTLA-4 sequences may differ by having, for example, conserved variations in non-conserved regions, but the canine CTLA-4 will have substantially the same biological function as the canine CTLA-4 comprised by the amino acid sequence of SEQ ID NO: 126.

As used herein, a "substitution of an amino acid residue" with another amino acid residue in an amino acid sequence of an antibody for example, is equivalent to "replacing an amino acid residue" with another amino acid residue and denotes that a particular amino acid residue at a specific position in the amino acid sequence has been replaced by (or substituted for) by a different amino acid residue. Such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies.

Co-stimulatory signaling pathways lead to the development of immune responses and have been shown to be mediated through the interaction of CD28 on the surface of T cells and CD80 (also known as B7.1) and CD86 (also known as B7.2). CTLA-4 binds to both CD80 and CD86 with a much higher affinity than CD28 and thereby acts as an inhibitory receptor that is vital for down-modulation of the immune response. Indeed, the mechanism by which CTLA-4 mediates its immune inhibitory functions is related to its capacity to act as a competitive inhibitor of the interaction of CD28 with CD80 and CD86. Accordingly, the present invention describes the generation and characterization of monoclonal antibodies that block the binding of canine CD80 and canine CD86 to CTLA-4 and thereby, permits the co-stimulatory signaling due to the binding of canine CD28 to canine CD80 and CD86. These antibodies therefore have utility in treatment of cancer, as well as other diseases in companion animals as disclosed herein.

A particular canine CTLA-4 amino acid sequence will generally be at least 90% identical to the canine CTLA-4 comprising the amino acid sequence of SEQ ID NO: 126, excluding the signal sequence. In certain cases, a canine CTLA-4, may be at least 95%, or even at least 96%, 97%, 98% or 99% identical to the canine CTLA-4 comprising the amino acid sequence of SEQ ID NO: 126, excluding the signal sequence. In certain embodiments, a canine CTLA-4 amino acid sequence will display no more than 10 amino acid differences from the canine CTLA-4 comprising the amino acid sequence of SEQ ID NO: 126, excluding the signal sequence. In certain embodiments, the canine CTLA-4 amino acid sequence may display no more than 5, or even no more than 4, 3, 2, or 1 amino acid difference from the canine CTLA-4 comprising the amino acid sequence of SEQ ID NO: 126, excluding the signal sequence. Percent identity can be determined as described herein below.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the mammalian body (e.g., canine body) of cancerous cells, cells or tissues infected with pathogens, or invading pathogens.

Anti-Canine CTLA-4 Antibodies

The present invention provides isolated antibodies (particularly murine anti-canine CTLA-4 antibodies and caninized antibodies thereof) or antigen binding fragments thereof that bind canine CTLA-4 and uses of such antibodies or fragments thereof. In specific embodiments murine anti-canine CTLA-4 CDRs from murine anti-canine CTLA-4 antibodies are provided that have been shown to both bind canine CTLA-4 and to block the binding of canine CTLA-4 to one or both of its ligands, canine CD86 or CD80. These CDRs can be inserted into a modified canine frame of a canine antibody to generate a caninized murine anti-canine CTLA-4 antibody.

As used herein, an "anti-canine CTLA-4 antibody" refers to an antibody that was raised against canine CTLA-4 (e.g., in a mammal such as a mouse or rabbit) and that specifically binds to canine CTLA-4. An antibody that "specifically binds to canine CTLA-4," and in particular to canine CTLA-4, or an antibody that "specifically binds to a polypeptide comprising the amino acid sequence of canine CTLA-4", is an antibody that exhibits preferential binding to canine CTLA-4 as compared to other canine antigens, but this specificity does not require absolute binding specificity. An anti-canine CTLA-4 antibody is considered "specific" for canine CTLA-4 if its binding is determinative of the presence of canine CTLA-4 in a sample that is limited to canine proteins, or if it is capable of altering the activity of canine CTLA-4 without unduly interfering with the activity of other molecules in a canine sample, e.g. without producing undesired results such as false positives in a diagnostic context or side effects in a therapeutic context. The degree of specificity necessary for an anti-canine CTLA-4 antibody may depend on the intended use of the antibody, and at any rate is defined by its suitability for use for an intended purpose. The antibody, or binding compound derived from the antigen-binding site of an antibody, of the contemplated method binds to its antigen, or a variant or mutein thereof, with an affinity that is at least two-fold greater, preferably at least ten-times greater, more preferably at least 20-times greater, and most preferably at least 100-times greater than the affinity with any other canine antigen.

As used herein, an antibody is said to bind specifically to a polypeptide comprising a given antigen sequence (in this case a portion of the amino acid sequence of canine CTLA-4) if it binds to polypeptides comprising the portion of the amino acid sequence of canine CTLA-4, but does not bind to other canine proteins lacking that portion of the sequence of canine CTLA-4. For example, an antibody that specifically binds to a polypeptide comprising canine CTLA-4, may bind to a FLAG®-tagged form of canine CTLA-4, but will not bind to other FLAG®-tagged canine proteins. An antibody, or binding compound derived from the antigen-binding site of an antibody, binds to its canine antigen, or a variant or mutein thereof, "with specificity" when it has an affinity for that canine antigen or a variant or mutein thereof which is at least ten-times greater, more preferably at least 20-times greater, and even more preferably at least 100-times greater than its affinity for any other canine antigen tested.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), canonized antibodies, fully canine antibodies, chimeric antibodies and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antigen binding fragments include, but are not limited to, Fab, Fab', $F(ab')_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

A "fragment crystallizable" ("Fc") region contains two heavy chain fragments comprising the $C_H3$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the VH domain and the $C_H1$ domain and also the region between the $C_H1$ and $C_H2$ domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_H2$ domains, such that an interchain disulfide bond is formed between the two heavy chains. A F(ab') 2 fragment thus is composed of two Fab' fragments that are held together by a disulfide bond between the two heavy chains. An "$F(ab')_2$ fragment" can be the product of pepsin cleavage of an antibody.

The "Fv region" comprises the variable regions from both the heavy and light chains, but lacks the constant regions.

The term "single-chain Fv" or "scFv" antibody refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. [See, Pluckthun, The Pharmacology of Monoclonal Antibodies, vol. 113 Rosenburg and Moore eds., Springer-Verlag, New York, pp. 269-315 (1994); WO 88/01649; and U.S. Pat. Nos. 4,946,778 and 5,260,203.]

As used herein, an anti-canine CTLA-4 antibody or antigen-binding fragment thereof that "blocks" or is "blocking" or is "blocking the binding" of canine CTLA-4 to its binding partner (ligand) e.g., canine CD80 or canine CD 86, is an anti-canine CTLA-4 antibody or antigen-binding fragment thereof that blocks (partially or fully) the binding of canine CTLA-4 to canine CD86 and/or CD80 as determined in standard binding assays (e.g., BIACore®, ELISA, or flow cytometry). Such "blocking" is exemplified in Example 4 below, using an ELISA-based blocking assay.

As used herein, the term "canonical structure" refers to the local conformation that can be adopted by each of the hypervariable regions of the heavy and light chain of an antibody within the framework that they reside. For each hypervariable region, there are a small number of canonical structures (generally denoted by simple integers such as 1 or 2 etc.), which can be predicted with great accuracy from the amino acid sequences of the corresponding hypervariable region [particularly within the context of the amino acid sequence of its framework for the corresponding anti-canine CTLA-4 variable domains]. These canonical structures can be determinative regarding whether a modification of the amino acid sequence of a given CDR will result in the retention or loss of the ability to bind to its antigen binding partner [See, Chothia and Lesk, *Canonical Structures for the hypervariable regions of immunoglobulins, J. Mol. Biol.* 196:901-917(1987); Chothia et al., *Conformation of immunoglobulin hypervaribale regions, Nature,* 34:877-883 (1989); and Al-Lazikani et al., *Standard Conformations for the canonical structures of immunoglobulins, J. Mol. Biol.* 273:927-948 (1997)].

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. [See, e.g., Muyldermans et al., *Trends Biochem. Sci.* 26:230 (2001); Reichmann et al., *J. Immunol. Methods* 231:25 (1999); WO 94/04678; WO 94/25591; U.S. Pat. No. 6,005,079]. In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. [See, EP 0 404 097 B1; WO 93/11161; and Holliger et al., *Proc. Natl. Acad. Sci. USA* 90: 6444-6448 (1993)]. For a review of engineered antibody variants [generally see Holliger and Hudson *Nat. Biotechnol.* 23:1126-1136 (2005)].

Typically, an antibody or antigen binding fragment of the invention retains at least 10% of its canine CTLA-4 binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine CTLA-4 binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, a "chimeric antibody" is an antibody having the variable domain from a first antibody and the constant domain from a second antibody, where the first and second antibodies are from different species. [U.S. Pat. No. 4,816,567; and Morrison et al., *Proc. Natl. Acad. Sci. USA* 81: 6851-6855 (1984)]. Typically the variable domains are obtained from an antibody from an experimental animal (the "parental antibody"), such as a rodent, and the constant domain sequences are obtained from the animal subject antibodies, e.g., human or canine so that the resulting chimeric antibody will be less likely to elicit an adverse immune response in a human or canine subject respectively, than the parental (e.g., rodent) antibody.

As used herein, the term "caninized antibody" refers to forms of antibodies that contain sequences from both canine and non-canine (e.g., murine) antibodies. In general, the caninized antibody will comprise substantially all of at least one or more typically, two variable domains in which all or substantially all of the hypervariable loops correspond to those of a non-canine immunoglobulin (e.g., comprising 6 murine anti-canine CTLA-4 CDRs as exemplified below), and all or substantially all of the framework (FR) regions (and typically all or substantially all of the remaining frame) are those of a canine immunoglobulin sequence. As exemplified herein, a caninized antibody comprises both the three heavy chain CDRs and the three light chain CDRS from a murine anti-canine CTLA-4 antibody together with a canine frame or a modified canine frame. A modified canine frame comprises one or more amino acids changes as exemplified herein that further optimize the effectiveness of the caninized antibody, e.g., to increase its binding to canine CTLA-4 and/or its ability to block the binding of canine CTLA-4 to canine CD86 and/or CD80.

The term "fully canine antibody" refers to an antibody that comprises canine immunoglobulin protein sequences only. A fully canine antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully canine antibody may contain rat carbohydrate chains if produced in a rat, in a rat cell, or in a hybridoma derived from a rat cell. Similarly, "rat antibody" refers to an antibody that comprises rat immunoglobulin sequences only.

There are four known IgG heavy chain subtypes of dog IgG and they are referred to as IgG-A, IgG-B, IgG-C, and IgG-D. The two known light chain subtypes are referred to as lambda and kappa.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). [See Kabat et al. *Sequences of Proteins of Immunological Interest,* 5th Ed. Public Health Service, National Institutes of Health, Bethesda, Md. (1991), defining the CDR regions of an antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

In specific embodiments of the invention, besides binding and activating of canine immune cells, a canine or caninized antibody against CTLA-4 optimally has two attributes:

1. Lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has high level of ADCC activity. On the other hand, IgG-A binds weakly to protein A, but also displays ADCC activity. Moreover, neither IgG-C nor IgG-D can be purified on protein A columns, although IgG-D displays no ADCC activity. (IgG-C has considerable ADCC activity). One way the present invention addresses these issues is by providing modified canine IgG-B antibodies specific to CTLA-4 that lack the effector functions such as ADCC and can be easily of purified using industry standard protein A chromatography.

In alternative embodiments of the present invention, the canine IgG-B or IgG-C antibodies specific to CTLA-4 are purposely not modified to remove/substantially diminish the effector functions such as ADCC, and therefore retain the effector functions such as ADCC.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology. "Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. [*Nucleic Acids Res.* 33:D256-D261 (2005)].

Properties of Murine Anti-Canine CTLA-4 and Caninized Murine Anti-Canine CTLA-4 Antibodies The present invention provides isolated murine anti-canine CTLA-4 antibodies and caninized antibodies thereof, methods of use of the antibodies or antigen binding fragments thereof in the treatment of disease e.g., the treatment of cancer in canines. In canine, there are four IgG heavy chains referred to as A, B, C, and D. These heavy chains represent four different subclasses of dog IgG, which are referred to as IgGA, IgGB, IgGC and IgGD. Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region".

The DNA and amino acid sequences of these four heavy chains were first identified by Tang et al. [*Vet. Immunol. Immunopathol.* 80: 259-270 (2001)]. The amino acid and DNA sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example the kappa light chain amino acid sequence has accession number ABY 57289.1 and the lambda light chain has accession number ABY 55569.1.

In the present invention, the amino acid sequence for each of the four canine IgG Fc fragments is based on the identified boundary of $C_H1$ and $C_H2$ domains as determined by Tang et al, supra. Caninized murine anti-canine CTLA-4 antibodies that bind canine CTLA-4 include, but are not limited to: antibodies that comprise canine IgG-A, IgG-B, IgG-C, and IgG-D heavy chains and/or canine kappa light chains together with murine anti-canine CTLA-4 CDRs. Accordingly, the present invention provides isolated murine anti-canine CTLA-4 and/or caninized murine anti-canine CTLA-4 antibodies or antigen binding fragments thereof that bind to canine CTLA-4 and block the binding of canine CTLA-4 to canine CD86 and/or canine CD80.

The present invention further provides full length canine heavy chains that can be matched with corresponding light chains to make a caninized antibody. Accordingly, the present invention further provides caninized murine anti-canine antigen antibodies (including isolated caninized murine anti-canine CTLA-4 antibodies) and methods of use of the antibodies or antigen binding fragments thereof in the treatment of disease e.g., the treatment of cancer in canines.

The present invention also provides caninized murine anti-canine-CTLA-4 antibodies that comprise a canine fragment crystallizable region (cFc region) in which the cFc has been genetically modified to augment, decrease, or eliminate one or more effector functions. In one aspect of the present invention, the genetically modified cFc decreases or eliminates one or more effector functions. In another aspect of the invention the genetically modified cFc augments one or more effector function. In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

In order to generate variants of canine IgG that lack effector functions, a number of mutant canine IgGB heavy chains were generated. These variants may include one or more of the following single or combined substitutions in the Fc portion of the heavy chain amino acid sequence: P4A, D31A, N63A, G64P, T65A, A93G, and P95A. Variant heavy chains (i.e., containing such amino acid substitutions) were cloned into expression plasmids and transfected into HEK 293 cells along with a plasmid containing the gene encoding a light chain. Intact antibodies expressed and purified from HEK 293 cells were evaluated for binding to $Fc_{\gamma}RI$ and C1q to assess their potential for mediation of immune effector functions. [See, U.S. Pat. No. 10,106,607 B2, the contents of which are hereby incorporated by reference in its entirety.]

The present invention also provides modified canine IgGDs which in place of its natural IgGD hinge region they comprise a hinge region from:

```
                                SEQ ID NO: 128
IgGA: FNECRCTDTPPCPVPEP;

                                SEQ ID NO: 129
IgGB: PKRENGRVPRPPDCPKCPAPEM;
or

                                SEQ ID NO: 130
IgGC: AKECECKCNCNNCPCPGCGL.
```

Alternatively, the IgGD hinge region can be genetically modified by replacing a serine residue with a proline residue, i.e., PKESTCKCIPPCPVPES, SEQ ID NO: 131 (with the proline residue (P) underlined and in bold substituting for the naturally occurring serine residue). Such modifications can lead to a canine IgGD lacking fab arm exchange. The modified canine IgGDs can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgGD can be modified so that it encodes the modified IgGDs. The modified nucleic acid sequences are then cloned into expression plasmids for protein expression.

The antibody or antigen binding fragment thereof that binds canine CTLA-4 can comprise three, four, five, or six of the complementarity determining regions (CDRs) of a murine anti-canine antibody, as described herein. The three, four, five, or six CDRs may be independently selected from the CDR sequences of those provided below. In a further embodiment, the isolated antibody or antigen-binding fragment thereof that binds canine CTLA-4 comprises a canine antibody kappa or lambda light chain comprising a murine light chain CDR-1, CDR-2 and/or CDR-3 and a canine antibody heavy chain IgG comprising a murine heavy chain CDR-1, CDR-2 and/or CDR-3.

In other embodiments, the invention provides antibodies or antigen binding fragments thereof that specifically bind canine CTLA-4 and have canine antibody kappa or lambda light chains comprising a given set of three CDRs comprising at least 80%, 85%, 90%, 95%, 98% or 99% sequence identity with the amino acid sequences of SEQ ID NOs: 92, 94, and 96 for the VLCDR-1, VLCDR-2 and VLCDR-3, respectively, and canine antibody heavy chain IgG comprising given set of three CDRs comprising at least 80%, 85%, 90%, 95%, 98% or 99% sequence identity with the amino acid sequences of SEQ ID NOs: 86, 88, and 90 for the VHCDR-1, VHCDR-2 and VHCDR-3, respectively; or canine antibody kappa or lambda light chains comprising a given set of three CDRs comprising at least 80%, 85%, 90%, 95%, 98% or 99% sequence identity with the amino acid sequences of SEQ ID NOs: 104, 106, and 108, for the VLCDR-1, VLCDR-2 and VLCDR-3, respectively, and canine antibody heavy chain IgG comprising a set of different CDRs comprising at least 80%, 85%, 90%, 95%, 98% or 99% sequence identity with the amino acid sequences of SEQ ID NOs: 98, 100, and 102 for the VHCDR-1, VHCDR-2 and VHCDR-3, respectively; or canine antibody kappa or lambda light chains comprising a given set of three CDRs comprising at least 80%, 85%, 90%, 95%, 98% or 99% sequence identity with the amino acid sequences of SEQ ID NOs: 117, 94, and 96, for the VLCDR-1, VLCDR-2 and VLCDR-3, respectively, and canine antibody heavy chain IgG comprising a set of different CDRs comprising at least 80%, 85%, 90%, 95%, 98% or 99% sequence identity with the amino acid sequences of SEQ ID NOs: 86, 88, and 113 for the VHCDR-1, VHCDR-2 and VHCDR-3, respectively; or canine antibody kappa or lambda light chains comprising a given set of three CDRs comprising at least 80%, 85%, 90%, 95%, 98% or 99% sequence identity with the amino acid sequences of SEQ ID NOs: 119, 122, and 96 for the VLCDR-1, VLCDR-2 and VLCDR-3, respectively, and canine antibody heavy chain IgG comprising a set of different CDRs comprising at least 80%, 85%, 90%, 95%, 98% or 99% sequence identity with the amino acid sequences of SEQ ID NOs: 86, 88, and 115 for the VHCDR-1, VHCDR-2 and VHCDR-3, respectively; while still exhibiting the desired binding and functional properties. In another embodiment the antibody or antigen binding fragment of the present invention comprises a canine frame comprising a combination of IgG heavy chain sequence with a kappa or lambda light chain having one or more of the above-mentioned set of three light chain CDRs and three heavy chain CDRs with 0, 1, 2, 3, 4, or 5 conservative or non-conservative amino acid substitutions, while still exhibiting the desired binding and functional properties.

Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In particular embodiments selected deletions or insertions that could otherwise alter the correspondence between the two amino acid sequences are taken into account.

Sequence similarity includes identical residues and non-identical, biochemically related amino acids. Biochemically related amino acids that share similar properties and may be interchangeable are discussed "Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Exemplary conservative substitutions are set forth in Table A directly below.

TABLE A

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table A above.

Nucleic Acids

The present invention further comprises the nucleic acids encoding the immunoglobulin chains of murine anti-canine CTLA-4 and/or caninized murine anti-canine CTLA-4 antibodies and antigen binding fragments thereof disclosed herein (see e.g., Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the caninized antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput.* Appl. Biosci. 10:67-70 (1994); ALIGNMENT SCORING SYSTEMS: Dayhoff, M O., et al., "A model of evolutionary change in proteins." in *Atlas of Protein Sequence and Structure*, vol. 5, suppl. 3. M. O. Dayhoff (ed.), pp. 345-352, (1978); *Natl. Biomed. Res. Found*, Washington, D.C.; Schwartz, R. M., et al., "Matrices for detecting distant relationships." in Atlas of Protein Sequence and Structure, vol. 5, suppl. 3." (1978), M. O. Dayhoff (ed.), pp. 353-358 (1978), *Natl. Biomed. Res. Found.*, Washington, D.C.; Altschul, S. F., *J. Mol. Biol.* 219:555-565 (1991); States, D. J., et al., *Methods* 3:66-70(1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, New York (1997).

This present invention also provides expression vectors comprising the nucleic acids of the invention, in which the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium and isolating the antigen or antigen binding fragment thereof from the host cell or culture medium.

A caninized murine anti-canine CTLA-4 antibody can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

The present invention further includes antibody fragments of the murine anti-canine CTLA-4 antibodies disclosed herein. The antibody fragments include $F(ab)_2$ fragments, which may be produced by enzymatic cleavage of an IgG by, for example, pepsin. Fab fragments may be produced by, for example, reduction of $F(ab)_2$ with dithiothreitol or mercaptoethylamine. A Fab fragment is a $V_L$-$C_L$ chain appended to a $V_H$-$C_{H1}$ chain by a disulfide bridge. A $F(ab)_2$ fragment is two Fab fragments which, in turn, are appended by two disulfide bridges. The Fab portion of an $F(ab)_2$ molecule includes a portion of the $F_c$ region between which disulfide bridges are located. An Fv fragment is a $V_L$ or $V_H$ region.

In one embodiment, the antibody or antigen binding fragment comprises a heavy chain constant region, e.g., a canine constant region, such as IgGA, IgGB, IgGC and IgGD canine heavy chain constant region or a variant thereof. In another embodiment, the antibody or antigen binding fragment comprises a light chain constant region, e.g., a canine light chain constant region, such as lambda or kappa canine light chain region or variant thereof. By way of example, and not limitation, the canine heavy chain constant region can be from IgG-B and the canine light chain constant region can be from kappa.

Antibody Engineering

Caninized murine anti-canine CTLA-4 antibodies of the present invention can be engineered to include modifications to canine framework and/or canine frame residues within the variable domains of a parental (i.e., canine) monoclonal antibody, e.g. to improve the properties of the antibody.

Epitope Binding and Binding Affinity

The present invention further provides antibodies or antigen binding fragments thereof that bind to amino acid residues of the same epitope of canine CTLA-4 as the murine anti-canine CTLA-4 antibodies disclosed herein. In particular embodiments the murine anti-canine CTLA-4 antibodies or antigen binding fragments thereof also are capable of inhibiting/blocking the binding of canine CTLA-4 to canine CD86 and/or CD80. In related embodiments the caninized murine anti-canine CTLA-4 antibodies or antigen binding fragments thereof also are capable of inhibiting/blocking the binding of canine CTLA-4 to canine CD86 and/or CD80.

Experimental and Diagnostic Uses

Murine anti-canine CTLA-4 and/or caninized murine anti-canine CTLA-4 antibodies or antigen-binding fragments thereof of the present invention may also be useful in diagnostic assays for canine CTLA-4 protein, e.g., detecting its expression in conjunction with and/or relation to cancer for example.

For example, such a method comprises the following steps:

(a) coat a substrate (e.g., surface of a microtiter plate well, e.g., a plastic plate) with a murine anti-canine CTLA-4 antibody or an antigen-binding fragment thereof;
(b) apply a sample to be tested for the presence of canine CTLA-4 to the substrate;
(c) wash the plate, so that unbound material in the sample is removed;
(d) apply detectably labeled antibodies (e.g., enzyme-linked antibodies) which are also specific to the CTLA-4 antigen;
(e) wash the substrate, so that the unbound, labeled antibodies are removed;

(f) if the labeled antibodies are enzyme linked, apply a chemical which is converted by the enzyme into a fluorescent signal; and (g) detect the presence of the labeled antibody.

In a further embodiment, the labeled antibody is labeled with peroxidase which react with ABTS [e.g., 2,2'-azino-bis (3-ethylbenzthiazoline-6-sulphonic acid)] or 3,3',5,5'-Tetramethylbenzidine (TMB) to produce a color change which is detectable. Alternatively, the labeled antibody is labeled with a detectable radioisotope (e.g., 41) which can be detected by scintillation counter in the presence of a scintillant. Murine anti-canine CTLA-4 antibodies of the invention may be used in a Western blot or immuno protein blot procedure.

Such a procedure forms part of the present invention and includes for example:

(i) contacting a membrane or other solid substrate to be tested for the presence of bound canine CTLA-4 or a fragment thereof with a caninized murine anti-canine CTLA-4 antibody or antigen-binding fragment thereof of the present invention. Such a membrane may take the form of a nitrocellulose or vinyl-based [e.g., polyvinylidene fluoride (PVDF)] membrane to which the proteins to be tested for the presence of canine CTLA-4 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the caninized murine anti-canine CTLA-4 antibody or antigen-binding fragment thereof, the membrane is optionally blocked, e.g., with non-fat dry milk or the like so as to bind non-specific protein binding sites on the membrane.

(ii) washing the membrane one or more times to remove unbound caninized murine anti-canine CTLA-4 antibody or an antigen-binding fragment thereof and other unbound substances; and (iii) detecting the bound caninized murine anti-canine CTLA-4 antibody or antigen-binding fragment thereof.

Detection of the bound antibody or antigen-binding fragment may be by binding the antibody or antigen-binding fragment with a secondary antibody (an anti-immunoglobulin antibody) which is detectably labeled and, then, detecting the presence of the secondary antibody.

The murine anti-canine CTLA-4 antibodies, the caninized murine anti-canine CTLA-4 antibodies, and/or the antigen-binding fragments thereof disclosed herein may also be used for immunohistochemistry. Such a method forms part of the present invention and comprises, e.g., (1) contacting a cell to be tested for the presence of canine CTLA-4 with e.g., a murine anti-canine CTLA-4 antibody or antigen-binding fragment thereof of the present invention; and (2) detecting the antibody or fragment on or in the cell. If the antibody or antigen-binding fragment itself is detectably labeled, it can be directly detected. Alternatively, the antibody or antigen-binding fragment may be bound by a detectably labeled secondary antibody which is detected.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 [See e.g., Gordon et al., *International Rev. Neurobiol.* 67:385-440 (2005)].

Cross-Blocking Antibodies

Furthermore, an anti-canine CTLA-4 antibody or antigen-binding fragment thereof of the present invention includes any antibody or antigen-binding fragment thereof that binds to the same epitope in canine CTLA-4 to which the antibodies and fragments discussed herein bind and any antibody or antigen-binding fragment that cross-blocks (partially or fully) or is cross-blocked (partially or fully) by an antibody or fragment discussed herein for canine CTLA-4 binding; as well as any variant thereof.

The cross-blocking antibodies and antigen-binding fragments thereof discussed herein can be identified based on their ability to cross-compete with the antibodies disclosed herein (on the basis of the CDRs as provided below in Example 5), i.e., 45A9, 27G12, 22A11, 110E3; and more particularly, 12B3 and/or 39A11 in standard binding assays (e.g., BIACore®, ELISA, as exemplified below, or flow cytometry). For example, standard ELISA assays can be used in which a recombinant canine CTLA-4 protein is immobilized on the plate, one of the antibodies is fluorescently labeled and the ability of non-labeled antibodies to compete off the binding of the labeled antibody is evaluated. Additionally or alternatively, BIAcore® analysis can be used to assess the ability of the antibodies to cross-compete. The ability of a test antibody to inhibit the binding of, for example, 27G12, 45A9, 110E3 and/or 22A11; and even more particularly 12B3 and/or 39A11, to canine CTLA-4 demonstrates that the test antibody can compete with 27G12, 45A9, 110E3 and/or 22A11, and/or 12B3 and/or 39A11 for binding to canine CTLA-4 and thus, may, in some cases, bind to the same epitope on canine CTLA-4 as 27G12, 45A9, 110E3 and/or 22A11, and/or 12B3 and/or 39A11. As stated above, antibodies and fragments that bind to the same epitope as any of the anti-canine CTLA-4 antibodies or fragments of the present invention also form part of the present invention.

Pharmaceutical Compositions and Administration

To prepare pharmaceutical or sterile compositions of a caninized murine anti-canine CTLA-4 antibody or antigen binding fragment thereof it can be admixed with a pharmaceutically acceptable carrier or excipient. [See, e.g., *Remington's Pharmaceutical Sciences* and *U.S. Pharmacopeia: National Formulary*, Mack Publishing Company, Easton, Pa. (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.]. In one embodiment, anti-CTLA-4 antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the caninized murine anti-canine CTLA-4 antibody or antigen binding fragment thereof can be administered by an invasive route such as by injection. In further embodiments of the invention, a caninized murine anti-canine CTLA-4 antibody or antigen binding fragment thereof, or pharmaceutical composition thereof, is administered intravenously, subcutaneously, intramuscularly, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer a murine anti-canine or a caninized murine anti-canine CTLA-4 antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis*, Marcel Dekker, New York, N.Y. (1991); Bach (ed.) *Monoclonal Antibodies and Peptide Therapy in Autoimmune Diseases*, Marcel Dekker, New York, N.Y. (1993); Baert, et al. *New Engl. J. Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., tumor size.

Antibodies or antigen binding fragments thereof disclosed herein may be provided by continuous infusion, or by doses administered, e.g., daily, 1-7 times per week, weekly, biweekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 μg/kg body weight, more generally at least 0.2 μg/kg, 0.5 μg/kg, 1 μg/kg, 10 μg/kg, 100 μg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of a caninized murine anti-canine CTLA-4 antibody in the subject's serum, such as 0.1, 0.3, 1, 3, 10, 30, 100, 300 μg/ml or more. In other embodiments, a caninized murine anti-canine CTLA-4 antibody of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

Antigenic peptides (e.g., peptides comprising epitopes or portions thereof from CTLA-4) that are recognized by anti-canine CTLA-4 mAbs also may be used as vaccines to elicit antibodies that block the binding of canine CTLA-4 to canine CD80 and/or CD86. Such vaccines may be useful as therapeutic vaccines for diseases such as cancer. In order to use these antigenic peptides as vaccines, one or more of these peptides may be coupled chemically or through the techniques of recombinant DNA technology to another carrier protein in order to enhance the immunogenicity of these peptides and elicit peptide-specific antibodies. Techniques for coupling peptides to carrier proteins are known to those skilled in the art. Peptide vaccines may be used to vaccinate animals by IM, S/C, oral, spray or in ovo routes. Peptide vaccines may be used as subunit proteins expressed from bacterial, viral, yeast or baculovirus virus systems. Alternatively such peptide vaccines may be delivered following administration of a variety of viral or bacterial vectors that express such peptide vaccines as can be practiced by methods known to those skilled in the art. The peptide vaccines may be administered in doses from 1-1000 μg and may optionally contain an adjuvant and an acceptable pharmaceutical carrier.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject (e.g., a canine) with a disorder, disease or symptom, or with the potential to develop such a disorder, disease or symptom.

As used herein, the terms "therapeutically effective amount", "therapeutically effective dose" and "effective amount" refer to an amount of a caninized murine anti-canine CTLA-4 antibody or antigen binding fragment thereof of the present invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially, or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Other Combination Therapies

As previously described, a caninized murine anti-canine CTLA-4 antibody or antigen binding fragment thereof and/or an antigenic peptide of the present invention may be coadministered with one or other more therapeutic agents (such as an inhibitor as discussed in the next paragraph) and/or a caninized murine anti-canine PD-1 antibody [see e.g., U.S. Pat. No. 9,944,704 B2 and U.S. Pat. No. 10,106,107 B2, the contents of both of which are hereby incorporated by reference in their entireties] and/or a caninized murine anti-canine PD-L1 antibody [see e.g., U.S. 20180237535 A1, the contents of which are hereby incorporated by reference in their entireties]. The antibod(ies) may be linked to the agent (as an immunocomplex) and/or can be administered separately from the agent or other antibody. In the latter case (separate administration), the antibodies can be administered before, after or concurrently with the agent or can be coadministered with other known therapies.

Kits

Further provided are kits comprising one or more components that include, but are not limited to, an antibody or antigen binding fragment, as discussed herein, which specifically binds CTLA-4 (e.g., a caninized murine anti-canine CTLA-4 antibody or antigen binding fragment thereof) in association with one or more additional components including, a caninized murine anti-canine PD-1 antibody and/or a caninized murine anti-canine PD-L1 antibody. The binding compositions as described directly above, can be formulated as a pure composition or in combination with a pharmaceutically acceptable carrier, in a pharmaceutical composition.

In one embodiment, the kit includes a binding composition of the present invention (e.g., a caninized murine anti-canine CTLA-4 or a pharmaceutical composition thereof in one container (e.g., in a sterile glass or plastic vial), a caninized murine anti-canine PD-1 antibody, and/or a caninized murine anti-canine PD-L1 antibody or pharmaceutical composition(s) thereof in another container (e.g., in a sterile glass or plastic vial).

If the kit includes a pharmaceutical composition for parenteral administration to a subject, the kit can also include a device for performing such administration. For example, the kit can include one or more hypodermic needles or other injection devices as discussed above. The kit can also include a package insert including information concerning the pharmaceutical compositions and dosage forms in the kit. Generally, such information aids pet owners and veterinarians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an antibody or specific binding agent disclosed herein can be provided in a kit, i.e., a packaged combination of reagents in predetermined amounts with instructions for performing the diagnostic or detection assay. Where the antibody or antibodies is/are labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

Example 1

Generation of Mouse Monoclonal Antibodies to Canine CTLA-4 and Corresponding Mouse-Canine Chimeric Antibodies Mouse monoclonal antibodies were generated using mouse hybridoma technology with the canine CTLA-4 (cCTLA-4) recombinant protein as the immunogen. Positive hybridoma clones were selected based on the antibody reactivity with cCTLA-4 and the blocking of the interaction of canine CD86 or CD80 with cCTLA-4 (blocking activity) by ELISA and FACS assays. Selected hybridoma clones were sequenced by rapid amplification of cDNA ends (RACE) for antibody fragments of $V_H$ and $V_L$ sequence. The six monoclonal antibodies selected are denoted as: 12B3, 27G12, 39A11, 45A9, 110E3 and 22A11, respectively. The amino acid sequences of the six antibodies are SEQ ID NOs: 2, 4, 6, 8, 10, and 12 for the heavy chain variable region respectively, and SEQ ID NOs: 14, 16, 18, 20, 22, and 24 for light chain variable region, respectively. The CDRs are underlined in the sequences provided below [see also, Table 1 below]. The corresponding nucleotide sequences that encode the above-identified amino acid sequences are listed as SEQ ID NOs: 1, 3, 5, 7, 9, and 11 for heavy chain variable region, respectively and SEQ ID NOs: 13, 15, 17, 19, 21, and 23 for light chain variable region, respectively. The nucleotide sequences of the heavy chain variable regions were fused to the nucleotide sequence of a modified canine constant heavy chain ($C_H$1-Hinge-$C_H$2-$C_H$3), respectively, to produce a chimeric mouse-canine heavy chain nucleotide sequence designated as SEQ ID NOs: 25, 27, 29, 31, 33, and 35. The variable regions are in bold. The nucleotide sequences of the light chain variable region were fused to the nucleotide sequence of the canine constant kappa light chain domain, respectively to produce a chimeric mouse-canine light chain nucleotide sequence designated as SEQ ID NOs: 37, 39, 41, 43, 45, and 47. The variable regions are in bold. The amino acid sequences encoded by the chimeric mouse-canine heavy chain nucleotide sequences were designated as SEQ ID NOs: 26, 28, 30, 32, 34, and 36. The amino acid sequences encoded by the chimeric mouse-canine light chain nucleotide sequences were designated as SEQ ID NOs: 38, 40, 42, 44, 46, and 48. The variable regions are in bold and the CDRs are underlined. The chimeric human-canine heavy and light chains were cloned into separate expression plasmids using standard molecular biology techniques. Plasmids containing heavy and light chain genes were transfected into HEK 293 cells and the expressed antibody was purified from HEK 293 cell supernatant using protein A.

Example 2

Amino Acid Sequences of the Mouse CDRS

The CDRs from mouse anti-canine CTLA-4 monoclonal antibodies are listed in Table 1 below.

TABLE 1

AMINO ACID SEQUENCES OF THE MOUSE CDRs

| | Amino Acid Sequence | SEQ ID NO: |
|---|---|---|
| VH CDR-1 | | |
| 12B3 | AsnTyrGlyMetAsn | 86 |
| 45A9 | AsnTyrGlyMetAsn | 86 |
| 27G12 | ThrTyrGlyValSer | 109 |
| 39A11 | AspTyrTyrMetSer | 98 |
| 110E3 | AsnTyrGlyMetAsn | 86 |
| 22A11 | SerTyrTrpMetHis | 110 |
| VH CDR-2 | | |
| 12B3 | TrpIleAsnThrTyrThrGly GluProThrTyrAlaAspAsp PheLysGly | 88 |
| 45A9 | TrpIleAsnThrTyrThrGly GluProThrTyrAlaAspAsp PheLysGly | 88 |
| 27G12 | TrpIleAsnThrTyrSerGly MetProThrTyrValAspAsp PheLysGly | 111 |
| 39A11 | PheIleArgAsnLysAlaAsn GlyTyrThrThrGluTyrSer AlaSerLeuLysGly | 100 |
| 110E3 | TrpIleAsnThrTyrThrGly GluProThrTyrAlaAspAsp PheLysGly | 88 |
| 22A11 | AsnIleAsnProSerAsnGly GlyThrArgPheAsnGluLys PheLysAsn | 112 |
| VH CDR-3 | | |
| 12B3 | ArgSerIleTyrTyrProTyr | 90 |
| 45A9 | ArgGlyThrTyrTyrArgPro | 113 |
| 27G12 | ArgGlyIleSerPheAspTyr | 114 |
| 39A11 | PheGlyLeuMetTyrTyrPhe AspTyr | 102 |
| 110E3 | ArgGlyValArgLeuAspTyr | 115 |
| 22A11 | SerAsnTyrGlySerGlyTrp AlaTrpPheAlaTyr | 116 |
| VL CDR-1 | | |
| 12B3 | ArgSerSerGlnSerIleVal TyrSerAsnGlyAsnThrTyr LeuGlu | 92 |
| 45A9 | ArgSerSerGlnSerIleVal TyrSerHisGlyAsnThrTyr LeuGlu | 117 |
| 27G12 | LysSerSerGlnSerIleVal TyrIleAsnGlyAsnThrTyr LeuGlu | 118 |
| 39A11 | ArgAlaSerSerSerValSer SerSerTyrLeuHis | 104 |
| 110E3 | ArgSerSerGlnSerIleVal TyrIleSerGlySerThrTyr LeuGlu | 119 |
| 22A11 | HisAlaSerGlnAsnIleAsn ValTrpLeuSer | 120 |
| VL CDR-2 | | |
| 12B3 | LysValSerAsnArgPheSer | 94 |
| 45A9 | LysValSerAsnArgPheSer | 94 |
| 27G12 | LysValSerLysArgPheSer | 121 |

TABLE 1-continued

| AMINO ACID SEQUENCES OF THE MOUSE CDRs | | |
|---|---|---|
| | Amino Acid Sequence | SEQ ID NO: |
| 39A11 | SerThrSerAsnLeuAlaSer | 106 |
| 110E3 | LysValSerSerArgPheSer | 122 |
| 22A11 | LysSerSerAsnLeuHisThr | 123 |
| VL CDR-3 | | |
| 12B3 | PheGlnGlySerHisValPro TrpThr | 96 |
| 45A9 | PheGlnGlySerHisValPro TrpThr | 96 |
| 27G12 | PheGlnGlySerHisValPro TrpThr | 96 |
| 39A11 | GlnGlnTyrSerGlyLeuPro LeuThr | 108 |
| 110E3 | PheGlnGlySerHisValPro TrpThr | 96 |
| 22A11 | GlnGlnGlyGlnSerTyrPro TrpThr | 124 |

The individual canonical structure assignments for the six CDRs of each of the six antibodies are provided in Table 2 below.

TABLE 2

| CANONICAL STRUCTURES OF THE MOUSE CDRs | | | | | | |
|---|---|---|---|---|---|---|
| Antibody | L1 | L2 | L3 | H1 | H2 | H3 |
| 12B3 | 4 | 1 | 1 | 1 | 2A | 7 |
| 27G12 | 4 | 1 | 1 | 1 | 2A | 7 |
| 39A11 | 1 | 1 | 1 | 1 | 4 | 9 |
| 45A9 | 4 | 1 | 1 | 1 | 2A | 7 |
| 22A11 | 2 | 1 | 1 | 1 | 2A | 12 |
| 110E3 | 4 | 1 | 1 | 1 | 2A | 7 |

Example 3

Reactivity of the Chimeric Antibodies with Canine CTLA-4

A chimeric antibody usually possesses the same reactivity as its parental mouse antibody. To confirm the reactivity of the six antibodies with cCTLA-4, the mouse-canine chimeric antibodies were produced and tested for their reactivities with cCTLA-4 by ELISA as follows:

1. Coated 200 ng/well cCTLA-4 in an immunoplate and incubated the plate at 4° C. overnight.
2. Washed the plate 3 times by PBS with 0.05% Tween 20 (PBST).
3. Blocked the plate with 0.5% BSA in PBS for 45-60 min at room temperature.
4. Washed the plate 3 times with PBST.
5. Three-fold diluted the antibodies in each column or row of dilution plate.
6. Transferred the diluted antibodies into each column or row of the plate, and incubated the plate for 45-60 min at room temperature.
7. Washed the plate 3 times with PBST.
8. Added 1:2000 diluted horseradish peroxidase labeled anti-canine IgG Fc into each well of the plate, and incubated the plate for 45-60 min at room temperature.
9. Washed the plate 3 times with PBST.
10. Added TMB Substrate into each well of the plate, and incubated the plate for 10 to 15 minutes at room temperature to allow for color development.
11. Added 100 μL of 1.5 M phosphoric acid into each well to stop the reaction.
12. Read the plate at 450 nm with 540 nm reference wavelength.

The ELISA results indicate that the chimeric antibodies can bind to cCTLA-4 [see, FIG. 1].

Example 4

Blocking Activity of the Chimeric Antibodies on the Interaction of Canine CD86 or CD80 with Canine CTLA-4

To investigate the blocking activity of the chimeric antibodies, an ELISA-based blocking assay was conducted as follows:

1. Coat 200 ng/well cCTLA-4 in an immunoplate and incubate the plate at 4° C. overnight.
2. Wash the plate 3 times by PBS with 0.05% Tween 20 (PBST).
3. Block the plate with 0.5% BSA in PBS for 45-60 min at room temperature.
4. Wash the plate 3 times by PBST.
5. Three-fold diluted the antibodies in each column or row of dilution plate, and then added 100 ng/well biotinylated CD86 or CD80. Next mixed with the antibodies.
6. Transferred the mixture into each column or row of the immunoplate, and incubated the plate for 45-60 min at room temperature.
7. Washed the plate 3 times with PBST.
8. Added 1:2000 diluted horseradish peroxidase conjugated streptavidin into each well of the plate, and incubated the plate for 45-60 min at room temperature.
9. Washed the plate 3 times with PBST.
10. Added the TMB Substrate into each well of the plate, and incubated the plate for 10 to 15 minutes at room temperature to allow for color development.
11. Added 100 μL of 1.5 M phosphoric acid into each well to stop the reaction.
12. Read the plate at 450 nm with 540 nm reference wavelength.

Figure 2:
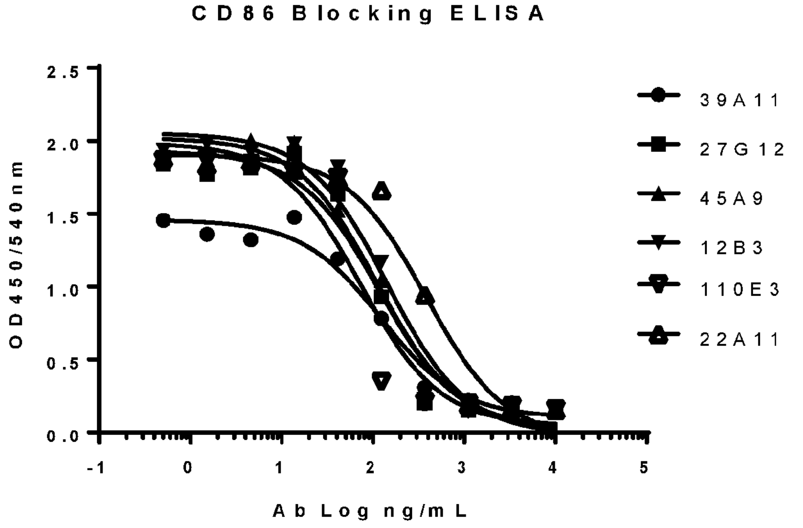
FIG. 2 depicts the antibodies blocking the interaction of canine CD86 with CTLA-4. The figure depicts a plot of the quantity of the individual canine CTLA-4 antibodies in ng/ml (Ab Log) added to cCTLA-4 to interfere with the binding of canine CTLA-4 to CD86. The individual antibodies to canine CTLA-4 are denoted as 39A11, 27G12, 45A9, 12B3, 110E3, and 22A11. As can be seen, the antibodies can block the interaction of canine CD86 with CTLA-4.
Figure 3:
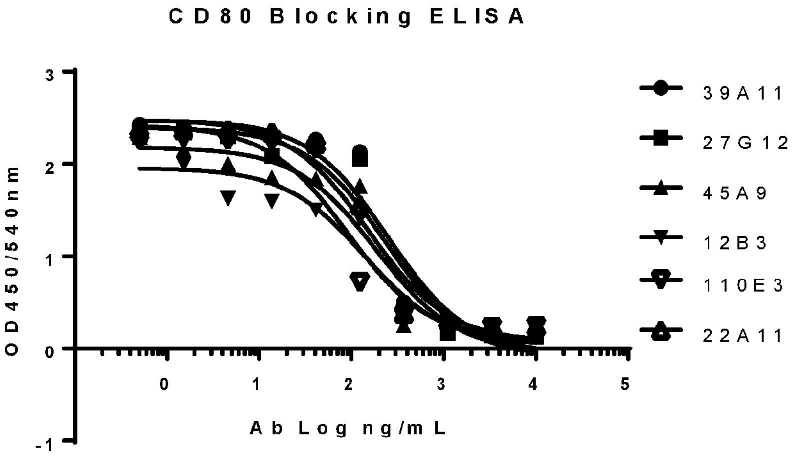
FIG. 3 depicts the antibodies blocking the interaction of canine CD80 with CTLA-4. The figure depicts a plot of the quantity of the individual canine CTLA-4 antibodies in ng/ml (Ab Log) added to cCTLA-4 to interfere with the binding of canine CTLA-4 to CD80. The individual antibodies to canine CTLA-4 are denoted as 39A11, 27G12, 45A9, 12B3, 110E3, and 22A11. As can be seen, the antibodies also can block the interaction of canine CD80 with CTLA-4.
Figure 4A:
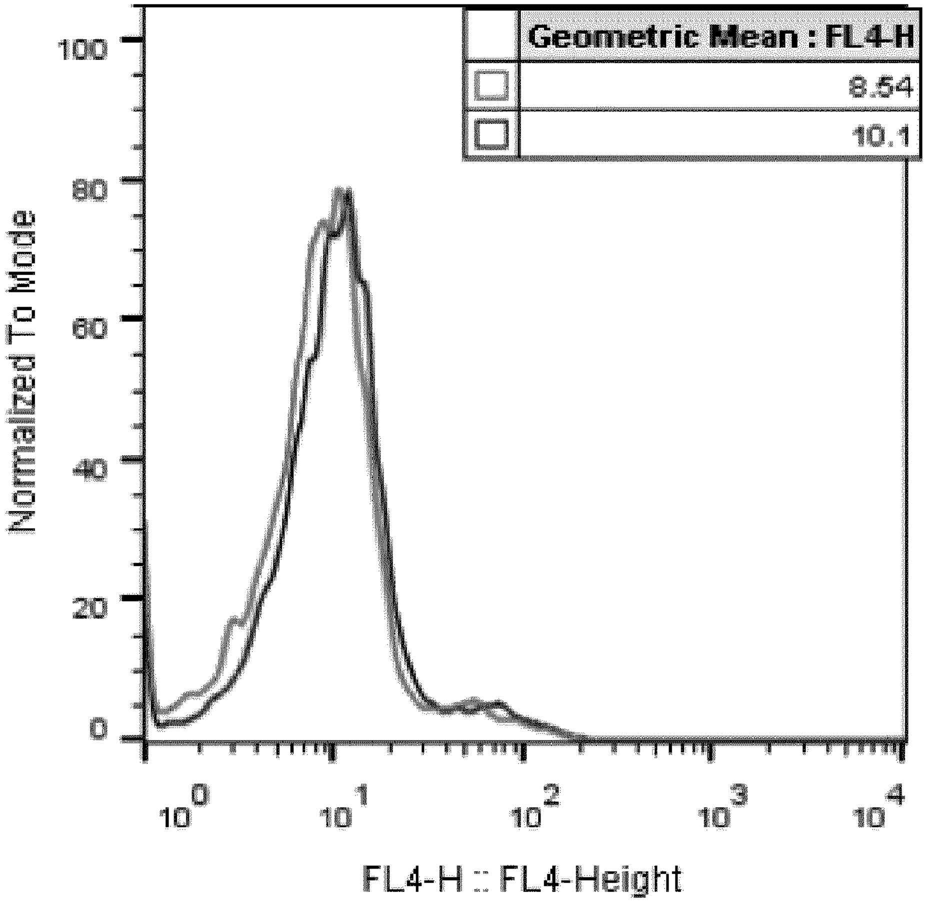
FIGS. 4A-4G depict the antibodies binding to the CHO cells that express canine CTLA-4.
Figure 4B:
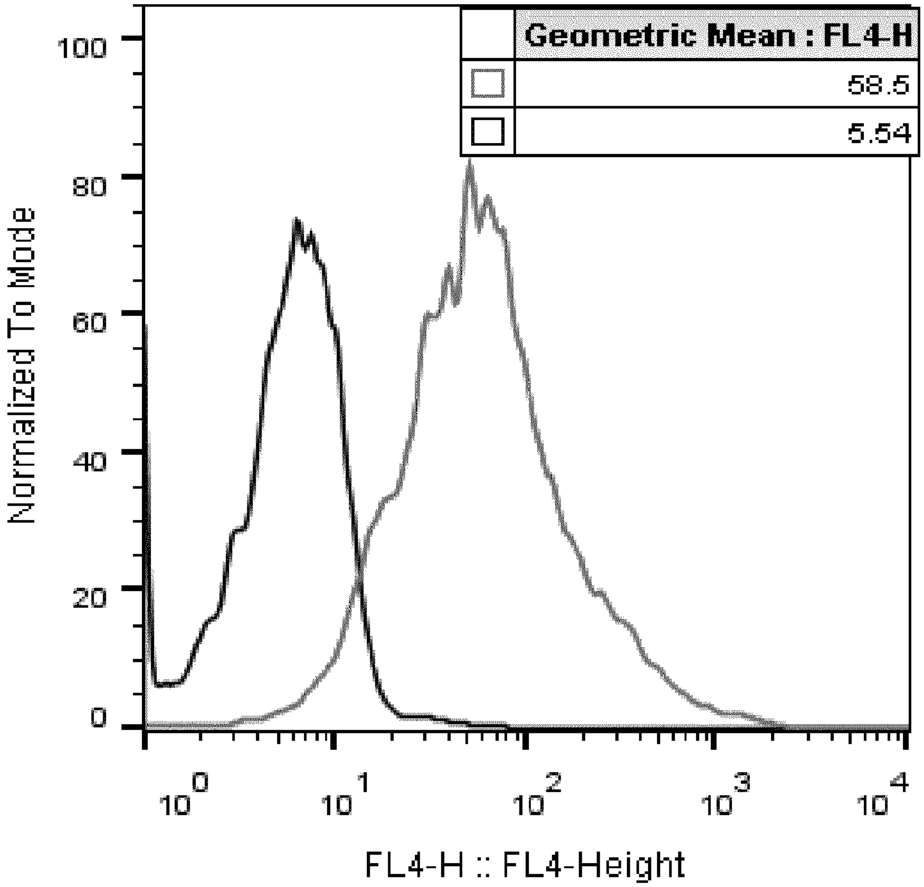
Figure 4C:
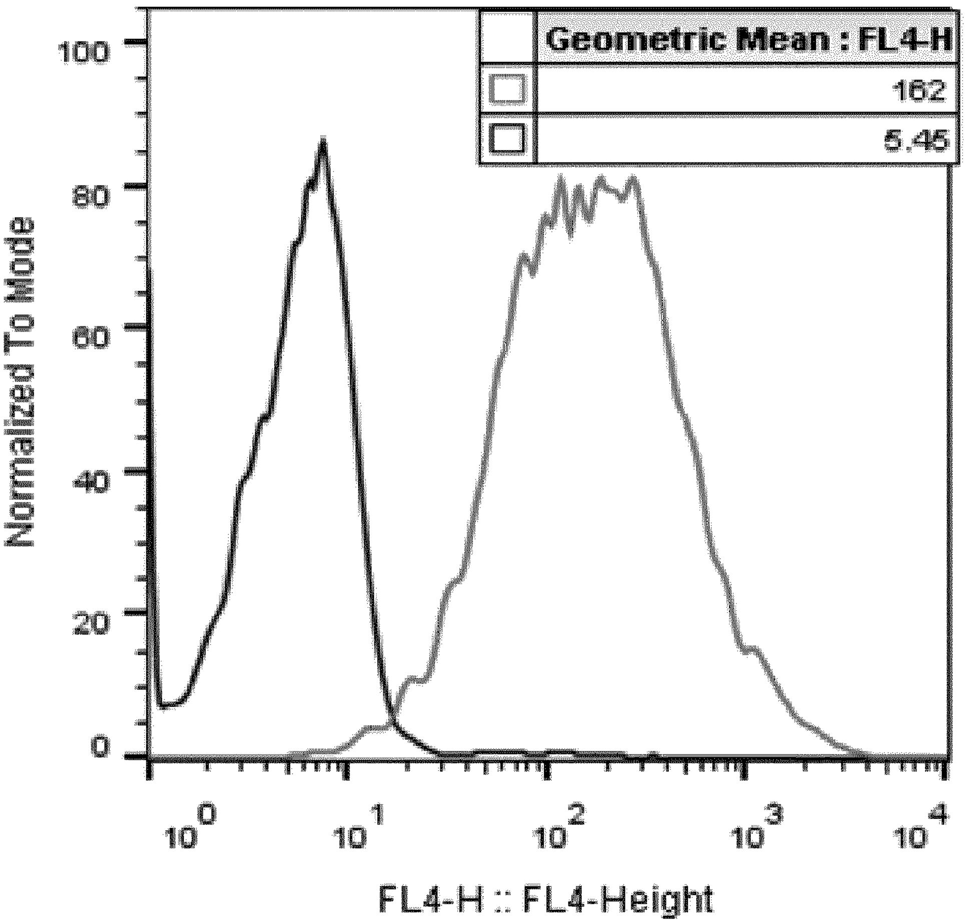
Figure 4D:
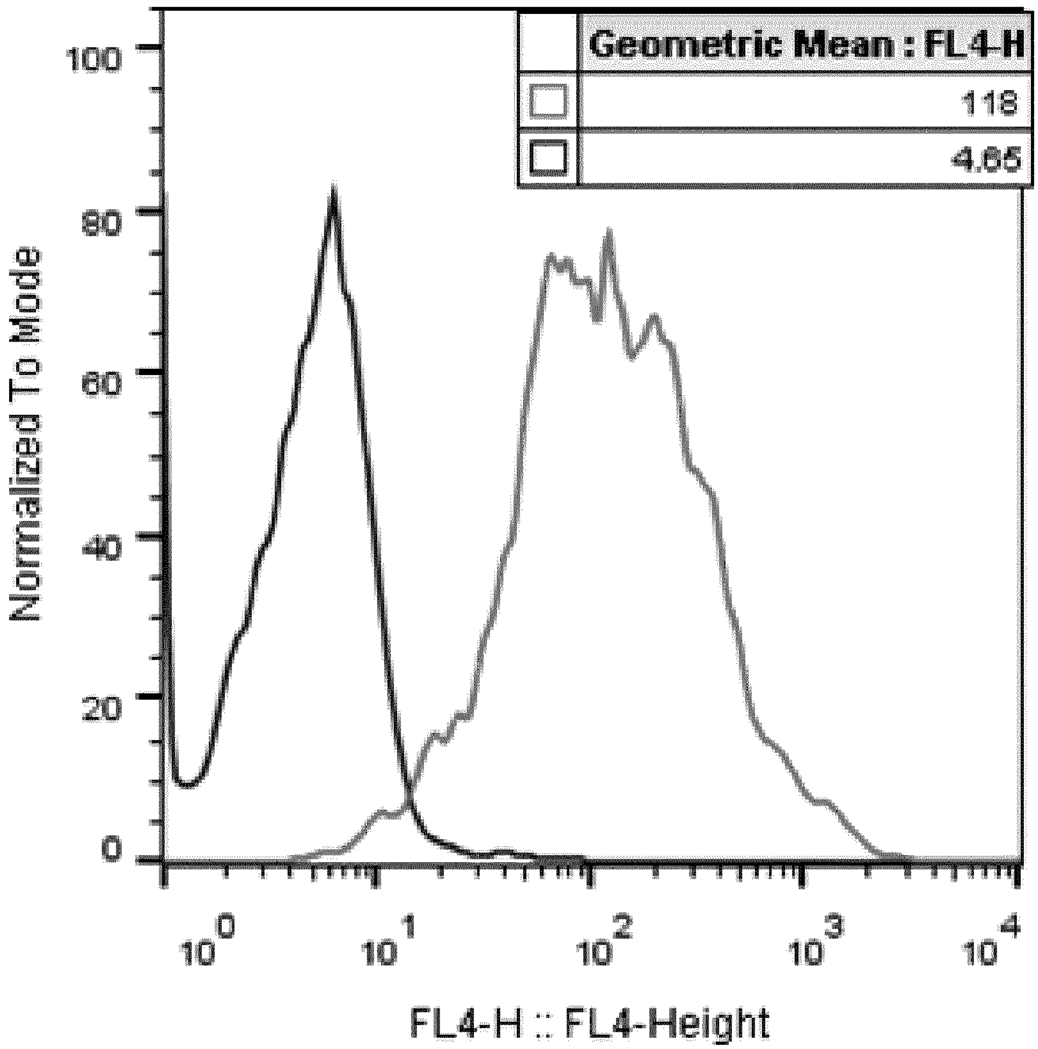
Figure 4E:
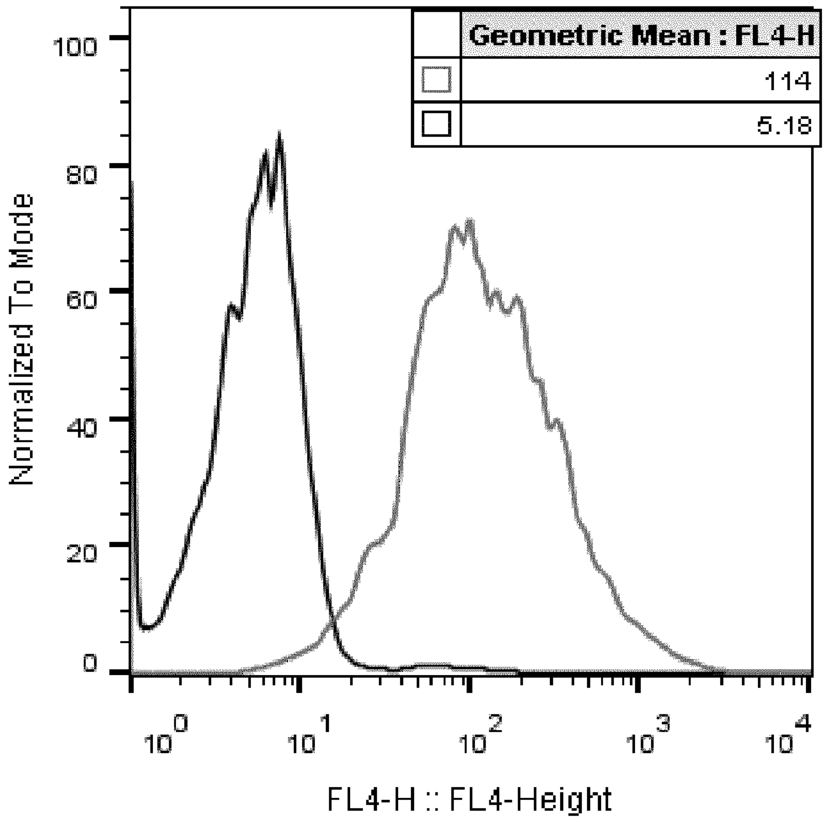
Figure 4F:
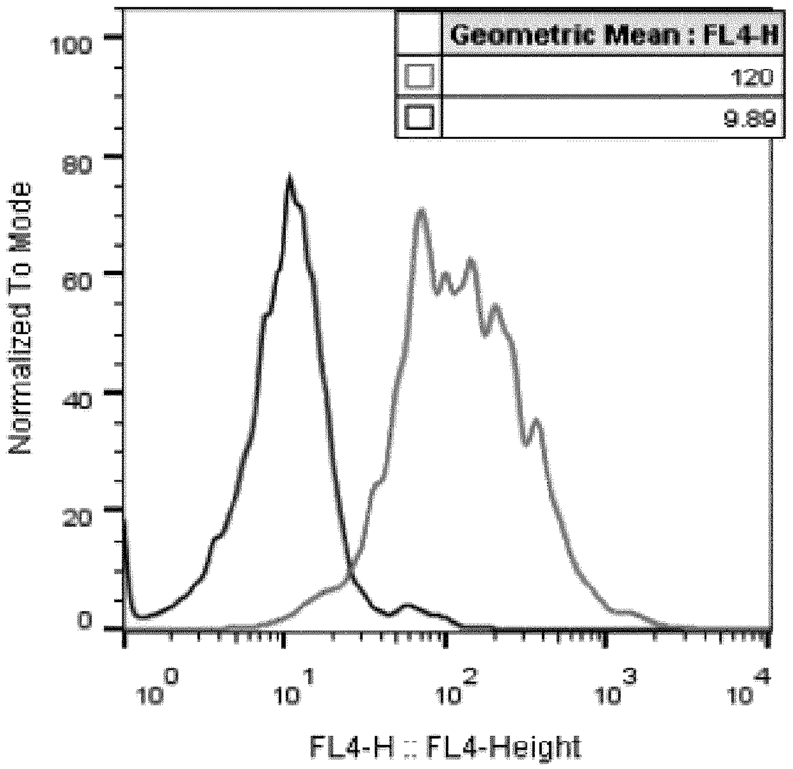
Figure 4G:
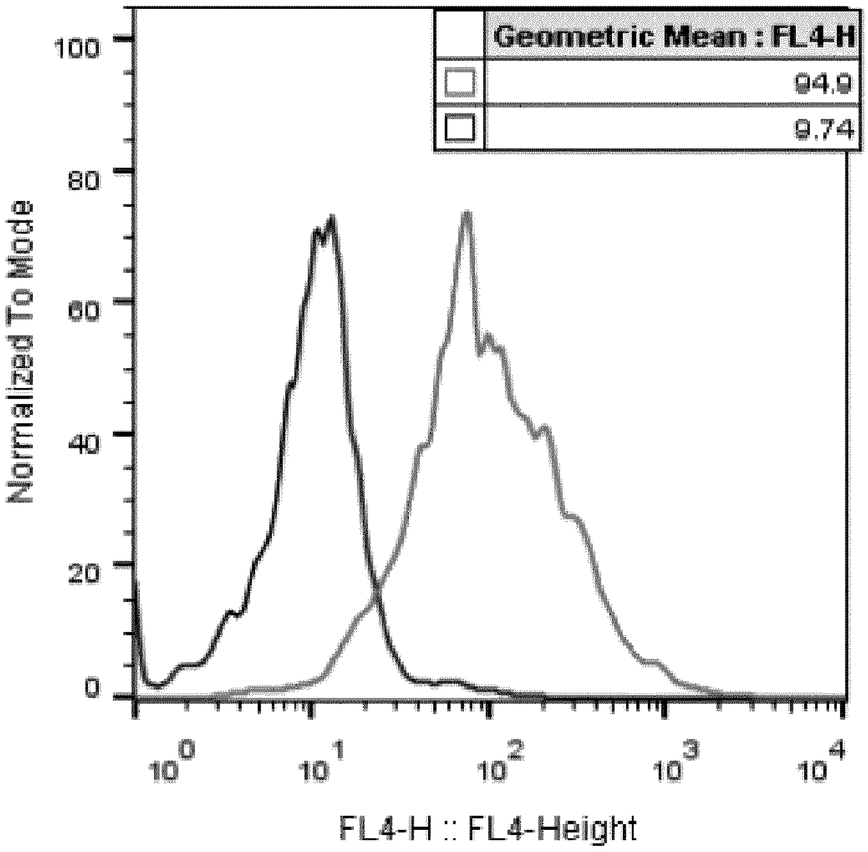

The chimeric antibodies were found to block the interaction of cCTLA-4 with CD86 FIG. 2 and with CD80 [FIG. 3].

Example 5

FACS Assay for Testing Binding Activity of the Chimeric Antibodies on CHO-cCTLA-4

A CHO-K1 cell line stably expressing cCTLA-4 was generated. The cells were used to test antibody binding and blocking activity in FACS flow assay. To test cCTLA-4 binding activity of the chimeric antibodies, the FACS assay was conducted as follows:

1. Grew CHO-K1-cCTLA-4 cells in the culture medium in T-75 flask. The cells are passaged when the cell confluency reaches to 90%.

Culture medium: F12K (Gibco, cat #21127-022), 10% FBS (Gibco, cat #10099-141), and 4 μg/ml puromycin (Gibco, cat #A1113803).

2. Detached the cells by Trypsin-EDTA solution, resuspended the cells in culture medium, and counted the viable cells with more than 95% viability.
3. Spun down the cells, aspirated the supernatant, then resuspended the cells into FACS buffer (Thermo Fisher Scientific, Cat #BDB554656) to $1\times10^7$ cells/mL.
4. Added antibody into 100 μL of the cells, incubated at room temperature for 30 min with gentle shaking.
5. Washed the cells by 3×250 μL of FACS buffer, and resuspended the cells into 100 μL FACS buffer.
6. Stained the cells with FITC conjugated anti-canine IgG, incubated at room temperature for 30 min with gentle shaking.
7. Washed the cells with 3×250 μL of FACS buffer and resuspended the cells into 500 μL FACS buffer.
8. Read 10,000 cells by flow cytometry.

The FACS results show that the chimeric antibody can bind to the CHO-cCTLA-4 cells [see, FIGS. 4A-4G].

Example 6

Interferon Gamma (IFNγ) Generation of Canine PBMC Activated by the Chimeric Antibodies Isolation of Canine Peripheral Blood Mononuclear Cells 1. Collected ~20 mL of whole blood in EDTA or sodium heparin tube.
2. Transferred the blood into a 50 mL polystyrene tube and diluted 50:50 with HBSS (Thermo Fisher Scientific cat #21022CM).
3. Added 15 mL of Ficoll-Plaque Plus to four×50 mL SepMate™ Tubes (STEMCELL Technologies, cat #15460). Then added ~10 mL of the 50:50 diluted blood slowly and to the side of each SepMate™ Tubes containing Ficoll.
4. Centrifuged tubes at 1200×g for 20 minutes.
5. Harvested cells from the gradient interface and transferred the cells to 50 mL polypropylene tube. Added HMS to the 40-45 mL mark and centrifuged the cells at 800×g for 10 minutes.
6. Discarded the supernatant, resuspended the cells in 40-45 mL HMS, and centrifuged the tube again at 800×g for 10 minutes.
7. Discarded the supernatant and resuspended the cells from each tube with 2 mL of Canine Lymphocyte Media (RPMI medium, Lonza, cat #12-167Q). The cells were pooled from the same animal.
8. Took small aliquots of the cell suspension, mixed it with 0.04% Trypan blue and counted the number of cells.
9. Stored the cell suspension at 2-7° C. until it was used, but not longer than 24 hours prior to use.

Cell Proliferation Assay for Canine Peripheral Blood Mononuclear Cells

1. Diluted antibodies in Canine Lymphocyte Media to achieve a final concentration of 40 μg/mL (prepare 160 μg/mL) and sterilized using a 0.2 μm syringe filter. Two-fold Dilute antibodies down a sterile dilution plate and set them aside.
2. Diluted cells to $2.5\times10^6$ cells/mL in Canine Lymphocyte Media and dispensed 100 μL per well of an entire 96-well tissue culture plate.
3. Diluted Con A in Canine Lymphocyte Media to achieve final concentration 250 ng/mL (prepare 1000 ng/mL), sterilized using 0.2 μm syringe filter and added 50 μL to all wells. (Did not add Con A to one column of eight wells for the cell only control and to the wells intended for cells+mAb only controls.)
4. Added 100 μL of Canine Lymphocyte Media per well to cells only wells and 50 μL of media to column containing Con A control wells (Con A+ cells without mAb treatment).
5. Added 50 μL of diluted mAbs to duplicate wells.
6. Incubated plates at 36±2° C., 4.0-6.0% $CO_2$ in a humidified incubator for 68 to 124 hours.

IFNγELISA

1. Following the 68-124 hours incubation, centrifuged the plate at 800×g for 10 minutes.
2. Collected supernatant from each well and pool replicates. These samples may be frozen at ≤−50° C. for later use or tested immediately.
3. Diluted supernatant samples appropriately, if needed, and performed IFN-gamma ELISA according to the instructions of Canine IFN-gamma Quantikine ELISA Kit [R&D Systems Catalog No. CAIF00].

Figure 5:
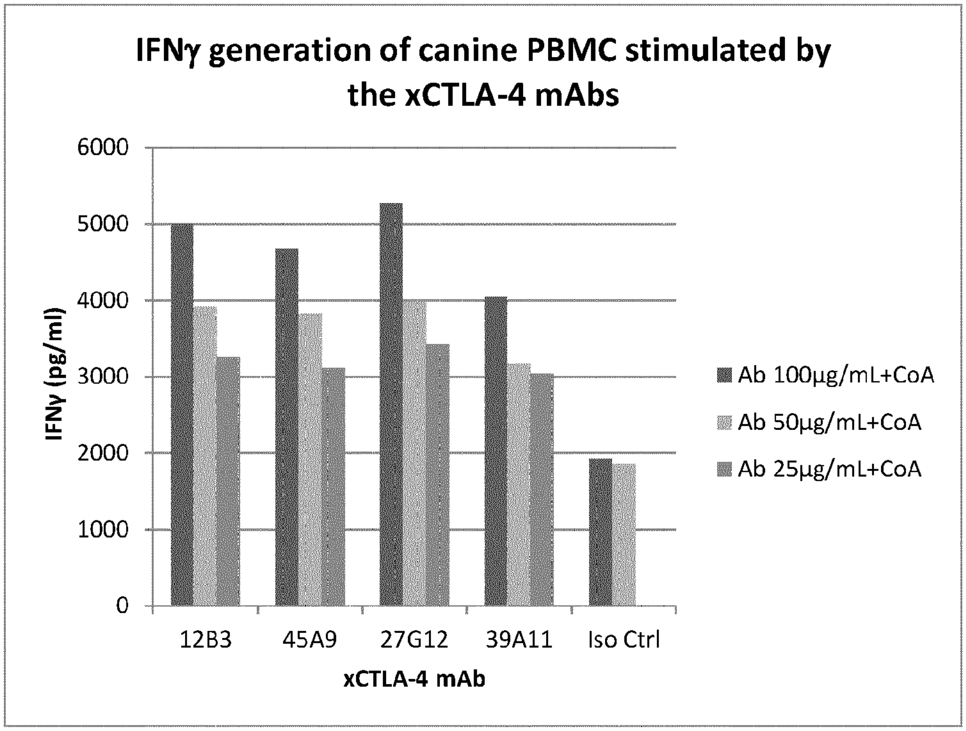
FIG. 5 depicts a bar graph that quantifies three decreasing concentrations of individual canine CTLA-4 antibodies added in 25 μg/mL, 50 μg/mL, or 100 μg/mL (Ab) that activate canine PBMC cells in the presence of concanavalin A (CoA) to produce IFNγ. The antibodies tested are on the abscissa, labeled as CTLA-4 monoclonal antibodies (xCTLA-4 mAb). As can be seen, the antibodies can activate canine PBMC cells to produce IFNγ.

The results demonstrate that the selected antibodies, including 12B3, can activate canine T cells to produce IFNγ [see, FIG. 5 below].

Example 7

Construction of Caninized Anti-cCTLA-4 Monoclonal Antibody 12B3 and 39A11

With their strong binding affinity for cCTLA-4 and their blocking activity on cCTLA-4 with its ligands, CD86 and CD80, murine antibodies 12B3 and 39A11 were selected for making the initial caninized antibodies. To execute the process of caninization, the DNA sequence that encodes the heavy and light chains of canine IgG were determined. The DNA and protein sequence of the canine heavy and light chains are known in the art and can be obtained by searching of the NCBI gene and protein databases. There are four known IgG subtypes of dog IgG and they are referred to as IgGA, IgGB, IgGC, and IgGD. Like human IgG1, canine IgGB has strong effector function. To knock out the effector function of IgGB, a modified IgGB was constructed (IgGBm) removing the native ADCC and CDC functions [see, U.S. Pat. No. 10,106,107 B2, hereby incorporated by reference in its entirety]. There are two types of light chains in canine antibodies referred to as kappa and lambda. Without being bound by any specific approach, the overall process of producing caninized heavy and light chains that can be mixed in different combinations to produce caninized anti-canine CTLA-4 mAbs may involve the following protocol:

i) Identified the CDRs of H and L chains of selected antibodies. Back translated the amino acid sequences of the CDRs into a suitable DNA sequence.
ii) Identified a suitable DNA sequence for H and L chain of canine IgG (e.g., heavy chain of IgGB and light kappa chain).
iii) Identified the DNA sequences encoding the endogenous CDRs of canine IgG H and L chains DNA of the above sequence.
iv) Replaced the DNA sequence encoding the endogenous canine H and L chain CDRs with DNA sequences encoding the CDRs of selected antibodies. Also, optionally replaced the DNA encoding some canine framework amino acid residues with DNA encoding selected amino acid residues from selected antibody framework regions.

v) Synthesized the DNA from step (iv) and cloned it into a suitable expression plasmid.

vi) Transfected the synthesized plasmids into HEK 293 cells.

vii) Purified expressed caninized antibody from HEK 293 supernatant.

viii) Tested purified caninized antibody for binding to canine CTLA-4.

The nucleotide and amino acid sequences of the CDRs of 12B3 and 39A11 are listed in Table 3 below.

TABLE 3

NUCLEOTIDE AND AMINO ACID SEQUENCES OF THE CDRS USED FOR CANINIZED ANTIBODIES

| AB | CDR | SEQUENCE | TYPE | SEQ ID NO: |
|---|---|---|---|---|
| 12B3 | | | | |
| | H-1 | aactatggaatgaac | NA | 85 |
| | H-1 | NYGMN | AA | 86 |
| | H-2 | tggataaacacctacactgga gagccaacatatgctgatgact tcaaggga | NA | 87 |
| | H-2 | WINTYTGEPTYADDFKG | AA | 88 |
| | H-3 | cggtcaatttattacccgtac | NA | 89 |
| | H-3 | RSIYYPY | AA | 90 |
| | L-1 | agatctagtcagagcattgta tatagtaatggaaacacctat ttagaa | NA | 91 |
| | L-1 | RSSQSIVYSNGNTYLE | AA | 92 |
| | L-2 | aaagtttccaaccgattttct | NA | 93 |
| | L-2 | KVSNRFS | AA | 94 |
| | L-3 | tttcaaggttcacatgttccgtggacg | NA | 95 |
| | L-3 | FQGSHVPWT | AA | 96 |
| 39A11 | | | | |
| | H-1 | gattactacatgagc | NA | 97 |
| | H-1 | DYYMS | AA | 98 |
| | H-2 | tttattagaaacaaagctaatggtta cacaacagagtacagcgcatctctga agggt | NA | 99 |
| | H-2 | FIRNKANGYTTEYSASLKG | AA | 100 |
| | H-3 | tttgggttaatgtactactttgactac | NA | 101 |
| | H-3 | FGLMYYFDY | AA | 102 |
| | L-1 | agggccagctcaagtgtaag ttccagttacttgcac | NA | 103 |
| | L-1 | RASSSVSSSYLH | AA | 104 |
| | L-2 | agcacatccaacttggcttct | NA | 105 |
| | L-2 | STSNLAS | AA | 106 |
| | L-3 | cagcagtacagtggtctcccactcacg | NA | 107 |
| | L-3 | QQYSGLPLT | AA | 108 |

A set of caninized Light and Heavy chain sequences were constructed. Their Sequence Identification Numbers are provided in Tables 4-6 below.

TABLE 4

SEQ ID NOS: OF CANINIZED LIGHT CHAINS OF 12B3 AND 39A11

| Caninized light chain | SEQ ID NO. (DNA)[2] | SEQ ID NO. (Amino acid)[1] |
|---|---|---|
| 12B3 VL1 | 49 | 50 |
| 12B3 VL2 | 51 | 52 |
| 12B3 VL3 | 53 | 54 |
| 39A11 VL1 | 55 | 56 |
| 39A11 VL2 | 57 | 58 |
| 39A11 VL3 | 59 | 60 |

[1]The CDRs are underlined;
[2]the variable regions are in bold in the sequences that follow.

TABLE 5

SEQ ID NOS: OF THE CANINIZED HEAVY CHAIN OF 12B3 AND 39A11 WITH WILD TYPE IgGB (Natural)

| Caninized heavy chain | SEQ ID NO. (DNA)[2] | SEQ ID NO. (Amino acid)[1] |
|---|---|---|
| 12B3 VH1 | 61 | 62 |
| 12B3 VH2 | 63 | 64 |
| 12B3 VH3 | 65 | 66 |
| 39A11 VH1 | 67 | 68 |
| 39A11 VH2 | 69 | 70 |
| 39A11 VH3 | 71 | 72 |

[1]The CDRs are underlined;
[2]the variable regions are in bold in the sequences that follow.

TABLE 6

SEQ ID NOS: OF CANINIZED HEAVY CHAIN OF 12B3 AND 39A11 WITH IgGBm (modified IgGB)

| Caninized Heavy chain | SEQ ID NO. (DNA)[2] | SEQ ID NO. (Amino acid)[1] |
|---|---|---|
| 12B3 VH1 | 73 | 74 |
| 12B3 VH2 | 75 | 76 |
| 12B3 VH3 | 77 | 78 |
| 39A11 VH1 | 79 | 80 |
| 39A11 VH2 | 81 | 82 |
| 39A11 VH3 | 83 | 84 |

[1]The CDRs are underlined;
[2]the variable regions are in bold in the sequences that follow.

TABLE 7

RELATED PRIOR ART SEQUENCES

| Protein | SEQ ID NO. (Nucleic Acid) | SEQ ID NO. (Amino acid) |
|---|---|---|
| Canine CTLA-4, with signal sequence | 125 | 126 |
| Canine IgGBm | | 127 |
| IgGA (hinge) | | 128 |
| IgGB (hinge) | | 129 |
| IgGC (hinge) | | 130 |
| Modified IgGD (hinge) | | 131 |
| Canine CTLA-4, without signal sequence | | 138 |

Figure 6:
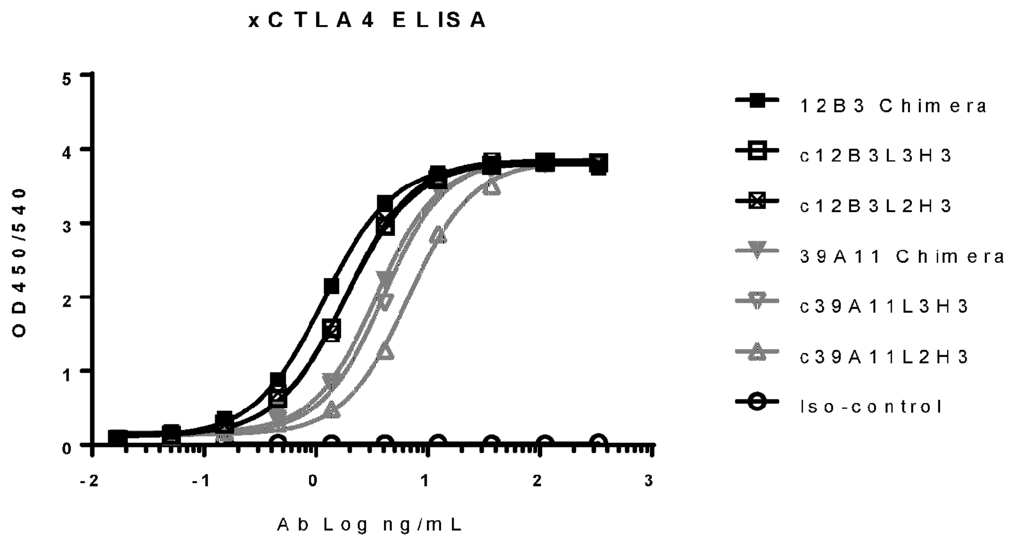
FIG. 6 depicts a plot of the quantity of CTLA-4 monoclonal antibodies (xCTLA-4; Ab Log ng/mL) that have same reactivity with canine CTLA-4 as the parental antibodies. The ELISA results indicate that both 12B3 and 39A11 were successfully caninized. Caninized c12B3L3H2 and L3H3 possess similar reactivity with cCTLA-4 as parental 12B3 and caninized c39A11L3H3 possesses similar reactivity with cCTLA-4 as parental 39A11.

The present invention provides the caninized antibodies of 12B3 and 39A11 formed by the combination of caninized heavy and light chains of each antibody listed in the tables above; such antibodies demonstrate a particularly tight binding with cCTLA-4. As indicated in FIG. 6, the ELISA results indicate that both 12B3 and 39A11 are successfully caninized. Caninized c12B3L3H2 and L3H3 possess similar reactivity with cCTLA-4 as parental 12B3; caninized c39A11L3H3 possesses similar reactivity with cCTLA-4 as parental 39A11. The chimeras of 12B3 and 39A11 represent their parental antibodies.

NUCLEOTIDE (NA) and AMINO ACID (AA) SEQUENCES

SEQ ID NO: 1:
Mouse monoclonal antibody 12B3 heavy chain variable region NA sequence
cagatccagttggtgcagtctggacctgagctgaagaagcctggagagacagtcaagatctcctgcaagg cttctgggtataccttcacaaactatggaatgaactgggtgaagcaggctccaggaaagggtttaaagtg gatgggctggataaacacctacactggagagccaacatatgctgatgacttcaagggacggtttgccttc tctttggaaacctctgccagcactgcctatttgcagatcaacaacctcaaaaatgaggacatggctacat atttctgtgcaagacggtcaatttattacccgtactggggccaaggcaccactctcacagtctcctca SEQ ID NO: 2:
Mouse monoclonal antibody 12B3 heavy chain variable region AA sequence
QIQLVQSGPELKKPGETVKISCKASGYTFTNYGMNWVKQAPGKGLKWMGWINTYTGEPTYADDFKGRFAF

SLETSASTAYLQINNLKNEDMATYFCARRSIYYPYWGQGTTLTVSS

SEQ ID NO: 3:
Mouse monoclonal antibody 27G12 heavy chain variable region NA sequence
cagatccagttggtacagtctggacctgagctgaagaagcctggagagacagtcaagatctcctgcaagg cttctgggtataccttcacaacctatggagtgagctgggtgaaacaggctccaggaaagggtttaaggtg gatgggctggataaacacctactctggaatgccaacatatgttgatgacttcaagggacggtttgccttc tctttggaaacctctgccagcactgcctttttgcagatcaacaacctcaaaaatgaggacacggctatat atttctgtgcaagacggggtatctcctttgactactggggccaaggcaccactctcacagtctcctca SEQ ID NO: 4:
Mouse monoclonal antibody 27G12 heavy chain variable region AA sequence
QIQLVQSGPELKKPGETVKISCKASGYTFTTYGVSWVKQAPGKGLRWMGWINTYSGMPTYVDDFKGRFAF

SLETSASTAFLQINNLKNEDTAIYFCARRGISFDYWGQGTTLTVSS

SEQ ID NO: 5:
Mouse monoclonal antibody 39A11 heavy chain variable region NA sequence
gaggtgaagctggtggagtctggaggaggcttggtacagcctgggggttccctgagtctctcctgtgcaa cttctggattcaccttcagtgattactacatgagctgggtccgccagtctccggggaaggcacttgagtg gatgggttttattagaaacaaagctaatggttacacaacagagtacagcgcatctctgaagggtcggttc accatctccagagataattcccaaagcatcctctatcttcaaatgaatgtcctgagagctgaggacagtg ccacttattactgtgtaagatttgggttaatgtactactttgactactggggccaaggcaccactctcac agtctcctca SEQ ID NO: 6:
Mouse monoclonal antibody 39A11 heavy chain variable region AA sequence
EVKLVESGGGLVQPGGSLSLSCATSGFTFSDYYMSWVRQSPGKALEWMGFIRNKANGYTTEYSASLKGRF

TISRDNSQSILYLQMNVLRAEDSATYYCVRFGLMYYFDYWGQGTTLTVSS

SEQ ID NO: 7:
Mouse monoclonal antibody 45A9 heavy chain variable region NA sequence
cagatccagttggtgcagtctggacctgagctgaagaagcctggagagacagtcaagatctcctgcaagg cttctgggtataccttcacaaactatggaatgaactgggtgaagcaggctccaggaaagggtttaaagtg gatgggctggataaacacctacactggagagccaacatatgctgatgacttcaagggacggtttgccttc tctttggaaacctctgccagcactgcctatttgcagatcaacaacctcaaaaatgaggacacggctacat atttctgtgcaagaagggggacctactataggccctggggccaaggcaccactctcacagtctcctca SEQ ID NO: 8:
Mouse monoclonal antibody 45A9 heavy chain variable region AA sequence
QIQLVQSGPELKKPGETVKISCKASGYTFTNYGMNWVKQAPGKGLKWMGWINTYTGEPTYADDFKGRFAF

SLETSASTAYLQINNLKNEDTATYFCARRGTYYRPWGQGTTLTVSS

-continued

| NUCLEOTIDE (NA) and AMINO ACID (AA) SEQUENCES |
|---|
| SEQ ID NO: 9:<br>Mouse monoclonal antibody 110E3 heavy chain variable region NA sequence<br>cagatccagttggtgcagtctggacctgagctgaagaagcctggagagacagtcaagatctcctgcaagg<br>cttctggatataccttcacaaactatggaatgaactgggtgaagcaggctccaggaaagggtttaaagtg<br>gatgggctggataaacacctacactggagagccaacatatgctgatgacttcaagggacgggttgccttc<br>tctttggaaacctctgccagcactgcctttttgcagatcaacaacctcaaaaatgaggacacggctacat<br>atttctgtgcaaggcggggggtacgactggactactggggccaaggcaccactctcacagtctcctca |
| SEQ ID NO: 10:<br>Mouse monoclonal antibody 110E3 heavy chain variable region AA sequence<br>QIQLVQSGPELKKPGETVKISCKASGYTFTNYGMNWVKQAPGKGLKWMGWINTYTGEPTYADDFKGRVAF<br>SLETSASTAFLQINNLKNEDTATYFCARRGVRLDYWGQGTTLTVSS |
| SEQ ID NO: 11:<br>Mouse monoclonal antibody 22A 11 heavy chain variable region NA sequence<br>caggtccaactgcagcagcctgggactgaactggtgaagcctggggcttcagtgaagctgtcctgcaagg<br>cctctggctataccttcaccagctactggatgcactgggtgaagcagaggcctggacaaggccttgagtg<br>gattggaaatatcaatcctagcaatggtggtactaggttcaatgagaagttcaagaacaaggccacactg<br>actgaagacaaatcctccagcacagcctacatgcagctcagtagcctgacatctgaggactctgcggtct<br>attattgtgcaagatcgaactacggtagtggctgggcctggtttgcttactggggccaagggactctggt<br>cactgtctctgca |
| SEQ ID NO: 12:<br>Mouse monoclonal antibody 22A11 heavy chain variable region AA sequence<br>QVQLQQPGTELVKPGASVKLSCKASGYTFTSYWMHWVKQRPGQGLEWIGNINPSNGGTRFNEKEKNKATL<br>TEDKSSSTAYMQLSSLTSEDSAVYYCARSNYGSGWAWFAYWGQGTLVTVSA |
| SEQ ID NO: 13:<br>Mouse monoclonal antibody 12B3 light chain variable region NA sequence<br>gatgttttgatgacccaaactccactctccctgcctgtcagtcttggagatcaagcctccatctcttgca<br>gatctagtcagagcattgtatatagtaatggaaacacctatttagaatggtacctgcagaaaccaggcca<br>gtctccaaagctcctgatctacaaagtttccaaccgattttctggggtcccagacaggttcagtggcagt<br>ggatcagggacagatttcacactcaagatcagcagagtggaggctgaggatctgggagtttattactgct<br>ttcaaggttcacatgttccgtggacgttcggtggaggcaccaagctggaaatcaaa |
| SEQ ID NO: 14:<br>Mouse monoclonal antibody 12B3 light chain variable region AA sequence<br>DVLMTQTPLSLPVSLGDQASISCRSSQSIVYSNGNTYLEWYLQKPGQSPKLLIYKVSNRFSGVPDRFSGS<br>GSGTDFTLKISRVEAEDLGVYYCFQGSHVPWTFGGGTKLEIK |
| SEQ ID NO: 15:<br>Mouse monoclonal antibody 27G12 light chain variable region NA sequence<br>Gatgttttgatgacccagactccactctccctgcctgtcagtcttggagatcacgcctccatctcttgca<br>aatctagtcagagcattgtatatattaatggaaacacctatttagaatggtacctgcagaagccaggcca<br>gtctccaaagctcctgatctacaaagtttccaaacgattttctggggtcccagacaggttcagtggcagt<br>ggatcagggacagatttcacactcaagatcagcagagtggaggctgaggatctgggagtttattactgct<br>ttcaaggttcacatgttccgtggacgttcggtggaggcaccaagctggaaatcaaa |
| SEQ ID NO: 16:<br>Mouse monoclonal antibody 27G12 light chain variable region AA sequence<br>DVLMTQTPLSLPVSLGDHASISCKSSQSIVYINGNTYLEWYLQKPGQSPKLLIYKVSKRFSGVPDRFSGS<br>GSGTDFTLKISRVEAEDLGVYYCFQGSHVPWTFGGGTKLEIK |

-continued

| NUCLEOTIDE (NA) and AMINO ACID (AA) SEQUENCES |
|---|

SEQ ID NO: 17:
Mouse monoclonal antibody 39A11 light chain variable region NA sequence
gaaaatgtgctcatccagtctccagcaatcatgtctgcttctccaggggaaaaggtcaccatgacctgca gggccagctcaagtgtaagttccagttacttgcactggtaccagcagaagtcaggtgcctcccccaaact ctggatttttagcacatccaacttggcttctggagtccctgctcgcttcagtggcagtgggtctgggacc tcttattctctcacaatcaacagtgtggaggctgaagatgctgccacttattactgccagcagtacagtg gtctcccactcacgttcggaggggggaccaagctggaaataaaa SEQ ID NO: 18:
Mouse monoclonal antibody 39A11 light chain variable region AA sequence
ENVLIQSPAIMSASPGEKVTMTCRASSSVSSSYLHWYQQKSGASPKLWIFSTSNLASGVPARFSGSGSGT

SYSLTINSVEAEDAATYYCQQYSGLPLTFGGGTKLEIK

SEQ ID NO: 19:
Mouse monoclonal antibody 45A9 light chain variable region NA sequence
gatgttttgatgacccaaactccactctccctgcctgtcagtcttggagatcaagcctccatctcttgca gatctagtcagagtattgtatatagtcatggaaacacctatttagaatggtacctgcagaaaccaggcca gtctccaaaggtcctgatctacaaagtttccaaccgattttctggggtcccagacaggttcagtggcagt ggatcagggacagatttcacactcaagatcagcagagtggaggctgaggatctgggagtttattactgct ttcaaggttcacatgttccgtggacgttcggtggaggcaccaagctggaaatcaaa SEQ ID NO: 20:
Mouse monoclonal antibody 45A9 light chain variable region AA sequence
DVLMTQTPLSLPVSLGDQASISCRSSQSIVYSHGNTYLEWYLQKPGQSPKVLIYKVSNRFSGVPDRFSGS

GSGTDFTLKISRVEAEDLGVYYCFQGSHVPWTFGGGTKLEIK

SEQ ID NO: 21:
Mouse monoclonal antibody 110E3 light chain variable region NA sequence
gatgttttgatgacccaaactccactctccctgcctgtcagtcttggagatcaagcctccatctcttgca gatctagtcagagcattgtatatattagtggaagcacctatttagaatggtatctgcagaaaccaggcca gtctccaaagctcctgatctacaaagtttccagtcgattttctggggtcccagacaggttcagtggcagt ggatcagggacagatttcacactcaagatcagcagagtggaggctgaggatctgggagtttattactgct ttcaaggttcacatgttccgtggacgttcggtggaggcaccaagctggaaatcaaa SEQ ID NO: 22:
Mouse monoclonal antibody 110E3 light chain variable region AA sequence
DVLMTQTPLSLPVSLGDQASISCRSSQSIVYISGSTYLEWYLQKPGQSPKLLIYKVSSRFSGVPDRFSGS

GSGTDFTLKISRVEAEDLGVYYCFQGSHVPWTFGGGTKLEIK

SEQ ID NO: 23:
Mouse monoclonal antibody 22A11 light chain variable region NA sequence
gacatccagatgaaccagtctccatccagtctgtctgcatcccttggagacacaattaccatcacttgcc atgccagtcagaacattaatgtttggttaagctggtaccagcagaaaccaggaaatattcctaaactttt gatctataagtcttccaacttgcacacaggcgtcccatcaaggtttagtggcagtggatctggaacaggt ttcacattaaccatcagcagcctgcagcctgaagacattgccacttactactgtcaacagggtcaaagtt atccgtggacgttcggtggaggcaccaagctggaaatcaaa SEQ ID NO: 24:
Mouse monoclonal antibody 22A11 light chain variable region AA sequence
DIQMNQSPSSLSASLGDTITITCHASQNINVWLSWYQQKPGNIPKLLIYKSSNLHTGVPSRFSGSGSGTG

FTLTISSLQPEDIATYYCQQGQSYPWTFGGGTKLEIK

-continued

| NUCLEOTIDE (NA) and AMINO ACID (AA) SEQUENCES |
|---|

SEQ ID NO: 25:
Mouse-canine chimeric antibody 12B3 heavy chain NA sequence
cagatccagttggtgcagtctggacctgagctgaagaagcctggagagacagtcaagatctcctgcaagg cttctgggtataccttcacaaactatggaatgaactgggtgaagcaggctccaggaaagggtttaaagtg gatgggctggataaacacctacactggagagccaacatatgctgatgacttcaagggacggtttgccttc tctttggaaacctctgccagcactgcctatttgcagatcaacaacctcaaaaatgaggacatggctacat atttctgtgcaagacggtcaatttattacccgtactggggccaaggcaccactctcacagtctcctcagc gagcaccaccgcgccgagcgtgtttccgctggcgccgagctgcggcagcaccagcggcagcaccgtggcg ctggcgtgcctggtgagcggctattttccggaaccggtgaccgtgagctggaacagcggcagcctgacca gcggcgtgcatacctttccgagcgtgctgcagagcagcggcctgtatagcctgagcagcatggtgaccgt gccgagcagccgctggccgagcgaaacctttacctgcaacgtggcgcatccggcgagcaaaaccaaagtg gataaaccggtgccgaaacgcgaaaacggccgcgtgccgcgcccgccggattgcccgaaatgcccggcgc cggaaatgctgggcggcccgagcgtgtttatttttccgccgaaaccgaaagataccctgctgattgcgcg caccccggaagtgacctgcgtggtggtggatctggatccggaagatccggaagtgcagattagctggttt gtggatggcaaacagatgcagaccgcgaaaacccagccgcgcgaagaacagtttaacggcacctatcgcg tggtgagcgtgctgccgattggccatcaggattggctgaaaggcaaacagtttacctgcaaagtgaacaa caaagcgctgccgagcccgattgaacgcaccattagcaaagcgcgcggccaggcgcatcagccgagcgtg tatgtgctgccgccgagccgcgaagaactgagcaaaaacaccgtgagcctgacctgcctgattaaagatt tttttccgccggatattgatgtggaatggcagagcaacggccagcaggaaccggaaagcaaatatcgcac caccccgccgcagctggatgaagatggcagctattttctgtatagcaaactgagcgtggataaaagccgc tggcagcgcggcgatacctttatttgcgcggtgatgcatgaagcgctgcataaccattatacccaggaaa gcctgagccatagcccgggcaaa SEQ ID NO: 26:
Mouse-canine chimeric antibody 12B3 heavy chain AA sequence
QIQLVQSGPELKKPGETVKISCKASGYTFTNYGMNWVKQAPGKGLKWMGWINTYTGEPTYADDFKGRFAF

SLETSASTAYLQINNLKNEDMATYFCARRSIYYPYWGQGTTLTVSSASTTAPSVFPLAPSCGSTSGSTVA

LACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVDLDPEDPEVQISWF

VDGKQMQTAKTQPREEQFNGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

SEQ ID NO: 27:
Mouse-canine chimeric antibody 27G12 heavy chain NA sequence
cagatccagttggtacagtctggacctgagctgaagaagcctggagagacagtcaagatctcctgcaagg cttctgggtataccttcacaacctatggagtgagctgggtgaaacaggctccaggaaagggtttaaggtg gatgggctggataaacacctactctggaatgccaacatatgttgatgacttcaagggacggtttgccttc tctttggaaacctctgccagcactgcctttttgcagatcaacaacctcaaaaatgaggacacggctatat atttctgtgcaagacggggtatctcctttgactactggggccaaggcaccactctcacagtctcctcagc gagcaccaccgcgccgagcgtgtttccgctggcgccgagctgcggcagcaccagcggcagcaccgtggcg ctggcgtgcctggtgagcggctattttccggaaccggtgaccgtgagctggaacagcggcagcctgacca gcggcgtgcatacctttccgagcgtgctgcagagcagcggcctgtatagcctgagcagcatggtgaccgt -continued

| NUCLEOTIDE (NA) and AMINO ACID (AA) SEQUENCES |
|---|
| gccgagcagccgctggccgagcgaaacctttacctgcaacgtggcgcatccggcgagcaaaaccaaagtg |
| gataaaccggtgccgaaacgcgaaaacggccgcgtgccgcgcccgccggattgcccgaaatgcccggcgc |
| cggaaatgctgggcggcccgagcgtgtttatttttccgccgaaaccgaaagataccctgctgattgcgcg |
| caccccggaagtgacctgcgtggtggtggatctggatccggaagatccggaagtgcagattagctggttt |
| gtggatggcaaacagatgcagaccgcgaaaacccagccgcgcgaagaacagtttaacggcacctatcgcg |
| tggtgagcgtgctgccgattggccatcaggattggctgaaaggcaaacagtttacctgcaaagtgaacaa |
| caaagcgctgccgagcccgattgaacgcaccattagcaaagcgcgcggccaggcgcatcagccgagcgtg |
| tatgtgctgccgccgagccgcgaagaactgagcaaaaacaccgtgagcctgacctgcctgattaaagatt |
| tttttccgccggatattgatgtggaatggcagagcaacggccagcaggaaccggaaagcaaatatcgcac |
| caccccgccgcagctggatgaagatggcagctattttctgtatagcaaactgagcgtggataaaagccgc |
| tggcagcgcggcgatacctttatttgcgcggtgatgcatgaagcgctgcataaccattatacccaggaaa |
| gcctgagccatagcccgggcaaa |
| SEQ ID NO: 28:<br>Mouse-canine chimeric antibody 27G12 heavy chain AA sequence<br>**QIQLVQSGPELKKPGETVKISCKASGYTFTTYGVSWVKQAPGKGLRWMGWINTYSGMPTYVDDFKGRFAF** |
| **SLETSASTAFLQINNLKNEDTAIYFCARRGISFDYWGQGTTLTVSS**ASTTAPSVFPLAPSCGSTSGSTVA |
| LACLVSGYFPEPVTVSWNSGSLTSGVHTFPSVLQSSGLYSLSSMVTVPSSRWPSETFTCNVAHPASKTKV |
| DKPVPKRENGRVPRPPDCPKCPAPEMLGGPSVFIFPPKPKDTLLIARTPEVTCVVVDLDPEDPEVQISWF |
| VDGKQMQTAKTQPREEQFNGTYRVVSVLPIGHQDWLKGKQFTCKVNNKALPSPIERTISKARGQAHQPSV |
| YVLPPSREELSKNTVSLTCLIKDFFPPDIDVEWQSNGQQEPESKYRTTPPQLDEDGSYFLYSKLSVDKSR |
| WQRGDTFICAVMHEALHNHYTQESLSHSPGK |
| SEQ ID NO: 29:<br>Mouse-canine chimeric antibody 39A11 heavy chain NA sequence<br>**gaggtgaagctggtggagtctggaggaggcttggtacagcctggggggttccctgagtctctcctgtgcaa** |
| **cttctggattcaccttcagtgattactacatgagctgggtccgccagtctccggggaaggcacttgagtg** |
| **gatgggttttattagaaacaaagctaatggttacacaacagagtacagcgcatctctgaagggtcggttc** |
| **accatctccagagataattcccaaagcatcctctatcttcaaatgaatgtcctgagagctgaggacagtg** |
| **ccacttattactgtgtaagatttgggttaatgtactactttgactactggggccaaggcaccactctcac** |
| **agtctcctca**gcgagcaccaccgcgccgagcgtgtttccgctggcgccgagctgcggcagcaccagcggc |
| agcaccgtggcgctggcgtgcctggtgagcggctattttccggaaccggtgaccgtgagctggaacagcg |
| gcagcctgaccagcggcgtgcatacctttccgagcgtgctgcagagcagcggcctgtatagcctgagcag |
| catggtgaccgtgccgagcagccgctggccgagcgaaacctttacctgcaacgtggcgcatccggcgagc |
| aaaaccaaagtggataaaccggtgccgaaacgcgaaaacggccgcgtgccgcgcccgccggattgcccga |
| aatgcccggcgccggaaatgctgggcggcccgagcgtgtttatttttccgccgaaaccgaaagataccct |
| gctgattgcgcgcaccccggaagtgacctgcgtggtggtggatctggatccggaagatccggaagtgcag |
| attagctggtttgtggatggcaaacagatgcagaccgcgaaaacccagccgcgcgaagaacagtttaacg |
| gcacctatcgcgtggtgagcgtgctgccgattggccatcaggattggctgaaaggcaaacagtttacctg |
| caaagtgaacaacaaagcgctgccgagcccgattgaacgcaccattagcaaagcgcgcggccaggcgcat |
| cagccgagcgtgtatgtgctgccgccgagccgcgaagaactgagcaaaaacaccgtgagcctgacctgcc |
| tgattaaagatttttttccgccggatattgatgtggaatggcagagcaacggccagcaggaaccggaaag |
| caaatatcgcaccaccccgccgcagctggatgaagatggcagctattttctgtatagcaaactgagcgtg |

-continued

| NUCLEOTIDE (NA) and AMINO ACID (AA) SEQUENCES |
| --- |

gataaaagccgctggcagcgcggcgatacctttatttgcgcggtgatgcatgaagcgctgcataaccatt atacccaggaaagcctgagccatagcccgggcaaa SEQ ID NO: 30:
Mouse-canine chimeric antibody 39A11 heavy chain AA sequence
EVKLVESGGGLVQPGGSLSLSCATSGFTESDYYMSWVRQSPGKALEWMGTIRNKANGYTTEYSASLKGRF

TISRDNSQSILYLQMNVLRAEDSATYYCVRFGLMYYFDYWGQGTTLTVSSASTTAPSVFPLAPSCGSTSG

STVALACLVSGYFPEPVTVSWNSGSLTSGVHTFPSVLQSSGLYSLSSMVTVPSSRWPSETFTCNVAHPAS

KTKVDKPVPKRENGRVPRPPDCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVNNKALPSPIERTISKARGQAH

QPSVYVLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPGK

SEQ ID NO: 31:
Mouse-canine chimeric antibody 45A9 heavy chain NA sequence
cagatccagttggtgcagtctggacctgagctgaagaagcctggagagacagtcaagatctcctgcaagg cttctgggtataccttcacaaactatggaatgaactgggtgaagcaggctccaggaaagggtttaaagtg gatgggctggataaacacctacactggagagccaacatatgctgatgacttcaagggacggtttgccttc tctttggaaacctctgccagcactgcctatttgcagatcaacaacctcaaaaatgaggacacggctacat atttctgtgcaagaagggggacctactataggccctggggccaaggcaccactctcacagtctcctcagc gagcaccaccgcgccgagcgtgtttccgctggcgccgagctgcggcagcaccagcggcagcaccgtggcg ctggcgtgcctggtgagcggctattttccggaaccggtgaccgtgagctggaacagcggcagcctgacca gcggcgtgcataccttttccgagcgtgctgcagagcagcggcctgtatagcctgagcagcatggtgaccgt gccgagcagccgctggccgagcgaaacctttacctgcaacgtggcgcatccggcgagcaaaaccaaagtg gataaaccggtgccgaaacgcgaaaacggccgcgtgccgcgcccgccggattgcccgaaatgcccggcgc cggaaatgctgggcggcccgagcgtgtttatttttccgccgaaaccgaaagataccctgctgattgcgcg caccccggaagtgacctgcgtggtggtggatctggatccggaagatccggaagtgcagattagctggttt gtggatggcaaacagatgcagaccgcgaaaacccagccgcgcgaagaacagtttaacggcacctatcgcg tggtgagcgtgctgccgattggccatcaggattggctgaaaggcaaacagtttacctgcaaagtgaacaa caaagcgctgccgagcccgattgaacgcaccattagcaaagcgcgcggccaggcgcatcagccgagcgtg tatgtgctgccgccgagccgcgaagaactgagcaaaaacaccgtgagcctgacctgcctgattaaagatt tttttccgccggatattgatgtggaatggcagagcaacggccagcaggaaccggaaagcaaatatcgcac caccccgccgcagctggatgaagatggcagctattttctgtatagcaaactgagcgtggataaaagccgc tggcagcgcggcgatacctttatttgcgcggtgatgcatgaagcgctgcataaccattatacccaggaaa gcctgagccatagcccgggcaaa SEQ ID NO: 32:
Mouse-canine chimeric antibody 45A9 heavy chain AA sequence
QIQLVQSGPELKKPGETVKISCKASGYTFTNYGMNWVKQAPGKGLKWMGWINTYTGEPTYADDFKGRFAF

SLETSASTAYLQINNLKNEDTATYFCARRGTYYRPPWGQGTTLTVSSASTTAPSVFPLAPSCGSTSGSTVA

LACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVDLDPEDPEVQISWF

VDGKQMQTAKTQPREEQFNGTYRVVSVLPIGHQDWLKGKQFTCKVNNKALPSPIERTISKARGQAHQPSV

-continued

| NUCLEOTIDE (NA) and AMINO ACID (AA) SEQUENCES |
|---|

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

SEQ ID NO: 33:
Mouse-canine chimeric antibody 110E3 heavy chain NA sequence
cagatccagttggtgcagtctggacctgagctgaagaagcctggagagacagtcaagatctcctgcaagg cttctggatataccttcacaaactatggaatgaactgggtgaagcaggctccaggaaagggtttaaagtg gatgggctggataaacacctacactggagagccaacatatgctgatgacttcaagggacgggttgccttc tctttggaaacctctgccagcactgcctttttgcagatcaacaacctcaaaaatgaggacacggctacat atttctgtgcaaggcgggggtacgactggactactggggccaaggcaccactctcacagtctcctcagc gagcaccaccgcgccgagcgtgtttccgctggcgccgagctgcggcagcaccagcggcagcaccgtggcg ctggcgtgcctggtgagcggctattttccggaaccggtgaccgtgagctggaacagcggcagcctgacca gcggcgtgcatacctttccgagcgtgctgcagagcagcggcctgtatagcctgagcagcatggtgaccgt gccgagcagccgctggccgagcgaaacctttacctgcaacgtggcgcatccggcgagcaaaaccaaagtg gataaaccggtgccgaaacgcgaaaacggccgcgtgccgcgcccgccggattgcccgaaatgcccggcgc cggaaatgctgggcggcccgagcgtgtttatttttccgccgaaaccgaaagataccctgctgattgcgcg caccccggaagtgacctgcgtggtggtggatctggatccggaagatccggaagtgcagattagctggttt gtggatggcaaacagatgcagaccgcgaaaacccagccgcgcgaagaacagtttaacggcacctatcgcg tggtgagcgtgctgccgattggccatcaggattggctgaaaggcaaacagtttacctgcaaagtgaacaa caaagcgctgccgagcccgattgaacgcaccattagcaaagcgcgcggccaggcgcatcagccgagcgtg tatgtgctgccgccgagccgcgaagaactgagcaaaaacaccgtgagcctgacctgcctgattaaagatt tttttccgccggatattgatgtggaatggcagagcaacggccagcaggaaccggaaagcaaatatcgcac caccccgccgcagctggatgaagatggcagctatttttctgtatagcaaactgagcgtggataaaagccgc tggcagcgcggcgatacctttatttgcgcggtgatgcatgaagcgctgcataaccattatacccaggaaa gcctgagccatagcccgggcaaa SEQ ID NO: 34:
Mouse-canine chimeric antibody 110E3 heavy chain AA sequence
QIQLVQSGPELKKPGETVKISCKASGYTFTNYGMNWVKQAPGKGLKWMGWINTYTGEPTYADDFKGRVAF

SLETSASTAFLQINNLKNEDTATYFCARRGVRLDYWGQGTTLTVSSASTTAPSVFPLAPSCGSTSGSTVA

LACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVDLDPEDPEVQISWF

VDGKQMQTAKTQPREEQFNGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

SEQ ID NO: 35:
Mouse-canine chimeric antibody 22A11 heavy chain NA sequence
caggtccaactgcagcagcctgggactgaactggtgaagcctggggcttcagtgaagctgtcctgcaagg cctctggctataccttcaccagctactggatgcactgggtgaagcagaggcctggacaaggccttgagtg gattggaaatatcaatcctagcaatggtggtactaggttcaatgagaagttcaagaacaaggccacactg actgaagacaaatcctccagcacagcctacatgcagctcagtagcctgacatctgaggactctgcggtct attattgtgcaagatcgaactacggtagtggctgggcctggtttgcttactggggccaagggactctggt cactgtctctgcagcgagcaccaccgcgccgagcgtgtttccgctggcgccgagctgcggcagcaccagc

-continued

| NUCLEOTIDE (NA) and AMINO ACID (AA) SEQUENCES |
| --- |

ggcagcaccgtggcgctggcgtgcctggtgagcggctattttccggaaccggtgaccgtgagctggaaca gcggcagcctgaccagcggcgtgcatacctttccgagcgtgctgcagagcagcggcctgtatagcctgag cagcatggtgaccgtgccgagcagccgctggccgagcgaaacctttacctgcaacgtggcgcatccggcg agcaaaaccaaagtggataaaccggtgccgaaacgcgaaaacggccgcgtgccgcgcccgccggattgcc cgaaatgcccggcgccggaaatgctgggcggcccgagcgtgtttattttttccgccgaaaccgaaagatac cctgctgattgcgcgcaccccggaagtgacctgcgtggtggtggatctggatccggaagatccggaagtg cagattagctggtttgtggatggcaaacagatgcagaccgcgaaaacccagccgcgcgaagaacagttta acggcacctatcgcgtggtgagcgtgctgccgattggccatcaggattggctgaaaggcaaacagtttac ctgcaaagtgaacaacaaagcgctgccgagcccgattgaacgcaccattagcaaagcgcgcggccaggcg catcagccgagcgtgtatgtgctgccgccgagccgcgaagaactgagcaaaaacaccgtgagcctgacct gcctgattaaagatttttttccgccggatattgatgtggaatggcagagcaacggccagcaggaaccgga aagcaaatatcgcaccaccccgccgcagctggatgaagatggcagctattttctgtatagcaaactgagc gtggataaaagccgctggcagcgcggcgatacctttatttgcgcggtgatgcatgaagcgctgcataacc attatacccaggaaagcctgagccatagcccgggcaaa SEQ ID NO: 36:
Mouse-canine chimeric antibody 22A11 heavy chain AA sequence
QVQLQQPGTELVKPGASVKLSCKASGYTFTSYWMHWVKQRPGQGLEWIGNINPSNGGTRFNEKFKNKATL

TEDKSSSTAYMQLSSLTSEDSAVYYCARSNYGSGWAWFAYWGQGTLVTVSAASTTAPSVFPLAPSCGSTS

GSTVALACLVSGYFPEPVTVSWNSGSLTSGVHTFPSVLQSSGLYSLSSMVTVPSSRWPSETFTCNVAHPA

SKTKVDKPVPKRENGRVPRPPDCPKCPAPEMLGGPSVFIFPPKPKDTLLIARTPEVTCVVVDLDPEDPEV

QISWFVDGKQMQTAKTQPREEQFNGTYRVVSVLPIGHQDWLKGKQFTCKVNNKALPSPIERTISKARGQA

HQPSVYVLPPSREELSKNTVSLTCLIKDFFPPDIDVEWQSNGQQEPESKYRTTPPQLDEDGSYFLYSKLS

VDKSRWQRGDTFICAVMHEALHNHYTQESLSHSPGK

SEQ ID NO: 37:
Mouse-canine chimeric antibody 12B3 light chain NA sequence
gatgttttgatgacccaaactccactctccctgcctgtcagtcttggagatcaagcctccatctcttgca gatctagtcagagcattgtatatagtaatggaaacacctatttagaatggtacctgcagaaaccaggcca gtctccaaagctcctgatctacaaagtttccaaccgattttctggggtcccagacaggttcagtggcagt ggatcagggacagatttcacactcaagatcagcagagtggaggctgaggatctgggagtttattactgct ttcaaggttcacatgttccgtggacgttcggtggaggcaccaagctggaaatcaaacgcaacgatgcgca gccggcggtgtatctgtttcagccgagcccggatcagctgcataccggcagcgcgagcgtggtgtgcctg ctgaacagcttttatccgaaagatattaacgtgaaatggaaagtggatggcgtgattcaggataccggca ttcaggaaagcgtgaccgaacaggatagcaaagatagcacctatagcctgagcagcaccctgaccatgag cagcaccgaatatctgagccatgaactgtatagctgcgaaattacccataaaagcctgccgagcaccctg attaaaagctttcagcgcagcgaatgccagcgcgtggat SEQ ID NO: 38:
Mouse-canine chimeric antibody 12B3 light chain AA sequence
DVLMTQTPLSLPVSLGDQASISCRSSQSIVYSNGNTYLEWYLQKPGQSPKLLIYKVSNRFSGVPDRFSGS

GSGTDFTLKISRVEAEDLGVYYCFQGSHVPWTFGGGTKLEIKRNDAQPAVYLFQPSPDQLHTGSASVVCL

LNSFYPKDINVKWKVDGVIQDTGIQESVTEQDSKDSTYSLSSTLTMSSTEYLSHELYSCEITHKSLPSTL

IKSFQRSECQRVD

-continued

| NUCLEOTIDE (NA) and AMINO ACID (AA) SEQUENCES |
|---|

SEQ ID NO: 39:
Mouse-canine chimeric antibody 27G12 light chain NA sequence
gatgttttgatgacccagactccactctccctgcctgtcagtcttggagatcacgcctccatctcttgca aatctagtcagagcattgtatatattaatggaaacacctatttagaatggtacctgcagaagccaggcca gtctccaaagctcctgatctacaaagtttccaaacgattttctggggtcccagacaggttcagtggcagt ggatcagggacagatttcacactcaagatcagcagagtggaggctgaggatctgggagtttattactgct ttcaaggttcacatgttccgtggacgttcggtggaggcaccaagctggaaatcaaacgcaacgatgcgca gccggcggtgtatctgtttcagccgagcccggatcagctgcataccggcagcgcgagcgtggtgtgcctg ctgaacagcttttatccgaaagatattaacgtgaaatggaaagtggatggcgtgattcaggataccggca ttcaggaaagcgtgaccgaacaggatagcaaagatagcacctatagcctgagcagcaccctgaccatgag cagcaccgaatatctgagccatgaactgtatagctgcgaaattacccataaaagcctgccgagcaccctg attaaaagctttcagcgcagcgaatgccagcgcgtggat SEQ ID NO: 40:
Mouse-canine chimeric antibody 27G12 light chain AA sequence
DVLMTQTPLSLPVSLGDHASISCKSSQSIVYINGNTYLEWYLQKPGQSPKLLIYKVSKRFSGVPDRFSGS

GSGTDFTLKISRVEAEDLGVYYCFQGSHVPWTFGGGTKLEIKRNDAQPAVYLFQPSPDQLHTGSASVVCL

LNSFYPKDINVKWKVDGVIQDTGIQESVTEQDSKDSTYSLSSTLTMSSTEYLSHELYSCEITHKSLPSTL

IKSFQRSECQRVD

SEQ ID NO: 41:
Mouse-canine chimeric antibody 39A11 light chain NA sequence
gaaaatgtgctcatccagtctccagcaatcatgtctgcttctccaggggaaaaggtcaccatgacctgca gggccagctcaagtgtaagttccagttacttgcactggtaccagcagaagtcaggtgcctcccccaaact ctggatttttagcacatccaacttggcttctggagtccctgctcgcttcagtggcagtgggtctgggacc tcttattctctcacaatcaacagtgtggaggctgaagatgctgccacttattactgccagcagtacagtg gtctcccactcacgttcggaggggggaccaagctggaaataaaacgcaacgatgcgcagccggcggtgta tctgtttcagccgagcccggatcagctgcataccggcagcgcgagcgtggtgtgcctgctgaacagcttt tatccgaaagatattaacgtgaaatggaaagtggatggcgtgattcaggataccggcattcaggaaagcg tgaccgaacaggatagcaaagatagcacctatagcctgagcagcaccctgaccatgagcagcaccgaata tctgagccatgaactgtatagctgcgaaattacccataaaagcctgccgagcaccctgattaaaagcttt cagcgcagcgaatgccagcgcgtggat SEQ ID NO: 42:
Mouse-canine chimeric antibody 39A11 light chain AA sequence
ENVLIQSPAIMSASPGEKVTMTCRASSSVSSSYLHWYQQKSGASPKLWIFSTSNLASGVPARFSGSGSGT

SYSLTINSVEAEDAATYYCQQYSGLPLTFGGGTKLEIKRNDAQPAVYLFQPSPDQLHTGSASVVCLLNSF

YPKDINVKWKVDGVIQDTGIQESVTEQDSKDSTYSLSSTLTMSSTEYLSHELYSCEITHKSLPSTLIKSF

QRSECQRVD

SEQ ID NO: 43:
Mouse-canine chimeric antibody 45A9 light chain NA sequence
gatgttttgatgacccaaactccactctccctgcctgtcagtcttggagatcaagcctccatctcttgca gatctagtcagagtattgtatatagtcatggaaacacctatttagaatggtacctgcagaaaccaggcca gtctccaaaggtcctgatctacaaagtttccaaccgattttctggggtcccagacaggttcagtggcagt ggatcagggacagatttcacactcaagatcagcagagtggaggctgaggatctgggagtttattactgct ttcaaggttcacatgttccgtggacgttcggtggaggcaccaagctggaaatcaaacgcaacgatgcgca

-continued

NUCLEOTIDE (NA) and AMINO ACID (AA) SEQUENCES gccggcggtgtatctgtttcagccgagcccggatcagctgcataccggcagcgcgagcgtggtgtgcctg ctgaacagcttttatccgaaagatattaacgtgaaatggaaagtggatggcgtgattcaggataccggca ttcaggaaagcgtgaccgaacaggatagcaaagatagcacctatagcctgagcagcaccctgaccatgag cagcaccgaatatctgagccatgaactgtatagctgcgaaattacccataaaagcctgccgagcaccctg attaaaagctttcagcgcagcgaatgccagcgcgtggat SEQ ID NO: 44:
Mouse-canine chimeric antibody 45A9 light chain AA sequence
DVLMTQTPLSLPVSLGDQASISCRSSQSIVYSHGNTYLEWYLQKPGQSPKVLIYKVSNRFSGVPDRFSGS

GSGTDFTLKISRVEAEDLGVYYCFQGSHVPWTFGGGTKLEIKRNDAQPAVYLFQPSPDQLHTGSASVVCL

LNSFYPKDINVKWKVDGVIQDTGIQESVTEQDSKDSTYSLSSTLTMSSTEYLSHELYSCEITHKSLPSTL

IKSFQRSECQRVD

SEQ ID NO: 45:
Mouse-canine chimeric antibody 110E3 light chain NA sequence
gatgttttgatgacccaaactccactctccctgcctgtcagtcttggagatcaagcctccatctcttgca gatctagtcagagcattgtatatattagtggaagcacctatttagaatggtatctgcagaaaccaggcca gtctccaaagctcctgatctacaaagtttccagtcgattttctggggtcccagacaggttcagtggcagt ggatcagggacagatttcacactcaagatcagcagagtggaggctgaggatctgggagtttattactgct ttcaaggttcacatgttccgtggacgttcggtggaggcaccaagctggaaatcaaacgcaacgatgcgca gccggcggtgtatctgtttcagccgagcccggatcagctgcataccggcagcgcgagcgtggtgtgcctg ctgaacagcttttatccgaaagatattaacgtgaaatggaaagtggatggcgtgattcaggataccggca ttcaggaaagcgtgaccgaacaggatagcaaagatagcacctatagcctgagcagcaccctgaccatgag cagcaccgaatatctgagccatgaactgtatagctgcgaaattacccataaaagcctgccgagcaccctg attaaaagctttcagcgcagcgaatgccagcgcgtggat SEQ ID NO: 46:
Mouse-canine chimeric antibody 110E3 light chain AA sequence
DVLMTQTPLSLPVSLGDQASISCRSSQSIVYISGSTYLEWYLQKPGQSPKLLIYKVSSRFSGVPDRFSGS

GSGTDFTLKISRVEAEDLGVYYCFQGSHVPWTFGGGTKLEIKRNDAQPAVYLFQPSPDQLHTGSASVVCL

LNSFYPKDINVKWKVDGVIQDTGIQESVTEQDSKDSTYSLSSTLTMSSTEYLSHELYSCEITHKSLPSTL

IKSFQRSECQRVD

SEQ ID NO: 47:
Mouse-canine chimeric monoclonal antibody 22A11 light chain NA sequence
gacatccagatgaaccagtctccatccagtctgtctgcatcccttggagacacaattaccatcacttgcc atgccagtcagaacattaatgtttggttaagctggtaccagcagaaaccaggaaatattcctaaactttt gatctataagtcttccaacttgcacacaggcgtcccatcaaggtttagtggcagtggatctggaacaggt ttcacattaaccatcagcagcctgcagcctgaagacattgccacttactactgtcaacagggtcaaagtt atccgtggacgttcggtggaggcaccaagctggaaatcaaacgcaacgatgcgcagccggcggtgtatct gtttcagccgagcccggatcagctgcataccggcagcgcgagcgtggtgtgcctgctgaacagcttttat ccgaaagatattaacgtgaaatggaaagtggatggcgtgattcaggataccggcattcaggaaagcgtga ccgaacaggatagcaaagatagcacctatagcctgagcagcaccctgaccatgagcagcaccgaatatct gagccatgaactgtatagctgcgaaattacccataaaagcctgccgagcaccctgattaaaagctttcag cgcagcgaatgccagcgcgtggat -continued NUCLEOTIDE (NA) and AMINO ACID (AA) SEQUENCES SEQ ID NO: 48:
Mouse-canine chimeric antibody 22A11 light chain AA sequence
DIQMNQSPSSLSASLGDTITITCHASQNINVWLSWYQQKPGNIPKLLIYKSSNLHTGVPSRFSGSGSGTG

FTLTISSLQPEDIATYYCQQGQSYPWTFGGGTKLEIKRNDAQPAVYLFQPSPDQLHTGSASVVCLLNSFY

PKDINVKWKVDGVIQDTGIQESVTEQDSKDSTYSLSSTLTMSSTEYLSHELYSCEITHKSLPSTLIKSFQ

RSECQRVD

SEQ ID NO: 49:
Caninized 12B3 light chain NA sequence (VL1)
gatattgtgatgacccagaccccgctgagcctgagcgtgagcccgggcgaaccggcgagcattagctgcc gcagcagccagagcattgtgtatagcaacggcaacacctatctggaatggtttcagcagaaaccgggcca gagcccgcagcgcctgatttataaagtgagcaaccgctttagcggcgtgccggatcgctttagcggcagc ggcagcggcaccgattttaccctgcgcattagccgcgtggaagcggatgatgcgggcgtgtattattgct ttcagggcagccatgtgccgtggacctttggcggcggcaccaaactggaaattaaaaggaacgacgctca gccagccgtgtacctcttccagccttcgccggaccagcttcatacggggtcagcgtcggtggtgtgcctg ttgaactcgttttaccccaaggacattaacgtgaagtggaaggtagacggggtaattcaagacactggca ttcaagagtccgtcacggaacaagactcaaaagactcaacgtattcactgtcgtcaaccttgacgatgtc aagcaccgagtatcttagccatgagctgtattcgtgcgagatcacccacaagtccctcccctccactctt atcaaatcctttcagcggtcggaatgtcagcgggtcgat SEQ ID NO: 50:
Caninized 12B3 light chain AA sequence (VL1)
DIVMTQTPLSLSVSPGEPASISCRSSQSIVYSNGNTYLEWFQQKPGQSPQRLIYKVSNRFSGVPDRFSGS

GSGTDFTLRISRVEADDAGVYYCFQGSHVPWTFGGGTKLEIKRNDAQPAVYLFQPSPDQLHTGSASVVCL

LNSFYPKDINVKWKVDGVIQDTGIQESVTEQDSKDSTYSLSSTLTMSSTEYLSHELYSCEITHKSLPSTL

IKSFQRSECQRVD

SEQ ID NO: 51:
Caninized 12B3 light chain NA sequence (VL2)
gatattgtgatgacccagaccccgctgagcctgagcgtgagcccgggcgaaccggcgagcattagctgcc gcagcagccagagcattgtgtatagcaacggcaacacctatctggaatggtatcagcagaaaccgggcca gagcccgaaactgctgatttataaagtgagcaaccgctttagcggcgtgccggatcgctttagcggcagc ggcagcggcaccgattttaccctgcgcattagccgcgtggaagcggatgatgcgggcgtgtattattgct ttcagggcagccatgtgccgtggacctttggcggcggcaccaaactggaaattaaaaggaacgacgctca gccagccgtgtacctcttccagccttcgccggaccagcttcatacggggtcagcgtcggtggtgtgcctg ttgaactcgttttaccccaaggacattaacgtgaagtggaaggtagacggggtaattcaagacactggca ttcaagagtccgtcacggaacaagactcaaaagactcaacgtattcactgtcgtcaaccttgacgatgtc aagcaccgagtatcttagccatgagctgtattcgtgcgagatcacccacaagtccctcccctccactctt atcaaatcctttcagcggtcggaatgtcagcgggtcgat SEQ ID NO: 52:
Caninized 12B3 light chain AA sequence (VL2)
DIVMTQTPLSLSVSPGEPASISCRSSQSIVYSNGNTYLEWYQQKPGQSPKLLIYKVSNRFSGVPDRFSGS

GSGTDFTLRISRVEADDAGVYYCFQGSHVPWTFGGGTKLEIKRNDAQPAVYLFQPSPDQLHTGSASVVCL

LNSFYPKDINVKWKVDGVIQDTGIQESVTEQDSKDSTYSLSSTLTMSSTEYLSHELYSCEITHKSLPSTL

IKSFQRSECQRVD

-continued

| NUCLEOTIDE (NA) and AMINO ACID (AA) SEQUENCES |
| --- |

SEQ ID NO: 53:
Caninized 12B3 light chain NA sequence (VL3)
gatgtgctgatgacccagaccccgctgagcctgagcgtgagcccgggcgaaccggcgagcattagctgcc gcagcagccagagcattgtgtatagcaacggcaacacctatctggaatggtatctgcagaaaccgggcca gagcccgaaactgctgatttataaagtgagcaaccgctttagcggcgtgccggatcgctttagcggcagc ggcagcggcaccgattttaccctgcgcattagccgcgtggaagcggatgatgcgggcgtgtattattgct ttcagggcagccatgtgccgtggacctttggcggcggcaccaaactggaactgaaaaggaacgacgctca gccagccgtgtacctcttccagccttcgccggaccagcttcatacggggtcagcgtcggtggtgtgcctg ttgaactcgttttaccccaaggacattaacgtgaagtggaaggtagacggggtaattcaagacactggca ttcaagagtccgtcacggaacaagactcaaaagactcaacgtattcactgtcgtcaaccttgacgatgtc aagcaccgagtatcttagccatgagctgtattcgtgcgagatcacccacaagtccctcccctccactctt atcaaatcctttcagcggtcggaatgtcagcgggtcgat SEQ ID NO: 54:
Caninized 12B3 light chain AA sequence (VL3)
DVLMTQTPLSLSVSPGEPASISCRSSQSIVYSNGNTYLEWYLQKPGQSPKLLIYKVSNRFSGVPDRFSGS

GSGTDFTLRISRVEADDAGVYYCFQGSHVPWTFGGGTKLELKRNDAQPAVYLFQPSPDQLHTGSASVVCL

LNSFYPKDINVKWKVDGVIQDTGIQESVTEQDSKDSTYSLSSTLTMSSTEYLSHELYSCEITHKSLPSTL

IKSFQRSECQRVD

SEQ ID NO: 55:
Caninized 39A11 light chain NA sequence (VL1)
gaaattgtgatgacccagagcccggcgagcctgagcctgagccaggaagaaaaagtgaccattacctgcc gcgcgagcagcagcgtgagcagcagctatctgcattggtatcagcagaaaccgggccaggcgccgaaact gctgatttatagcaccagcaacctggcgagcggcgtgccgagccgctttagcggcagcggcagcggcacc gattttagctttaccattagcagcctggaaccggaagatgtggcggtgtattattgccagcagtatagcg gcctgccgctgacctttggcggcggcaccaaactggaaattaaaaggaacgacgctcagccagccgtgta cctcttccagccttcgccggaccagcttcatacggggtcagcgtcggtggtgtgcctgttgaactcgttt taccccaaggacattaacgtgaagtggaaggtagacggggtaattcaagacactggcattcaagagtccg tcacggaacaagactcaaaagactcaacgtattcactgtcgtcaaccttgacgatgtcaagcaccgagta tcttagccatgagctgtattcgtgcgagatcacccacaagtccctcccctccactcttatcaaatccttt cagcggtcggaatgtcagcgggtcgat SEQ ID NO: 56:
Caninized 39A11 light chain AA sequence (VL1)
EIVMTQSPASLSLSQEEKVTITCRASSSVSSSYLHWYQQKPGQAPKLLIYSTSNLASGVPSRFSGSGSGT

DFSETISSLEPEDVAVYYCQQYSGLPLTFGGGTKLEIKRNDAQPAVYLFQPSPDQLHTGSASVVCLLNSF

YPKDINVKWKVDGVIQDTGIQESVTEQDSKDSTYSLSSTLTMSSTEYLSHELYSCEITHKSLPSTLIKSF

QRSECQRVD

SEQ ID NO: 57:
Caninized 39A11 light chain NA sequence (VL2)
gaaaacgtgctgacccagagcccggcgagcctgagcctgagccaggaagaaaaagtgaccattacctgcc gcgcgagcagcagcgtgagcagcagctatctgcattggtatcagcagaaaccgggccaggcgccgaaact gtggatttttagcaccagcaacctggcgagcggcgtgccgagccgctttagcggcagcggcagcggcacc gattatagctttaccattagcagcctggaaccggaagatgtggcggtgtattattgccagcagtatagcg gcctgccgctgacctttggcggcggcaccaaactggaactgaaaaggaacgacgctcagccagccgtgta

-continued

| NUCLEOTIDE (NA) and AMINO ACID (AA) SEQUENCES |
|---|
| cctcttccagccttcgccggaccagcttcatacggggtcagcgtcggtggtgtgcctgttgaactcgttt |
| taccccaaggacattaacgtgaagtggaaggtagacggggtaattcaagacactggcattcaagagtccg |
| tcacggaacaagactcaaaagactcaacgtattcactgtcgtcaaccttgacgatgtcaagcaccgagta |
| tcttagccatgagctgtattcgtgcgagatcacccacaagtccctcccctccactcttatcaaatccttt |
| cagcggtcggaatgtcagcgggtcgat |
| SEQ ID NO: 58:<br>Caninized 39A11 light chain AA sequence (VL2)<br>**ENVLTQSPASLSLSQEEKVTITC<u>RASSSVSSSYLH</u>WYQQKPGQAPKLWIF<u>STSNLAS</u>GVPSRFSGSGSGT** |
| **DYSETISSLEPEDVAVYYC<u>QQYSGLPLT</u>FGGGTKLELK**RNDAQPAVYLFQPSPDQLHTGSASVVCLLNSF |
| YPKDINVKWKVDGVIQDTGIQESVTEQDSKDSTYSLSSTLTMSSTEYLSHELYSCEITHKSLPSTLIKSF |
| QRSECQRVD |
| SEQ ID NO: 59:<br>Caninized 39A11 light chain NA sequence (VL3)<br>**gaaaacgtgctgacccagagcccggcgagcctgagcctgagcccgggcgaaaaagtgaccattacctgcc** |
| **gcgcgagcagcagcgtgagcagcagctatctgcattggtatcagcagaaaccgggccagagcccgaaact** |
| **gtggatttttagcaccagcaacctggcgagcggcgtgccgagccgctttagcggcagcggcagcggcacc** |
| **agctatagctttaccattagcagcctggaaccggaagatgtggcggtgtattattgccagcagtatagcg** |
| **gcctgccgctgacctttggcggcggcaccaaactggaactgaaaaggaa**cgacgctcagccagccgtgta |
| cctcttccagccttcgccggaccagcttcatacggggtcagcgtcggtggtgtgcctgttgaactcgttt |
| taccccaaggacattaacgtgaagtggaaggtagacggggtaattcaagacactggcattcaagagtccg |
| tcacggaacaagactcaaaagactcaacgtattcactgtcgtcaaccttgacgatgtcaagcaccgagta |
| tcttagccatgagctgtattcgtgcgagatcacccacaagtccctcccctccactcttatcaaatccttt |
| cagcggtcggaatgtcagcgggtcgat |
| SEQ ID NO: 60:<br>Caninized 39A11 light chain AA sequence (VL3)<br>**ENVLTQSPASLSLSPGEKVTITC<u>RASSSVSSSYLH</u>WYQQKPGQSPKLWIF<u>STSNLAS</u>GVPSRFSGSGSGT** |
| **SYSETISSLEPEDVAVYYC<u>QQYSGLPLT</u>FGGGTKLELK**RNDAQPAVYLFQPSPDQLHTGSASVVCLLNSF |
| YPKDINVKWKVDGVIQDTGIQESVTEQDSKDSTYSLSSTLTMSSTEYLSHELYSCEITHKSLPSTLIKSF |
| QRSECQRVD |
| SEQ ID NO: 61:<br>Caninized 12B3 heavy chain NA sequence (VH1) with IgGB<br>**gaagtgcagctggtggaaagcggcggcgatctggtgaaaccgggcggcagcctgcgcctgagctgcgtgg** |
| **cgagcggctatacctttaccaactatggcatgaactgggtgcgccaggcgccgggcaaaggcctgcagtg** |
| **ggtggcgtggattaacacctataccggcgaaccgacctatgcggatgattttaaaggccgctttaccatt** |
| **agccgcgataacgcgaaaaacaccctgtatctgcagatgaacagcctgcgcgcggaagataccgcggtgt** |
| **attattgcgcgcgcgcgcagcatttattatccgtattggggccagggcaccaccctgaccgtgagcagc**gc |
| ttccacaaccgcgccatcagtctttccgttggccccatcatgcgggtcgacgagcggatcgactgtggcc |
| ctggcgtgcttggtgtcgggatactttcccgaacccgtcacggtcagctggaactccggatcgcttacga |
| gcggtgtgcatacgttcccctcggtcttgcaatcatcagggctctactcgctgtcgagcatggtaacggt |
| gccctcatcgaggtggccctccgaaacgttcacatgtaacgtagcacatccagcctccaaaaccaaggtg |
| gataaacccgtgccgaaaagagagaatgggcgggtgcctcgacccccctgattgccccaagtgtccggctc |
| cggaaatgctcggtggaccctcagtgtttatcttccctccgaagcccaaggacactctgctgatcgcgcg |
| cactccagaagtaacatgtgtagtggtggaccttgatcccgaggaccccgaagtccagatctcctggttt |

-continued

| NUCLEOTIDE (NA) and AMINO ACID (AA) SEQUENCES |
|---|
| gtagatgggaaacagatgcagaccgcaaaaactcaacccagagaggagcagttcaacggaacataccgag |
| tggtatccgtccttccgattggccaccaggactggttgaaagggaagcagtttacgtgtaaagtcaacaa |
| taaggggttgcctagccctattgagcggacgatttcgaaagctaggggacaggcccaccagccatcggtc |
| tatgtccttccgccttcccgcgaggagctctcgaagaatacagtgagccttacatgcctcattaaggatt |
| tcttcccgcctgatatcgacgtagagtggcaatcaaacggtcaacaggagccggaatccaagtatagaac |
| cactccgccccagcttgacgaggacggatcatactttttgtattcaaaactgtcggtggataagagccgg |
| tggcagagaggtgacaccttcatctgtgcggtgatgcacgaagcactccataatcactacacccaagaga |
| gcctctcgcattcccccggaaag |
| SEQ ID NO: 62:<br>Caninized 12B3 heavy chain AA sequence (VH1) with IgGB<br>**EVQLVESGGDLVKPGGSLRLSCVASGYTFTNYGMNWVRQAPGKGLQWVAWINTYTGEPTYADDFKGRFTI** |
| **SRDNAKNTLYLQMNSLRAEDTAVYYCARRSIYYPYWGQGTTLTVSS**ASTTAPSVFPLAPSCGSTSGSTVA |
| LACLVSGYFPEPVTVSWNSGSLTSGVHTFPSVLQSSGLYSLSSMVTVPSSRWPSETFTCNVAHPASKTKV |
| DKPVPKRENGRVPRPPDCPKCPAPEMLGGPSVFIFPPKPKDTLLIARTPEVTCVVVDLDPEDPEVQISWF |
| VDGKQMQTAKTQPREEQFNGTYRVVSVLPIGHQDWLKGKQFTCKVNNKALPSPIERTISKARGQAHQPSV |
| YVLPPSREELSKNTVSLTCLIKDFFPPDIDVEWQSNGQQEPESKYRTTPPQLDEDGSYFLYSKLSVDKSR |
| WQRGDTFICAVMHEALHNHYTQESLSHSPGK |
| SEQ ID NO: 63:<br>Caninized 12B3 heavy chain NA sequence (VH2) with IgGB<br>**gaaattcagctggtgcagagcggcggcgatctggtgaaaccgggcggcagcctgcgcctgagctgcaaag** |
| **cgagcggctatacctttaccaactatggcatgaactgggtgcgccaggcgccgggcaaaggcctgcagtg** |
| **gatgggctggattaacacctataccggcgaaccgacctatgcggatgattttaaaggccgctttaccttt** |
| **agcctggataacgcgaaaaacaccctgtatctgcagatgaacagcctgcgcgcggaagataccgcggtgt** |
| **atttttgcgcgcgccgcagcatttattatccgtattggggccagggcaccaccctgaccgtgagcagc**gc |
| ttccacaaccgcgccatcagtctttccgttggccccatcatgcgggtcgacgagcggatcgactgtggcc |
| ctggcgtgcttggtgtcgggatactttcccgaacccgtcacggtcagctggaactccggatcgcttacga |
| gcggtgtgcatacgttcccctcggtcttgcaatcatcagggctctactcgctgtcgagcatggtaacggt |
| gccctcatcgaggtggccctccgaaacgttcacatgtaacgtagcacatccagcctccaaaaccaaggtg |
| gataaacccgtgccgaaaagagagaatgggcgggtgcctcgacccccctgattgccccaagtgtccggctc |
| cggaaatgctcggtggaccctcagtgtttatcttccctccgaagcccaaggacactctgctgatcgcgcg |
| cactccagaagtaacatgtgtagtggtggaccttgatcccgaggaccccgaagtccagatctcctggttt |
| gtagatgggaaacagatgcagaccgcaaaaactcaacccagagaggagcagttcaacggaacataccgag |
| tggtatccgtccttccgattggccaccaggactggttgaaagggaagcagtttacgtgtaaagtcaacaa |
| taaggggttgcctagccctattgagcggacgatttcgaaagctaggggacaggcccaccagccatcggtc |
| tatgtccttccgccttcccgcgaggagctctcgaagaatacagtgagccttacatgcctcattaaggatt |
| tcttcccgcctgatatcgacgtagagtggcaatcaaacggtcaacaggagccggaatccaagtatagaac |
| cactccgccccagcttgacgaggacggatcatactttttgtattcaaaactgtcggtggataagagccgg |
| tggcagagaggtgacaccttcatctgtgcggtgatgcacgaagcactccataatcactacacccaagaga |
| gcctctcgcattcccccggaaag |

-continued

NUCLEOTIDE (NA) and AMINO ACID (AA) SEQUENCES

SEQ ID NO: 64:
Caninized 12B3 heavy chain AA sequence (VH2) with IgGB
ETQLVQSGGDLVKPGGSLRLSCKASGYTFTNYGMNWVRQAPGKGLQWMGWINTYTGEPTYADDFKGRFTF

SLDNAKNTLYLQMNSLRAEDTAVYFCARRSIYYPYWGQGTTLTVSSASTTAPSVFPLAPSCGSTSGSTVA

LACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVDLDPEDPEVQISWF

VDGKQMQTAKTQPREEQFNGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

SEQ ID NO: 65:
Caninized 12B3 heavy chain NA sequence (VH3) with IgGB
gaaattcagctggtgcagagcggcggcgatctggtgaaaccgggcggcagcgtgcgcctgagctgcaaag cgagcggctatacctttaccaactatggcatgaactgggtgaaacaggcgccgggcaaaggcctgcagtg gatgggctggattaacacctataccggcgaaccgacctatgcggatgattttaaaggccgctttaccttt agcctggataacgcgaaaaacaccgcgtatctgcagattaacagcctgcgcgcggaagataccgcggtgt atttttgcgcgcgccgcagcatttattatccgtattggggccagggcaccaccctgaccgtgagcagcgc ttccacaaccgcgccatcagtctttccgttggccccatcatgcgggtcgacgagcggatcgactgtggcc ctggcgtgcttggtgtcgggatactttcccgaacccgtcacggtcagctggaactccggatcgcttacga gcggtgtgcatacgttcccctcggtcttgcaatcatcagggctctactcgctgtcgagcatggtaacggt gccctcatcgaggtggccctccgaaacgttcacatgtaacgtagcacatccagcctccaaaaccaaggtg gataaacccgtgccgaaaagagagaatgggcgggtgcctcgacccccctgattgccccaagtgtccggctc cggaaatgctcggtggaccctcagtgtttatcttccctccgaagcccaaggacactctgctgatcgcgcg cactccagaagtaacatgtgtagtggtggaccttgatcccgaggaccccgaagtccagatctcctggttt gtagatgggaaacagatgcagaccgcaaaaactcaacccagagaggagcagttcaacggaacataccgag tggtatccgtccttccgattggccaccaggactggttgaaagggaagcagtttacgtgtaaagtcaacaa taaggggttgcctagccctattgagcggacgatttcgaaagctaggggacaggcccaccagccatcggtc tatgtccttccgccttcccgcgaggagctctcgaagaatacagtgagccttacatgcctcattaaggatt tcttcccgcctgatatcgacgtagagtggcaatcaaacggtcaacaggagccggaatccaagtatagaac cactccgccccagcttgacgaggacggatcatactttttgtattcaaaactgtcggtggataagagccgg tggcagagaggtgacaccttcatctgtgcggtgatgcacgaagcactccataatcactacacccaagaga gcctctcgcattcccccggaaag SEQ ID NO: 66:
Caninized 12B3 heavy chain AA sequence (VH3) with IgGB
EIQLVQSGGDLVKPGGSVRLSCKASGYTFTNYGMNWVKQAPGKGLQWMGWINTYTGEPTYADDFKGRFTF

SLDNAKNTAYLQINSLRAEDTAVYFCARRSIYYPYWGQGTTLTVSSASTTAPSVFPLAPSCGSTSGSTVA

LACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVDLDPEDPEVQISWF

VDGKQMQTAKTQPREEQFNGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

-continued

| NUCLEOTIDE (NA) and AMINO ACID (AA) SEQUENCES |
|---|

SEQ ID NO: 67:
Caninized 39A11 heavy chain NA sequence (VH1) with IgGB
gaagtgcagctggtggaaagcggcggcgatctggtgaaaccgggcggcagcctgcgcctgagctgcgtgg cgagcggctttacctttagcgattattatatgagctgggtgcgccaggcgccgggcaaaggcctggaatg ggtggcgtttattcgcaacaaagcgaacggctataccaccgaatatagcgcgagcctgaaaggccgcttt accattagccgcgataacgcgaaaaacatggcgtatctgcagatgaacagcctgcgcgcggaagataccg cggtgtattattgcgcgagctttggcctgatgtattattttgattattggggccagggcaccaccctgac cgtgagcagcgcttccacaaccgcgccatcagtctttccgttggccccatcatgcgggtcgacgagcgga tcgactgtggccctggcgtgcttggtgtcgggatactttcccgaacccgtcacggtcagctggaactccg gatcgcttacgagcggtgtgcatacgttcccctcggtcttgcaatcatcagggctctactcgctgtcgag catggtaacggtgccctcatcgaggtggccctccgaaacgttcacatgtaacgtagcacatccagcctcc aaaaccaaggtggataaacccgtgccgaaaagagagaatgggcgggtgcctcgacccccctgattgcccca agtgtccggctccggaaatgctcggtggaccctcagtgtttatcttccctccgaagcccaaggacactct gctgatcgcgcgcactccagaagtaacatgtgtagtggtggaccttgatcccgaggaccccgaagtccag atctcctggtttgtagatgggaaacagatgcagaccgcaaaaactcaacccagagaggagcagttcaacg gaacataccgagtggtatccgtccttccgattggccaccaggactggttgaaagggaagcagtttacgtg taaagtcaacaataaggggttgcctagccctattgagcggacgatttcgaaagctaggggacaggcccac cagccatcggtctatgtccttccgccttcccgcgaggagctctcgaagaatacagtgagccttacatgcc tcattaaggatttcttcccgcctgatatcgacgtagagtggcaatcaaacggtcaacaggagccggaatc caagtatagaaccactccgccccagcttgacgaggacggatcatactttttgtattcaaaactgtcggtg gataagagccggtggcagagaggtgacaccttcatctgtgcggtgatgcacgaagcactccataatcact acacccaagagagcctctcgcattcccccggaaag SEQ ID NO: 68:
Caninized 39A11 heavy chain AA sequence (VH1) with IgGB
EVQLVESGGDLVKPGGSLRLSCVASGETFSDYYMSWVRQAPGKGLEWVAFIRNKANGYTTEYSASLKGRF

TISRDNAKNMAYLQMNSLRAEDTAVYYCASFGLMYYFDYWGQGTTLTVSSASTTAPSVFPLAPSCGSTSG

STVALACLVSGYFPEPVTVSWNSGSLTSGVHTFPSVLQSSGLYSLSSMVTVPSSRWPSETFTCNVAHPAS

KTKVDKPVPKRENGRVPRPPDCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVNNKALPSPIERTISKARGQAH

QPSVYVLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPGK

SEQ ID NO: 69:
Caninized 39A11 heavy chain NA sequence (VH2) with IgGB
gaagtgcagctggtggaaagcggcggcgatctggtgaaaccgggcggcagcctgcgcctgagctgcgcga ccagcggctttacctttagcgattattatatgagctgggtgcgccaggcgccgggcaaaggcctggaatg gatgggctttattcgcaacaaagcgaacggctataccaccgaatatagcgcgagcctgaaaggccgcttt accattagccgcgataacgcgaaaaacatggcgtatctgcagatgaacagcctgcgcgcggaagataccg cggtgtattattgcgtgcgctttggcctgatgtattattttgattattggggccagggcaccaccctgac cgtgagcagcgcttccacaaccgcgccatcagtctttccgttggccccatcatgcgggtcgacgagcgga tcgactgtggccctggcgtgcttggtgtcgggatactttcccgaacccgtcacggtcagctggaactccg gatcgcttacgagcggtgtgcatacgttcccctcggtcttgcaatcatcagggctctactcgctgtcgag -continued

| NUCLEOTIDE (NA) and AMINO ACID (AA) SEQUENCES |
|---|

catggtaacggtgccctcatcgaggtggccctccgaaacgttcacatgtaacgtagcacatccagcctcc aaaaccaaggtggataaacccgtgccgaaaagagagaatgggcgggtgcctcgacccccctgattgcccca agtgtccggctccggaaatgctcggtggaccctcagtgtttatcttccctccgaagcccaaggacactct gctgatcgcgcgcactccagaagtaacatgtgtagtggtggaccttgatcccgaggaccccgaagtccag atctcctggtttgtagatgggaaacagatgcagaccgcaaaaactcaacccagagaggagcagttcaacg gaacataccgagtggtatccgtccttccgattggccaccaggactggttgaaagggaagcagtttacgtg taaagtcaacaataaggggttgcctagccctattgagcggacgatttcgaaagctaggggacaggcccac cagccatcggtctatgtccttccgccttcccgcgaggagctctcgaagaatacagtgagccttacatgcc tcattaaggatttcttcccgcctgatatcgacgtagagtggcaatcaaacggtcaacaggagccggaatc caagtatagaaccactccgccccagcttgacgaggacggatcatacttttttgtattcaaaactgtcggtg gataagagccggtggcagagaggtgacaccttcatctgtgcggtgatgcacgaagcactccataatcact acacccaagagagcctctcgcattcccccggaaag SEQ ID NO: 70:
Caninized 39A11 heavy chain AA sequence (VH2) with IgGB
EVQLVESGGDLVKPGGSLRLSCATSGETFS<u>DYYMS</u>WVRQAPGKGLEWMG<u>FIRNKANGYTTEYSASLKG</u>RF

TISRDNAKNMAYLQMNSLRAEDTAVYYCVR<u>FGLMYYFDY</u>WGQGTTLTVSSASTTAPSVFPLAPSCGSTSG

STVALACLVSGYFPEPVTVSWNSGSLTSGVHTFPSVLQSSGLYSLSSMVTVPSSRWPSETFTCNVAHPAS

KTKVDKPVPKRENGRVPRPPDCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVNNKALPSPIERTISKARGQAH

QPSVYVLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPGK

SEQ ID NO: 71:
Caninized 39A11 heavy chain NA sequence (VH3) with IgGB
gaagtgaaactggtggaaagcggcggcgatctggtgaaaccgggcggcagcctgcgcctgagctgcgcga ccagcggctttacctttagcgattattatatgagctgggtgcgccaggcgccgggcaaagcgctggaatg gatgggctttattcgcaacaaagcgaacggctataccaccgaatatagcgcgagcctgaaaggccgcttt accattagccgcgataacgcgaaaaacatgctgtatctgcagatgaacagcctgcgcgcggaagataccg cggtgtattattgcgtgcgctttggcctgatgtattattttgattattggggccagggcaccaccctgac cgtgagcagcgcttccacaaccgcgccatcagtctttccgttggccccatcatgcgggtcgacgagcgga tcgactgtggccctggcgtgcttggtgtcgggatactttcccgaacccgtcacggtcagctggaactccg gatcgcttacgagcggtgtgcatacgttcccctcggtcttgcaatcatcagggctctactcgctgtcgag catggtaacggtgccctcatcgaggtggccctccgaaacgttcacatgtaacgtagcacatccagcctcc aaaaccaaggtggataaacccgtgccgaaaagagagaatgggcgggtgcctcgacccccctgattgcccca agtgtccggctccggaaatgctcggtggaccctcagtgtttatcttccctccgaagcccaaggacactct gctgatcgcgcgcactccagaagtaacatgtgtagtggtggaccttgatcccgaggaccccgaagtccag atctcctggtttgtagatgggaaacagatgcagaccgcaaaaactcaacccagagaggagcagttcaacg gaacataccgagtggtatccgtccttccgattggccaccaggactggttgaaagggaagcagtttacgtg taaagtcaacaataaggggttgcctagccctattgagcggacgatttcgaaagctaggggacaggcccac cagccatcggtctatgtccttccgccttcccgcgaggagctctcgaagaatacagtgagccttacatgcc tcattaaggatttcttcccgcctgatatcgacgtagagtggcaatcaaacggtcaacaggagccggaatc -continued

| NUCLEOTIDE (NA) and AMINO ACID (AA) SEQUENCES |
|---|
| caagtatagaaccactccgccccagcttgacgaggacggatcatactttttgtattcaaaactgtcggtg |
| gataagagccggtggcagagaggtgacaccttcatctgtgcggtgatgcacgaagcactccataatcact |
| acacccaagagagcctctcgcattcccccggaaag |
| SEQ ID NO: 72:<br>Caninized 39A11 heavy chain AA sequence (VH3) with IgGB<br>**EVKLVESGGDLVKPGGSLRLSCATSGETFSDYYMSWVRQAPGKALEWMGFIRNKANGYTTEYSASLKG**RF |
| **TISRDNAKNMLYLQMNSLRAEDTAVYYCVRFGLMYYFDYWGQGTTLTVSS**ASTTAPSVFPLAPSCGSTSG |
| STVALACLVSGYFPEPVTVSWNSGSLTSGVHTFPSVLQSSGLYSLSSMVTVPSSRWPSETFTCNVAHPAS |
| KTKVDKPVPKRENGRVPRPPDCPKCPAPEMLGGPSVFIFPPKPKDTLLIARTPEVTCVVVDLDPEDPEVQ |
| ISWFVDGKQMQTAKTQPREEQFNGTYRVVSVLPIGHQDWLKGKQFTCKVNNKALPSPIERTISKARGQAH |
| QPSVYVLPPSREELSKNTVSLTCLIKDFFPPDIDVEWQSNGQQEPESKYRTTPPQLDEDGSYFLYSKLSV |
| DKSRWQRGDTFICAVMHEALHNHYTQESLSHSPGK |
| SEQ ID NO: 73:<br>Caninized 12B3 heavy chain NA sequence (VH1) with IgGBm<br>**gaagtgcagctggtggaaagcggcggcgatctggtgaaaccgggcggcagcctgcgcctgagctgcgtgg** |
| **cgagcggctatacctttaccaactatggcatgaactgggtgcgccaggcgccgggcaaaggcctgcagtg** |
| **ggtggcgtggattaacacctataccggcgaaccgacctatgcggatgattttaaaggccgctttaccatt** |
| **agccgcgataacgcgaaaaacaccctgtatctgcagatgaacagcctgcgcgcggaagataccgcggtgt** |
| **attattgcgcgcgccgcagcatttattatccgtattggggccagggcaccaccctgaccgtgagcagc**gc |
| ttccacaaccgcgccatcagtctttccgttggccccatcatgcgggtcgacgagcggatcgactgtggcc |
| ctggcgtgcttggtgtcgggatactttcccgaacccgtcacggtcagctggaactccggatcgcttacga |
| gcggtgtgcatacgttcccctcggtcttgcaatcatcagggctctactcgctgtcgagcatggtaacggt |
| gccctcatcgaggtggccctccgaaacgttcacatgtaacgtagcacatccagcctccaaaaccaaggtg |
| gataaacccgtgccgaaaagagagaatgggcgggtgcctcgacccccctgattgccccaagtgtccggctc |
| cggaaatgctcggtggaccctcagtgtttatcttccctccgaagcccaaggacactctgctgatcgcgcg |
| cactccagaagtaacatgtgtagtggtggctcttgatcccgaggaccccgaagtccagatctcctggttt |
| gtagatgggaaacagatgcagaccgcaaaaactcaacccagagaggagcagttcgccggaacataccgag |
| tggtatccgtccttccgattggccaccaggactggttgaaagggaagcagtttacgtgtaaagtcaacaa |
| taaggggttgcctagccctattgagcggacgatttcgaaagctaggggacaggcccaccagccatcggtc |
| tatgtccttccgccttcccgcgaggagctctcgaagaatacagtgagccttacatgcctcattaaggatt |
| tcttcccgcctgatatcgacgtagagtggcaatcaaacggtcaacaggagccggaatccaagtatagaac |
| cactccgccccagcttgacgaggacggatcatactttttgtattcaaaactgtcggtggataagagccgg |
| tggcagagaggtgacaccttcatctgtgcggtgatgcacgaagcactccataatcactacacccaagaga |
| gcctctcgcattcccccggaaag |
| SEQ ID NO: 74:<br>Caninized 12B3 heavy chain AA sequence (VH1) with IgGBm<br>**EVQLVESGGDLVKPGGSLRLSCVASGYTFTNYGMNWVRQAPGKGLQWVAWINTYTGEPTYADDFKGRFTI** |
| **SRDNAKNTLYLQMNSLRAEDTAVYYCARRSIYYPYWGQGTTLTVSS**ASTTAPSVFPLAPSCGSTSGSTVA |
| LACLVSGYFPEPVTVSWNSGSLTSGVHTFPSVLQSSGLYSLSSMVTVPSSRWPSETFTCNVAHPASKTKV |
| DKPVPKRENGRVPRPPDCPKCPAPEMLGGPSVFIFPPKPKDTLLIARTPEVTCVVVALDPEDPEVQISWF |
| VDGKQMQTAKTQPREEQFAGTYRVVSVLPIGHQDWLKGKQFTCKVNNKALPSPIERTISKARGQAHQPSV |

-continued

| NUCLEOTIDE (NA) and AMINO ACID (AA) SEQUENCES |
|---|

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

SEQ ID NO: 75:
Caninized 12B3 heavy chain NA sequence (VH2) with IgGBm
gaaattcagctggtgcagagcggcggcgatctggtgaaaccgggcggcagcctgcgcctgagctgcaaag cgagcggctatacctttaccaactatggcatgaactgggtgcgccaggcgccgggcaaaggcctgcagtg gatgggctggattaacacctataccggcgaaccgacctatgcggatgattttaaaggccgctttaccttt agcctggataacgcgaaaaacaccctgtatctgcagatgaacagcctgcgcgcggaagataccgcggtgt atttttgcgcgcgccgcagcatttattatccgtattggggccagggcaccaccctgaccgtgagcagcgc ttccacaaccgcgccatcagtctttccgttggccccatcatgcgggtcgacgagcggatcgactgtggcc ctggcgtgcttggtgtcgggatactttcccgaacccgtcacggtcagctggaactccggatcgcttacga gcggtgtgcatacgttcccctcggtcttgcaatcatcagggctctactcgctgtcgagcatggtaacggt gccctcatcgaggtggccctccgaaacgttcacatgtaacgtagcacatccagcctccaaaaccaaggtg gataaacccgtgccgaaaagagagaatgggcgggtgcctcgacccccctgattgccccaagtgtccggctc cggaaatgctcggtggaccctcagtgtttatcttccctccgaagcccaaggacactctgctgatcgcgcg cactccagaagtaacatgtgtagtggtggctcttgatcccgaggaccccgaagtccagatctcctggttt gtagatgggaaacagatgcagaccgcaaaaactcaacccagagaggagcagttcgccggaacataccgag tggtatccgtccttccgattggccaccaggactggttgaaagggaagcagtttacgtgtaaagtcaacaa taaggggttgcctagccctattgagcggacgatttcgaaagctaggggacaggcccaccagccatcggtc tatgtccttccgccttcccgcgaggagctctcgaagaatacagtgagccttacatgcctcattaaggatt tcttcccgcctgatatcgacgtagagtggcaatcaaacggtcaacaggagccggaatccaagtatagaac cactccgccccagcttgacgaggacggatcatactttttgtattcaaaactgtcggtggataagagccgg tggcagagaggtgacaccttcatctgtgcggtgatgcacgaagcactccataatcactacacccaagaga gcctctcgcattcccccggaaag SEQ ID NO: 76:
Caninized 12B3 heavy chain AA sequence (VH2) with IgGBm
ETQLVQSGGDLVKPGGSLRLSCKASGYTFTNYGMNWVRQAPGKGLQWMGWINTYTGEPTYADDFKGRFTF

SLDNAKNTLYLQMNSLRAEDTAVYFCARRSIYYPYWGQGTTLTVSSASTTAPSVFPLAPSCGSTSGSTVA

LACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVALDPEDPEVQISWF

VDGKQMQTAKTQPREEQFAGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

SEQ ID NO: 77:
Caninized 12B3 heavy chain NA sequence (VH3) with IgGBm
gaaattcagctggtgcagagcggcggcgatctggtgaaaccgggcggcagcgtgcgcctgagctgcaaag cgagcggctatacctttaccaactatggcatgaactgggtgaaacaggcgccgggcaaaggcctgcagtg gatgggctggattaacacctataccggcgaaccgacctatgcggatgattttaaaggccgctttaccttt agcctggataacgcgaaaaacaccgcgtatctgcagattaacagcctgcgcgcggaagataccgcggtgt atttttgcgcgcgccgcagcatttattatccgtattggggccagggcaccaccctgaccgtgagcagcgc ttccacaaccgcgccatcagtctttccgttggccccatcatgcgggtcgacgagcggatcgactgtggcc -continued

| NUCLEOTIDE (NA) and AMINO ACID (AA) SEQUENCES |
| --- |

ctggcgtgcttggtgtcgggatactttcccgaacccgtcacggtcagctggaactccggatcgcttacga gcggtgtgcatacgttcccctcggtcttgcaatcatcagggctctactcgctgtcgagcatggtaacggt gccctcatcgaggtggccctccgaaacgttcacatgtaacgtagcacatccagcctccaaaaccaaggtg gataaacccgtgccgaaaagagagaatgggcgggtgcctcgacccccctgattgccccaagtgtccggctc cggaaatgctcggtggaccctcagtgtttatcttccctccgaagcccaaggacactctgctgatcgcgcg cactccagaagtaacatgtgtagtggtggctcttgatcccgaggaccccgaagtccagatctcctggttt gtagatgggaaacagatgcagaccgcaaaaactcaacccagagaggagcagttcgccggaacataccgag tggtatccgtccttccgattggccaccaggactggttgaaagggaagcagtttacgtgtaaagtcaacaa taaggggttgcctagccctattgagcggacgatttcgaaagctaggggacaggcccaccagccatcggtc tatgtccttccgccttcccgcgaggagctctcgaagaatacagtgagccttacatgcctcattaaggatt tcttcccgcctgatatcgacgtagagtggcaatcaaacggtcaacaggagccggaatccaagtatagaac cactccgccccagcttgacgaggacggatcatactttttgtattcaaaactgtcggtggataagagccgg tggcagagaggtgacaccttcatctgtgcggtgatgcacgaagcactccataatcactacacccaagaga gcctctcgcattcccccggaaag SEQ ID NO: 78:
Caninized 12B3 heavy chain AA sequence (VH3) with IgGBm
ETQLVQSGGDLVKPGGSVRLSCKASGYTFT<u>NYGMN</u>WVKQAPGKGLQWMG<u>WINTYTGEPTYADDFKG</u>RFTF

SLDNAKNTAYLQINSLRAEDTAVYFCAR<u>RSIYYPY</u>WGQGTTLTVSSASTTAPSVFPLAPSCGSTSGSTVA

LACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVALDPEDPEVQISWF

VDGKQMQTAKTQPREEQFAGTYRVVSVLPIGHQDWLKGKQFTCKVNNKALPSPIERTISKARGQAHQPSV

YVLPPSREELSKNTVSLTCLIKDFFPPDIDVEWQSNGQQEPESKYRTTPPQLDEDGSYFLYSKLSVDKSR

WQRGDTFICAVMHEALHNHYTQESLSHSPGK

SEQ ID NO: 79:
Caninized 39A11 heavy chain NA sequence (VH1) with IgGBm
gaagtgcagctggtggaaagcggcggcgatctggtgaaaccgggcggcagcctgcgcctgagctgcgtgg cgagcggctttacctttagcgattattatatgagctgggtgcgccaggcgccgggcaaaggcctggaatg ggtggcgtttattcgcaacaaagcgaacggctataccaccgaatatagcgcgagcctgaaaggccgcttt accattagccgcgataacgcgaaaaacatggcgtatctgcagatgaacagcctgcgcgcggaagataccg cggtgtattattgcgcgagctttggcctgatgtattattttgattattggggccagggcaccaccctgac cgtgagcagcgcttccacaaccgcgccatcagtctttccgttggccccatcatgcgggtcgacgagcgga tcgactgtggccctggcgtgcttggtgtcgggatactttcccgaacccgtcacggtcagctggaactccg gatcgcttacgagcggtgtgcatacgttcccctcggtcttgcaatcatcagggctctactcgctgtcgag catggtaacggtgccctcatcgaggtggccctccgaaacgttcacatgtaacgtagcacatccagcctcc aaaaccaaggtggataaacccgtgccgaaaagagagaatgggcgggtgcctcgacccccctgattgcccca agtgtccggctccggaaatgctcggtggaccctcagtgtttatcttccctccgaagcccaaggacactct gctgatcgcgcgcactccagaagtaacatgtgtagtggtggctcttgatcccgaggaccccgaagtccag atctcctggtttgtagatgggaaacagatgcagaccgcaaaaactcaacccagagaggagcagttcgccg gaacataccgagtggtatccgtccttccgattggccaccaggactggttgaaagggaagcagtttacgtg taaagtcaacaataaggggttgcctagccctattgagcggacgatttcgaaagctaggggacaggcccac -continued

| NUCLEOTIDE (NA) and AMINO ACID (AA) SEQUENCES |
| --- |
| cagccatcggtctatgtccttccgccttcccgcgaggagctctcgaagaatacagtgagccttacatgcc<br>tcattaaggatttcttcccgcctgatatcgacgtagagtggcaatcaaacggtcaacaggagccggaatc<br>caagtatagaaccactccgccccagcttgacgaggacggatcatactttttgtattcaaaactgtcggtg<br>gataagagccggtggcagagaggtgacaccttcatctgtgcggtgatgcacgaagcactccataatcact<br>acacccaagagagcctctcgcattcccccggaaag |
| SEQ ID NO: 80:<br>Caninized 39A11 heavy chain AA sequence (VH1) with IgGBm<br>**EVQLVESGGDLVKPGGSLRLSCVASGETFS<u>DYYMS</u>WVRQAPGKGLEWVA<u>FIRNKANGYTTEYSASLKG</u>RF**<br>**TISRDNAKNMAYLQMNSLRAEDTAVYYCAS<u>FGLMYYFDY</u>WGQGTTLTVSS**ASTTAPSVFPLAPSCGSTSG<br>STVALACLVSGYFPEPVTVSWNSGSLTSGVHTFPSVLQSSGLYSLSSMVTVPSSRWPSETFTCNVAHPAS<br>KTKVDKPVPKRENGRVPRPPDCPKCPAPEMLGGPSVFIFPPKPKDTLLIARTPEVTCVVVALDPEDPEVQ<br>ISWFVDGKQMQTAKTQPREEQFAGTYRVVSVLPIGHQDWLKGKQFTCKVNNKALPSPIERTISKARGQAH<br>QPSVYVLPPSREELSKNTVSLTCLIKDFFPPDIDVEWQSNGQQEPESKYRTTPPQLDEDGSYFLYSKLSV<br>DKSRWQRGDTFICAVMHEALHNHYTQESLSHSPGK |
| SEQ ID NO: 81:<br>Caninized 39A11 heavy chain NA sequence (VH2) with IgGBm<br>**gaagtgcagctggtggaaagcggcggcgatctggtgaaaccgggcggcagcctgcgcctgagctgcgcga**<br>**ccagcggctttacctttagcgattattatatgagctgggtgcgccaggcgccgggcaaaggcctggaatg**<br>**gatgggctttattcgcaacaaagcgaacggctataccaccgaatatagcgcgagcctgaaaggccgcttt**<br>**accattagccgcgataacgcgaaaaacatggcgtatctgcagatgaacagcctgcgcgcggaagataccg**<br>**cggtgtattattgcgtgcgctttggcctgatgtattattttgattattggggccagggcaccaccctgac**<br>**cgtgagcagc**gcttccacaaccgcgccatcagtctttccgttggccccatcatgcgggtcgacgagcgga<br>tcgactgtggccctggcgtgcttggtgtcgggatactttcccgaacccgtcacggtcagctggaactccg<br>gatcgcttacgagcggtgtgcatacgttcccctcggtcttgcaatcatcagggctctactcgctgtcgag<br>catggtaacggtgccctcatcgaggtggccctccgaaacgttcacatgtaacgtagcacatccagcctcc<br>aaaaccaaggtggataaacccgtgccgaaaagagagaatgggcgggtgcctcgaccccctgattgcccca<br>agtgtccggctccggaaatgctcggtggaccctcagtgtttatcttccctccgaagcccaaggacactct<br>gctgatcgcgcgcactccagaagtaacatgtgtagtggtggctcttgatcccgaggaccccgaagtccag<br>atctcctggtttgtagatgggaaacagatgcagaccgcaaaaactcaacccagagaggagcagttcgccg<br>gaacataccgagtggtatccgtccttccgattggccaccaggactggttgaaagggaagcagtttacgtg<br>taaagtcaacaataaggggttgcctagccctattgagcggacgatttcgaaagctaggggacaggcccac<br>cagccatcggtctatgtccttccgccttcccgcgaggagctctcgaagaatacagtgagccttacatgcc<br>tcattaaggatttcttcccgcctgatatcgacgtagagtggcaatcaaacggtcaacaggagccggaatc<br>caagtatagaaccactccgccccagcttgacgaggacggatcatactttttgtattcaaaactgtcggtg<br>gataagagccggtggcagagaggtgacaccttcatctgtgcggtgatgcacgaagcactccataatcact<br>acacccaagagagcctctcgcattcccccggaaag |
| SEQ ID NO: 82:<br>Caninized 39A11 heavy chain AA sequence (VH2) with IgGBm<br>**EVQLVESGGDLVKPGGSLRLSCATSGETFS<u>DYYMS</u>WVRQAPGKGLEWMG<u>FIRNKANGYTTEYSASLKG</u>RF**<br>**TISRDNAKNMAYLQMNSLRAEDTAVYYCVR<u>FGLMYYFDY</u>WGQGTTLTVSS**ASTTAPSVFPLAPSCGSTSG<br>STVALACLVSGYFPEPVTVSWNSGSLTSGVHTFPSVLQSSGLYSLSSMVTVPSSRWPSETFTCNVAHPAS<br>KTKVDKPVPKRENGRVPRPPDCPKCPAPEMLGGPSVFIFPPKPKDTLLIARTPEVTCVVVALDPEDPEVQ |

-continued

| NUCLEOTIDE (NA) and AMINO ACID (AA) SEQUENCES |
|---|

ISWFVDGKQMQTAKTQPREEQFAGTYRVVSVLPIGHQDWLKGKQFTCKVNNKALPSPIERTISKARGQAH

QPSVYVLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPGK

SEQ ID NO: 83:
Caninized 39A11 heavy chain NA sequence (VH3) with IgGBm
gaagtgaaactggtggaaagcggcggcgatctggtgaaaccgggcggcagcctgcgcctgagctgcgcga ccagcggctttacctttagcgattattatatgagctgggtgcgccaggcgccgggcaaagcgctggaatg gatgggctttattcgcaacaaagcgaacggctataccaccgaatatagcgcgagcctgaaaggccgcttt accattagccgcgataacgcgaaaaacatgctgtatctgcagatgaacagcctgcgcgcggaagataccg cggtgtattattgcgtgcgctttggcctgatgtattattttgattattggggccagggcaccaccctgac cgtgagcagcgcttccacaaccgcgccatcagtctttccgttggccccatcatgcgggtcgacgagcgga tcgactgtggccctggcgtgcttggtgtcgggatactttcccgaacccgtcacggtcagctggaactccg gatcgcttacgagcggtgtgcatacgttcccctcggtcttgcaatcatcagggctctactcgctgtcgag catggtaacggtgccctcatcgaggtggccctccgaaacgttcacatgtaacgtagcacatccagcctcc aaaaccaaggtggataaacccgtgccgaaaagagagaatgggcgggtgcctcgacccccctgattgcccca agtgtccggctccggaaatgctcggtggaccctcagtgtttatcttccctccgaagcccaaggacactct gctgatcgcgcgcactccagaagtaacatgtgtagtggtggctcttgatcccgaggaccccgaagtccag atctcctggtttgtagatgggaaacagatgcagaccgcaaaaactcaacccagagaggagcagttcgccg gaacataccgagtggtatccgtccttccgattggccaccaggactggttgaaagggaagcagtttacgtg taaagtcaacaataaggggttgcctagccctattgagcggacgatttcgaaagctaggggacaggcccac cagccatcggtctatgtccttccgccttcccgcgaggagctctcgaagaatacagtgagccttacatgcc tcattaaggatttcttcccgcctgatatcgacgtagagtggcaatcaaacggtcaacaggagccggaatc caagtatagaaccactccgccccagcttgacgaggacggatcatactttttgtattcaaaactgtcggtg gataagagccggtggcagagaggtgacaccttcatctgtgcggtgatgcacgaagcactccataatcact acacccaagagagcctctcgcattcccccggaaag SEQ ID NO: 84:
Caninized 39A11 heavy chain AA sequence (VH3) with IgGBm
EVKLVESGGDLVKPGGSLRLSCATSGETFS<u>DYYMS</u>WVRQAPGKALEWMG<u>FIRNKANGYTTEYSASLKG</u>RF

TISRDNAKNMLYLQMNSLRAEDTAVYYCVR<u>FGLMYYFDY</u>WGQGTTLTVSSASTTAPSVFPLAPSCGSTSG

STVALACLVSGYFPEPVTVSWNSGSLTSGVHTFPSVLQSSGLYSLSSMVTVPSSRWPSETFTCNVAHPAS

KTKVDKPVPKRENGRVPRPPDCPKCPAPEMLGGPSVFIFPPKPKDTLLIARTPEVTCVVVALDPEDPEVQ

ISWFVDGKQMQTAKTQPREEQFAGTYRVVSVLPIGHQDWLKGKQFTCKVNNKALPSPIERTISKARGQAH

QPSVYVLPPSREELSKNTVSLTCLIKDFFPPDIDVEWQSNGQQEPESKYRTTPPQLDEDGSYFLYSKLSV

DKSRWQRGDTFICAVMHEALHNHYTQESLSHSPGK

SEQ ID NO: 125:
Canine CTLA-4 NA sequence (NCBI Reference Sequence: NP_001003106).
atggcgggctttggctttcgccgccatggcgcgcagccggatctggcgagccgcacctggccgtgcaccg cgctgtttagcctgctgtttattccggtgtttagcaaaggcatgcatgtggcgcagccggcggtggtgct ggcgagcagccgcggcgtggcgagctttgtgtgcgaatatggcagcagcggcaacgcggcggaagtgcgc gtgaccgtgctgcgccaggcgggcagccagatgaccgaagtgtgcgcggcgacctataccgtggaagatg aactggcgtttctggatgatagcacctgcaccggcaccagcagcggcaacaaagtgaacctgaccattca -continued

| NUCLEOTIDE (NA) and AMINO ACID (AA) SEQUENCES |
|---|
| gggcctgcgcgcgatggataccggcctgtatatttgcaaagtggaactgatgtatccgccgccgtattat |
| gtgggcatgggcaacggcacccagatttatgtgattgatccggaaccgtgcccggatagcgattttctgc |
| tgtggattctggcggcggtgagcagcggcctgtttttttatagctttctgattaccgcggtgagcctgag |
| caaaatgctgaaaaaacgcagcccgctgaccaccggcgtgtatgtgaaaatgccgccgaccgaaccggaa |
| tgcgaaaaacagtttcagccgtattttattccgattaac |
| SEQ ID NO: 126:<br>Canine CTLA-4 AA sequence (NCBI Reference Sequence: NP_001003106). |
| SEQ ID NO: 138, mature sequence (i.e., minus the signal sequence) in bold:<br>MAGFGFRRHGAQPDLASRTWPCTALFSLLFIPVESKG**MHVAQPAVVLASSRGVASFVCEYGSSGNAAEVR** |
| **VTVLRQAGSQMTEVCAATYTVEDELAFLDDSTCTGTSSGNKVNLTIQGLRAMDTGLYICKVELMYPPPYY** |
| **VGMGNGTQTYVIDPEPCPDSDELLWILAAVSSGLFFYSFLITAVSLSKMLKKRSPLTTGVYVKMPPTEPE** |
| **CEKQFQPYFIPIN** |
| SEQ ID NO: 127:<br>Genetically Modified cFc Region of canine IgGB<br>(From U.S. Pat. No. 10,106,107 B2)<br>LGGPSVFIFPPKPKDTLLIARTPEVTCVVVALDPEDPEVQISWFVDGKQMQTAKTQPREEQFAGTYRVVS |
| VLPIGHQDWLKGKQFTCKVNNKALPSPIERTISKARGQAHQPSVYVLPPSREELSKNTVSLTCLIKDFFP |
| PDIDVEWQSNGQQEPESKYRTTPPQLDEDGSYFLYSKLSVDKSRWQRGDTFICAVMHEALHNHYTQESLS |
| HSPGK |

Example 8

Epitope Mapping of Caninized Anti-cCTLA-4 Monoclonal Antibody 12B3 and 39A11

The interaction of antibodies with their cognate protein antigens is mediated through the binding of specific amino acids of the antibodies (paratopes) with specific amino acids (epitopes) of target antigens. An epitope is an antigenic determinant that causes a specific reaction by an immunoglobulin. An epitope consists of a group of amino acids on the surface of the antigen. A protein of interest may contain several epitopes that are recognized by different antibodies. The epitopes recognized by antibodies are classified as linear or conformational epitopes. Linear epitopes are formed by a stretch of a continuous sequence of amino acids in a protein, while conformational epitopes are composed of amino acids that are discontinuous (e.g., far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs and help elucidate their mechanisms of action. Epitope information on canine CTLA-4 can also elucidate unique epitopes, and define the protective or pathogenic effects of vaccines. Epitope identification also can lead to development of subunit vaccines based on chemical or genetic coupling of the identified peptide epitope to a carrier protein or other immunostimulating agents.

Epitope mapping can be carried out using polyclonal or monoclonal antibodies and several methods are employed for epitope identification depending on the suspected nature of the epitope (i.e., linear versus conformational). Mapping linear epitopes is more straightforward and relatively, easier to perform. For this purpose, commercial services for linear epitope mapping often employ peptide scanning. In this case, an overlapping set of short peptide sequences of the target protein are chemically synthesized and tested for their ability to bind antibodies of interest. The strategy is rapid, high-throughput, and relatively inexpensive to perform. On the other hand, mapping of a discontinuous epitope is more technically challenging and requires more specialized techniques such as x-ray co-crystallography of a monoclonal antibody together with its target protein, Hydrogen-Deuterium (H/D) exchange, Mass Spectrometry coupled with enzymatic digestion as well as several other methods known to those skilled in the art.

Mapping of Canine CTLA-4 Receptor Alpha Epitopes Using Mass Spectroscopy:

In order to determine the epitope for caninized 12B3 (exemplified by 12B3L2H3) and 39A11 (exemplified by 39A11L3H3) on canine CTLA-4, each of the complexes of cCTLA-4/c12B3L2H3 and cCTLA-4/c39A11L2H3 was incubated with deuterated cross-linkers and subjected to multi-enzymatic cleavage. After enrichment of the cross-linked peptides, the samples were analyzed by high resolution mass spectrometry (nLC-LTQ-Orbitrap MS) and the data generated were analyzed using XQuest and Stavrox software.

Figure 7:
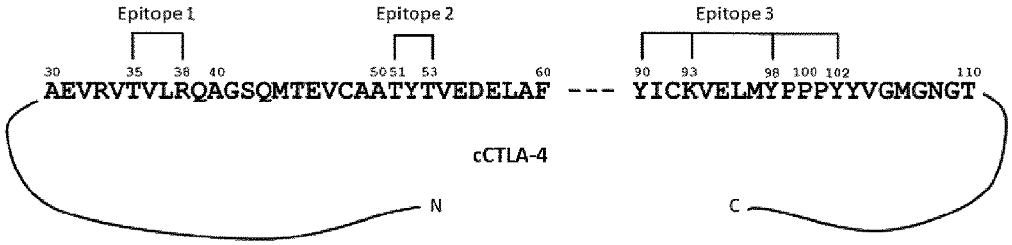
FIG. 7A-7B provides the binding epitopes on cCTLA-4 for c12B3 (FIG. 7A) and c39A11 (FIG. 7B). Two regions of the canine CTLA-4 protein are depicted and have the amino acid sequences of SEQ ID NO: 132 and SEQ ID NO: 133, respectively (see, Table 8 below). Both antibodies bind to the amino acid sequence of SEQ ID NO: 136, which contains the MYPPPY motif (SEQ ID NO: 137), and to the amino acid sequence of SEQ ID NO: 134. c12B3 also binds to the amino acid sequence of SEQ ID NO: 135.
Figure 7:
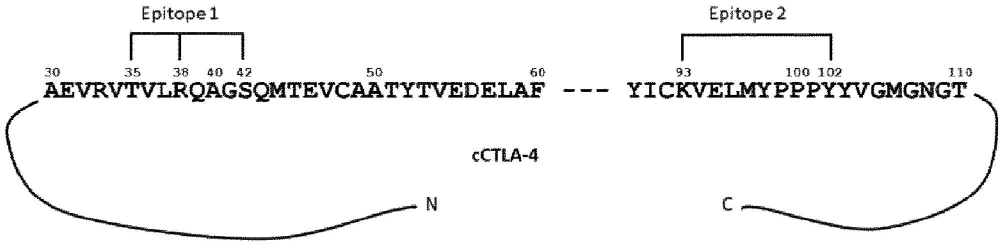

The analysis indicates that c12B3L2H3 interacts with the amino acid residues at position 35, 38, 51, 53, 90, 93, 98 and 102 on cCTLA-4 comprising the amino acid sequence of SEQ ID NO: 138 (FIG. 7A); c39A11L2H3 interacts with the amino acid residues at position 35, 38, 42, 93 and 102 on cCTLA-4 comprising the amino acid sequence of SEQ ID NO: 138 (FIG. 7B). Two specific regions of the canine CTLA 4 protein are depicted in FIGS. 7A and 7B: the amino acid sequences of SEQ ID NO: 132 and SEQ ID NO: 133, respectively (see, Table 8 below). Notably, both antibodies bind to SEQ ID NO: 134 and SEQ ID NO: 136, which comprises the MYPPPY motif (SEQ ID NO: 137), on cCTLA-4. The MYPPPY (SEQ ID NO: 137) motif forms the loop binding with CD80 and CD86, which is conservative motif for CTLA 4 across species. c12B3 also appears to bind one additional region on canine CTLA-4, that comprising the amino acid sequence of SEQ ID NO: 135. Combined with the results of Example 4, the epitope mapping results further confirm that both c12B3 and c39A11 are functional antibodies with the ability to block the interaction of canine CTLA-4 with its ligand CD80 and CD86. Moreover, caninized antibodies that bind to the epitopes in SEQ ID NO: 134 and SEQ ID NO: 136 are also part of the present invention.

TABLE 8

| AMINO ACID REGIONS OF CANINE CTLA-4 THAT THE 12B3 AND C39A1 BIND | |
|---|---|
| SEQ ID NO: 132: | AEVRVTVLRQAGSQMTEVCAATYTVEDELAF |
| SEQ ID NO: 133: | YICKVELMYPPPYYVGMGNGT |
| SEQ ID NO: 134: | TVLRQAGS |
| SEQ ID NO: 135: | ATYTV |
| SEQ ID NO: 136: | YICKVELMYPPPY |
| SEQ ID NO: 137: | MYPPPY |

We claim:

1. An isolated mammalian antibody or an antigen binding fragment thereof that binds canine Cytotoxic T-Lymphocyte-Associated protein 4 (CTLA-4) and blocks the binding of canine CTLA-4 with canine CD80, blocks the binding of canine CTLA-4 with canine CD86, or blocks both the binding of canine CTLA-4 with canine CD80 and the binding of canine CTLA-4 with canine CD86;

wherein said antibody or antigen binding fragment thereof comprises:

(a) a light chain variable region (VL) complementarity-determining region (CDR)-1 comprising the amino acid sequence of SEQ ID NO: 92;

(b) a VLCDR-2 comprising the amino acid sequence of SEQ ID NO: 94;

(c) a VLCDR-3 comprising the amino acid sequence of SEQ ID NO: 96;

(d) a heavy chain variable region (VH) CDR-1 comprising the amino acid sequence of SEQ ID NO: 86;

(e) a VHCDR-2 comprising the amino acid sequence of SEQ ID NO: 88; and (f) a VHCDR-3 comprising the amino acid sequence of SEQ ID NO: 90.

2. The isolated mammalian antibody or antigen binding fragment thereof of claim 1, wherein the mammalian antibody is a murine antibody.

3. The isolated mammalian antibody or antigen binding fragment thereof of claim 1, wherein the antibody or antigen binding fragment thereof is a caninized antibody or a caninized antigen binding fragment.

4. The isolated mammalian antibody or antigen binding fragment thereof of claim 3, further comprising a hinge region that comprises an amino acid sequence selected from the group consisting of SEQ ID NO: 128, SEQ ID NO: 129, SEQ ID NO: 130, and SEQ ID NO: 131.

5. The isolated mammalian antibody or antigen binding fragment thereof of claim 3, comprising a VH; wherein the VH comprises an amino acid sequence of a VH of a heavy chain comprising an amino acid sequence selected from the group consisting of SEQ ID NO: 62, SEQ ID NO: 64, SEQ ID NO: 66, SEQ ID NO:74, SEQ ID NO:76, and SEQ ID NO: 78.

6. The isolated mammalian antibody or antigen binding fragment thereof of claim 5, wherein the heavy chain is encoded by a nucleotide acid sequence selected from the group consisting of SEQ ID NO: 61, SEQ ID NO: 63, SEQ ID NO: 65, SEQ ID NO: 73, SEQ ID NO: 75, and SEQ ID NO: 77.

7. The isolated mammalian antibody or antigen binding fragment thereof of claim 3, wherein the antibody or antigen binding fragment thereof binds to any one or more amino acid sequences selected from the group consisting of SEQ ID NO: 132, SEQ ID NO: 133, SEQ ID NO: 134, SEQ ID NO: 135, SEQ ID NO: 136, and SEQ ID NO: 137.

8. A pharmaceutical composition comprising the isolated mammalian caninized antibody or antigen binding fragment thereof of claim 3, and a pharmaceutically acceptable carrier or diluent.

9. The isolated mammalian antibody or antigen binding fragment thereof of claim 3, comprising a VL; wherein the VL comprises an amino acid sequence of a VL of a light chain comprising an amino acid sequence selected from the group consisting of SEQ ID NO:50, SEQ ID NO:52, and SEQ ID NO:54.

10. The isolated mammalian antibody or antigen binding fragment thereof of claim 9, wherein the light chain is encoded by a nucleotide sequence selected from the group consisting of SEQ ID NO:49, SEQ ID NO:51, and SEQ ID NO:53.

11. The isolated mammalian antibody or antigen binding fragment thereof of claim 3, comprising a VH and a VL;

wherein the VH comprises an amino acid sequence of a VH of a heavy chain comprising an amino acid sequence selected from the group consisting of SEQ ID NO:62, SEQ ID NO:64, SEQ ID NO:66, SEQ ID NO:74, SEQ ID NO: 76, and SEQ ID NO: 78; and wherein the VL comprises an amino acid sequence of a VL of a light chain comprising an amino acid sequence selected from the group consisting of SEQ ID NO:50, SEQ ID NO: 52, and SEQ ID NO:54.

12. The isolated mammalian antibody or antigen binding fragment thereof of claim 11, wherein the heavy chain encoded by a nucleotide sequence selected from the group consisting of SEQ ID NO:61, SEQ ID NO:63, SEQ ID NO:65, SEQ ID NO:73, SEQ ID NO:75, and SEQ ID NO:77; and wherein the light chain is encoded by a nucleotide sequence selected from the group consisting of SEQ ID NO:49, SEQ ID NO:51, and SEQ ID NO:53.

13. The isolated mammalian antibody or antigen binding fragment thereof of claim 3, comprising a VH and a VL; wherein the VH comprises an amino acid sequence of a VH of a heavy chain comprising an amino acid sequence set forth in SEQ ID NO:64 or SEQ ID NO: 76; and wherein the VL comprises an amino acid sequence of a VL of a light chain comprising the amino acid sequence set forth in SEQ ID NO: 54.

14. The isolated mammalian antibody or antigen binding fragment thereof of claim 3, comprising a VH and a VL; wherein the VH comprises an amino acid sequence of a VH of a heavy chain comprising an amino acid sequence set forth in SEQ ID NO:66 or SEQ ID NO: 78; and wherein the VL comprises an amino acid sequence of a VL of a light chain comprising the amino acid sequence set forth in SEQ ID NO: 54.

15. The isolated mammalian antibody or antigen binding fragment thereof of claim 3, comprising a VH and a VL; wherein (a) the VH comprises an amino acid sequence of a VH of a heavy chain comprising an amino acid sequence set forth in SEQ ID NO:64 or SEQ ID NO:76; and wherein the VL comprises an amino acid sequence of a VL of a light chain comprising the amino acid sequence set forth in SEQ ID NO:50;

(b) the VH comprises an amino acid sequence of a VH of a heavy chain comprising an amino acid sequence set forth in SEQ ID NO:62 or SEQ ID NO:74; and wherein the VL comprises an amino acid sequence of a VL of a light chain comprising the amino acid sequence set forth in SEQ ID NO:50;

(c) the VH comprises an amino acid sequence of a VH of a heavy chain comprising an amino acid sequence set forth in SEQ ID NO:66 or SEQ ID NO:78; and wherein the VL comprises an amino acid sequence of a VL of a light chain comprising the amino acid sequence set forth in SEQ ID NO:50;

(d) the VH comprises an amino acid sequence of a VH of a heavy chain an amino acid sequence set forth in SEQ ID NO:62 or SEQ ID NO:74; and wherein the VL comprises an amino acid sequence of a VL of a light chain comprising the amino acid sequence set forth in SEQ ID NO:54;

(e) the VH comprises an amino acid sequence of a VH of a heavy chain comprising an amino acid sequence set forth in SEQ ID NO:64 or SEQ ID NO:76; and wherein the VL comprises an amino acid sequence of a VL of a light chain comprising the amino acid sequence set forth in SEQ ID NO:52;

(f) the VH comprises an amino acid sequence of a VH of a heavy chain comprising an amino acid sequence set forth in SEQ ID NO:62 or SEQ ID NO:74; and wherein the VL) comprises an amino acid sequence of a VL of a light chain comprising the amino acid sequence set forth in SEQ ID NO:52; or (g) the VH comprises an amino acid sequence of a VH of a heavy chain comprising an amino acid sequence set forth in SEQ ID NO:66 or SEQ ID NO:78; and wherein the VL comprises an amino acid sequence of a VL of a light chain comprising the amino acid sequence set forth in SEQ ID NO:52.

16. The isolated mammalian antibody or antigen binding fragment thereof of claim 3, comprising:

(a) a heavy chain that comprises the amino acid sequence of SEQ ID NO:62 or a sequence that is at least about 95% identical to SEQ ID NO:62, and a light chain that comprises the amino acid sequence of SEQ ID NO:50 or a sequence that is at least about 95% identical to SEQ ID NO:50;

(b) a heavy chain that comprises the amino acid sequence of SEQ ID NO:62 or a sequence that is at least about 95% identical to SEQ ID NO:62, and a light chain that comprises the amino acid sequence of SEQ ID NO:52 or a sequence that is at least about 95% identical to SEQ ID NO:52;

(c) a heavy chain that comprises the amino acid sequence of SEQ ID NO:62 or a sequence that is at least about 95% identical to SEQ ID NO:62, and a light chain that comprises the amino acid sequence of SEQ ID NO:54 or a sequence that is at least about 95% identical to SEQ ID NO:54;

(d) a heavy chain that comprises the amino acid sequence of SEQ ID NO:64 or a sequence that is at least about 95% identical to SEQ ID NO:64, and a light chain that comprises the amino acid sequence of SEQ ID NO:50 or a sequence that is at least about 95% identical to SEQ ID NO:50;

(e) a heavy chain that comprises the amino acid sequence of SEQ ID NO:64 or a sequence that is at least about 95% identical to SEQ ID NO:64, and a light chain that comprises the amino acid sequence of SEQ ID NO:52 or a sequence that is at least about 95% identical to SEQ ID NO:52;

(f) a heavy chain that comprises the amino acid sequence of SEQ ID NO:64 or a sequence that is at least about 95% identical to SEQ ID NO:64, and a light chain that comprises the amino acid sequence of SEQ ID NO:54 or a sequence that is at least about 95% identical to SEQ ID NO:54;

(g) a heavy chain that comprises the amino acid sequence of SEQ ID NO:66 or a sequence that is at least about 95% identical to SEQ ID NO:66, and a light chain that comprises the amino acid sequence of SEQ ID NO:50 or a sequence that is at least about 95% identical to SEQ ID NO:50;

(h) a heavy chain that comprises the amino acid sequence of SEQ ID NO:66 or a sequence that is at least about 95% identical to SEQ ID NO:66, and a light chain that comprises the amino acid sequence of SEQ ID NO:52 or a sequence that is at least about 95% identical to SEQ ID NO:52;

(i) a heavy chain that comprises the amino acid sequence of SEQ ID NO:66 or a sequence that is at least about 95% identical to SEQ ID NO:66, and a light chain that comprises the amino acid sequence of SEQ ID NO:54 or a sequence that is at least about 95% identical to SEQ ID NO:54;

(j) a heavy chain that comprises the amino acid sequence of SEQ ID NO:74 or a sequence that is at least about 95% identical to SEQ ID NO:74, and a light chain that comprises the amino acid sequence of SEQ ID NO:50 or a sequence that is at least about 95% identical to SEQ ID NO:50;

(k) a heavy chain that comprises the amino acid sequence of SEQ ID NO:74 or a sequence that is at least about 95% identical to SEQ ID NO:74, and a light chain that comprises the amino acid sequence of SEQ ID NO:52 or a sequence that is at least about 95% identical to SEQ ID NO:52;

(l) a heavy chain that comprises the amino acid sequence of SEQ ID NO:74 or a sequence that is at least about 95% identical to SEQ ID NO:74, and a light chain that comprises the amino acid sequence of SEQ ID NO:54 or a sequence that is at least about 95% identical to SEQ ID NO:54;

(m) a heavy chain that comprises the amino acid sequence of SEQ ID NO:76 or a sequence that is at least about 95% identical to SEQ ID NO:76, and a light chain that comprises the amino acid sequence of SEQ ID NO:50 or a sequence that is at least about 95% identical to SEQ ID NO:50;

(n) a heavy chain that comprises the amino acid sequence of SEQ ID NO:76 or a sequence that is at least about 95% identical to SEQ ID NO:76, and a light chain that comprises the amino acid sequence of SEQ ID NO:52 or a sequence that is at least about 95% identical to SEQ ID NO:52;

(o) a heavy chain that comprises the amino acid sequence of SEQ ID NO:76 or a sequence that is at least about 95% identical to SEQ ID NO:76, and a light chain that comprises the amino acid sequence of SEQ ID NO:54 or a sequence that is at least about 95% identical to SEQ ID NO:54;

(p) a heavy chain that comprises the amino acid sequence of SEQ ID NO:78 or a sequence that is at least about 95% identical to SEQ ID NO:78, and a light chain that comprises the amino acid sequence of SEQ ID NO:50 or a sequence that is at least about 95% identical to SEQ ID NO:50;

(q) a heavy chain that comprises the amino acid sequence of SEQ ID NO:78 or a sequence that is at least about 95% identical to SEQ ID NO:78, and a light chain that comprises the amino acid sequence of SEQ ID NO:52 or a sequence that is at least about 95% identical to SEQ ID NO:52; or (r) a heavy chain that comprises the amino acid sequence of SEQ ID NO:78 or a sequence that is at least about 95% identical to SEQ ID NO:78, and a light chain that comprises the amino acid sequence of SEQ ID NO:54 or a sequence that is at least about 95% identical to SEQ ID NO:54.

17. The isolated mammalian antibody or antigen binding fragment thereof of claim 3, comprising a heavy chain that comprises the amino acid sequence of SEQ ID NO:64 and a light chain that comprises the amino acid sequence of SEQ ID NO:54.

18. The isolated mammalian antibody or antigen binding fragment thereof of claim 3, comprising a heavy chain that comprises the amino acid sequence of SEQ ID NO:76 and a light chain that comprises the amino acid sequence of SEQ ID NO:54.

19. The isolated mammalian antibody or antigen binding fragment thereof of claim 3, comprising a heavy chain that comprises the amino acid sequence of SEQ ID NO:66 and a light chain that comprises the amino acid sequence of SEQ ID NO:54.

20. The isolated mammalian antibody or antigen binding fragment thereof of claim 3, comprising a heavy chain that comprises the amino acid sequence of SEQ ID NO:78 and a light chain that comprises the amino acid sequence of SEQ ID NO:54.

* * * * *